US012753441B2

(12) United States Patent
Bendixen et al.

(10) Patent No.: US 12,753,441 B2
(45) Date of Patent: Oct. 6, 2026

(54) DETECTION OF METHYLATION STATUS

(71) Applicant: PentaBase ApS, Odense C (DK)

(72) Inventors: Kamilla Kolding Bendixen, Odense C (DK); Rasmus Koefoed Petersen, Odense C (DK); Ulf Bech Christensen, Odense C (DK)

(73) Assignee: PentaBase ApS, Odense C (DK)

( * ) Notice: Subject to any disclaimer, the term of this patent is extended or adjusted under 35 U.S.C. 154(b) by 758 days.

(21) Appl. No.: 18/001,601

(22) PCT Filed: Jun. 29, 2021

(86) PCT No.: PCT/EP2021/067880
§ 371 (c)(1),
(2) Date: Dec. 13, 2022

(87) PCT Pub. No.: WO2022/002958
PCT Pub. Date: Jan. 6, 2022

(65) Prior Publication Data

US 2025/0346955 A1 Nov. 13, 2025

(30) Foreign Application Priority Data

Jun. 29, 2020 (EP) .................................... 20182947

(51) Int. Cl.
*C12Q 1/6883* (2018.01)

(52) U.S. Cl.
CPC ...... *C12Q 1/6883* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

2009/0130657 A1 5/2009 Millar
2009/0155791 A1 6/2009 Wojdacz et al.
2010/0068704 A1* 3/2010 Christensen ......... C12Q 1/6813
536/23.1

FOREIGN PATENT DOCUMENTS

JP 2000-511776 A 9/2000
JP 2006-517402 A 7/2006
JP 2009-529337 A 8/2009
JP 2013-544507 A 12/2013
WO WO2003/052132 A2 6/2003
WO WO2007/104318 A2 9/2007
WO WO2009/010776 A1 1/2009
WO WO2009/105830 A1 9/2009
WO WO2003/052134 A1 12/2014
WO WO2017/045689 A1 3/2017
WO WO2017/081171 A1 5/2017

OTHER PUBLICATIONS

Christensen, U. et al., Intercalating nucleic acids containing insertions of 1-0-(1-pyrenylmethyl)glycerol: stabilisation of dsDNA and discrimination of DNA over RNA, Nucleic Acids Research, 30(22): 4918-25, 2002.
Hunter, C. The nature of π-π interactions, Journal of the American Chemical Society, 112(14): 5525-5534, 1990.
Kubista, M., The real-time polymerase chain reaction, Molecular Aspects of Medicine, 27(2-3): 95-125, Apr.-Jun. 2006.
Ehrlich, M., et al., DNA hypomethylation in cancer cells, Epigenomics, 1(2): 239-259, Dec. 2009.
Pendina, A., et al., DNA methylation—a universal mechanism for regulating gene activity, Environmental Genetics, II (1): 27-37, 2004.
Telenius, et al., "Degenerate Oligonucleotide-Primed PCR: General Amplification of Target DNA by a Single Degenerate Primer", Genomics, vol. 13, No. 3, 718-725, Jul. 1992.
Rose, et al., "Consensus-degenerate hybrid oligonucleotide primers for amplification of distantly related sequences", Nucleic Acids Research, vol. 26, No. 7, 1628-1635, Apr. 1998.
Watzdorf, et al., "Modified Nucleotides for Discrimination between Cytosine and the Epigenetic Marker 5-Mthylcytosine", Angew Chem Int Ed Engl, 55:9, 3229-3232, Feb. 2016.
Yang, D, "Detection of mRNA Single-Base Mutations and RNA Methylation Modifications Based on Enzyme-Cleavage-Assisted Nucleic Acid Amplification Technology", Shaanxi Normal University, Dissertation Supervisor: Professor Zhengping Li, Apr. 2020.

* cited by examiner

*Primary Examiner* — Carla J Myers
(74) *Attorney, Agent, or Firm* — Weston R. Gould; DINSMORE & SHOHL LLP

(57) ABSTRACT

The present invention relates to a method for determining epigenetic modification status of at least one nucleotide of interest (NOI) in a target nucleic acid sequence of interest. The invention is based on the finding that certain oligonucleotides comprising hydrophobic nucleotides have significant differences in melting temperature to epigenetically modified target nucleic acids compared to unmodified target nucleic acids. The methods have multiple applications for example in diagnosis. The invention also provides oligonucleotides, in particular BasePrimers for use in such methods.

19 Claims, 16 Drawing Sheets

Specification includes a Sequence Listing.

DETECTION OF METHYLATION STATUS

CROSS REFERENCE TO RELATED APPLICATIONS

This application is a U.S. National Stage under 35 U.S.C. § 371 of PCT/EP2021/067880 filed Jun. 23, 2021, which depends from and claims priority to European application number 20181826.7 filed Jun. 24, 2020, the entire contents of each of which are incorporated herein by reference.

SEQUENCE LISTING

The instant application contains a Sequence Listing which has been submitted electronically in ASCII format and is hereby incorporated by reference in its entirety. Said ASCII copy, created Oct. 25, 2022, is named "P5659US00-Corrected_Sequence list_ST25.txt" and is 32,879 bytes in size.

BACKGROUND

Methylation is an example of an epigenetic modification of DNA where a methyl group is added to one of the four DNA bases. Most commonly, the methyl-group is added to cytosine in the 5 position of the nucleobase. DNA methylation in promotor regions is involved in regulation of the expression of genes.

In the progression of cancer, several genes are silenced due to hypermethylation of their promoters, which cause repression of the gene transcription. Methylation of specific genes may be used both as a prognostic factor for cancer, but it can also be used in selection of optimal treatment for the patient. In the brain tumor, glioblastoma, methylation of MGMT (06-methylguanine-DNA methyltransferase) promotor has been correlated with better prognosis and more efficient response to alkylating chemotherapy such as temozolomide (TMZ). Patients with glioblastoma are therefore often tested for methylation of MGMT.

Several methods are available for detection of methylation, and the gold standard method requires a bisulfite pre-treatment of the DNA. The pre-treatment converts unmethylated cytosine to uracil, while methylated cytosine is unchanged. The bisulfite treatment is time consuming, requires large input of DNA and is prone to give false results as too short reaction time will cause incomplete conversion of unmethylated cytosine, and too long reaction time can cause conversion of methylated cytosine. This leads to a risk of both false positive and false negative results. Bisulfite-free methods have also been developed, but they all require an alternative conversion or are not PCR-based. Kits for bisulfite conversion are commercially available, but typically requires at least 15 handling steps.

Hydrophobic nucleotides, for example Intercalating nucleic acids (INA™) comprise a hydrophobic moiety, such as an intercalator. An intercalator is a flat, conjugated aromatic or heteroaromatic ring system that can participate in the stacking of DNA or RNA duplexes. Hydrophobic nucleotides do not participate in the Watson Crick base paring. When an oligonucleotide with an incorporated hydrophobic nucleotide is bound to a non-modified DNA sequence, the hydrophobic moiety position itself in the center of the DNA helix. The interaction between the hydrophobic nucleotide and DNA bases causes increased stability of double stranded DNA.

SUMMARY

A simple method for detection of epigenetic modifications of the nucleobases of a nucleic acid such as analysing for methylation of a nucleobase without conversion of the nucleic acid is beneficial due to faster detection of methylated nucleic acids, no loss of sample during a conversion step and no uncertainty based on conversion being incomplete or unspecific. In a clinical setting early detection of epigenetic modifications such as the methylation status may lead to faster diagnosis of patients and hence to earlier start of treatment. A better method could potentially also better quantify the level of methylation and expand the use of methylation status, for example in treatment and monitoring or diagnosis of cancers.

The present invention provides very fast methods for detection of epigenetic modifications in nucleic acids, for example for detection of methylated DNA. The methods are based on the finding that a synthetic oligonucleotide comprising at least one hydrophobic nucleotide can have a surprisingly high difference in affinity (melting temperature) towards DNA with an epigenetic modification in the nucleobase and DNA without said epigenetic modification, respectively, subject to the design. This is in particular the case, when the hydrophobic nucleotide is positioned within the synthetic oligonucleotide so that it would intercalate between the potentially epigenetically modified nucleotide (such as methylated) and the nucleotide immediately 3' thereof on the target nucleic acid.

Whereas the methods of the invention can be used for detection of epigenetic modifications of any nucleotide in any kind of nucleic acid, the methods are particularly useful for detection of cytosine methylation in DNA. In such cases the synthetic oligonucleotide is preferably designed in a manner so that the hydrophobic nucleotide is positioned so that it would intercalate between the potentially methylated cytosine and the nucleotide immediately 3' thereof (most often a guanine).

This surprisingly high difference in melting temperature can be exploited for easy detection of nucleic acid methylation status using various methods. For example, the nucleic acid methylation status can be detected by a simple PCR method. Importantly, no pre-treatment of the nucleic acid is required for the methods of the invention. Thus, nucleic acid methylation can be detected in a one-step PCR by designing adequate primers comprising hydrophobic nucleotide(s).

In preferred embodiments of the invention, the methods are performed using a type of primers referred to as BasePrimers, which are described in more detail below.

It is an aspect of the invention to provide methods of determining methylation status of at least one nucleotide of interest (NOI) in a target nucleic acid sequence of interest, wherein said target nucleic acid sequence comprises a target anchor sequence comprising said NOI, said method comprising the steps of a. Providing an oligonucleotide comprising an anchor sequence (An), wherein the anchor sequence is a sequence at least 50% complementary to said target anchor sequence, wherein the anchor sequence comprises at least one hydrophobic nucleotide (H) positioned between the nucleotide complementary to said NOI and the nucleotide in the oligonucleotide immediately 5' thereof;
b. Incubating said oligonucleotide with said target nucleic acid of interest at a temperature which is higher than the melting temperature between said oligonucleotide and the target nucleic acid sequence of interest when said NOI is unmethylated,
c. Detecting whether said oligonucleotide anneals to said target nucleic acid of interest, thereby determining the methylation status, wherein i. said hydrophobic nucleotide (H) has the structure

X—Y—Q wherein

X is a nucleotide or nucleotide analogue or a backbone monomer unit capable of being incorporated into the backbone of a nucleic acid or nucleic acid analogue, Q is an intercalator which is not taking part in Watson-Crick hydrogen bonding; and Y is a linker moiety linking said nucleotide or nucleotide analogue or backbone monomer unit and said intercalator.

It is also an aspect of the invention to provide methods of determining methylation status of at least one nucleotide of interest (NOI) in a non-modified target nucleic acid sequence of interest, wherein said target nucleic acid sequence comprises a target anchor sequence comprising said NOI, said method comprising the steps of a. Providing an oligonucleotide comprising an anchor sequence (An), wherein the anchor sequence is a sequence at least 50% complementary to said target anchor sequence, wherein the anchor sequence comprises at least one hydrophobic nucleotide (H) positioned between the nucleotide complementary to said NOI and the nucleotide immediately 5' thereof;
b. Incubating said oligonucleotide with said target nucleic acid of interest at a temperature which is higher than the melting temperature between said oligonucleotide and the target nucleic acid sequence of interest when said NOI is unmethylated,
c. Detecting whether said oligonucleotide anneals to said target nucleic acid of interest, thereby determining the methylation status, wherein i. said hydrophobic nucleotide (H) has the structure

X—Y—Q, wherein

X is a nucleotide or nucleotide analogue or a backbone monomer unit capable of being incorporated into the backbone of a nucleic acid or nucleic acid analogue;

Q is an intercalator which is not taking part in Watson-Crick hydrogen bonding; and Y is a linker moiety linking said nucleotide or nucleotide analogue or backbone monomer unit and said intercalator; and ii. said oligonucleotide has the structure 5'-An-Lp-St-3', wherein An is the anchor sequence;

Lp is a loop sequence, which is not complementary to the target nucleic acid sequence of interest, wherein the loop sequence consists of a single nucleic acid sequence capable of forming a protruding structure, such as a loop structure or a stem structure, or consists of two or more nucleic acid sequences capable of hybridising at least partly to one another to form a complex which is capable of forming a protruding structure, such as a loop structure or a stem structure;

St is a starter sequence, capable of hybridizing to a target starter sequence, wherein the target starter sequence is a sequence of the target nucleic acid sequence positioned 5' to the target anchor sequence.

In another aspect, the present invention provides a method for determining the risk of whether an individual suffers from a clinical condition, or the risk of an individual to contract a clinical condition, wherein the clinical condition is associated with the methylation status of a NOI in a nucleic acid of interest, said method comprising a. Providing a sample obtained from said individual;
b. Determining the methylation status of said NOI in said sample by performing the method as disclosed herein, wherein said methylation status is indicative of the presence of or risk of contracting said clinical condition.

In some aspects, the present invention provides a method for determining the likelihood of effect of a treatment of a clinical condition in an individual in need thereof, wherein the effect of said treatment of said clinical condition is associated with the methylation status of a NOI in a nucleic acid of interest, said method comprising a. Providing a sample obtained from said individual;
b. Determining the methylation status of said NOI in said sample by performing the method as disclosed herein, wherein said methylation status is indicative of the effects of different treatment regimens on said clinical condition.

In some aspects is provided an oligonucleotide comprising or consisting of the following general structure:

$$5'(N)_n—HG—(N)_m—HG—(N)_p\text{-}3',$$

wherein N is any nucleotide or nucleotide analogue; and
G is the nucleotide guanine; and
n is an integer ≥0; and
m is an integer ≥1; and
p is an integer ≥0; and
H is a hydrophobic nucleotide
wherein said hydrophobic nucleotide has the structure

X—Y—Q wherein

X is a nucleotide or nucleotide analogue or a backbone monomer unit capable of being incorporated into the backbone of a nucleic acid or nucleic acid analogue, Q is an intercalator which is not taking part in Watson-Crick hydrogen bonding; and Y is a linker moiety linking said nucleotide or nucleotide analogue or backbone monomer unit and said intercalator.

In yet another aspect is provided an oligonucleotide comprising or consisting of the following general structure:

$$5'(N)_n—CGH—(N)_m—CGH—(N)_p\text{-}3',$$

wherein N is any nucleotide or nucleotide analogue; and
C is the nucleotide cytosine; and
G is the nucleotide guanine; and
n is an integer ≥0; and
m is an integer ≥1; and
p is an integer ≥0; and
H is a hydrophobic nucleotide wherein said hydrophobic nucleotide has the structure

X—Y—Q wherein

X is a nucleotide or nucleotide analogue or a backbone monomer unit capable of being incorporated into the backbone of a nucleic acid or nucleic acid analogue, Q is an intercalator which is not taking part in Watson-Crick hydrogen bonding; and Y is a linker moiety linking said nucleotide or nucleotide analogue or backbone monomer unit and said intercalator.

The invention is further defined by the claims attached hereto.

ZUBR Green. The methyl-specific assay comprises MGMT_FwLoop5C instead of MGMT_Fw2C_suE.

Figure 11:
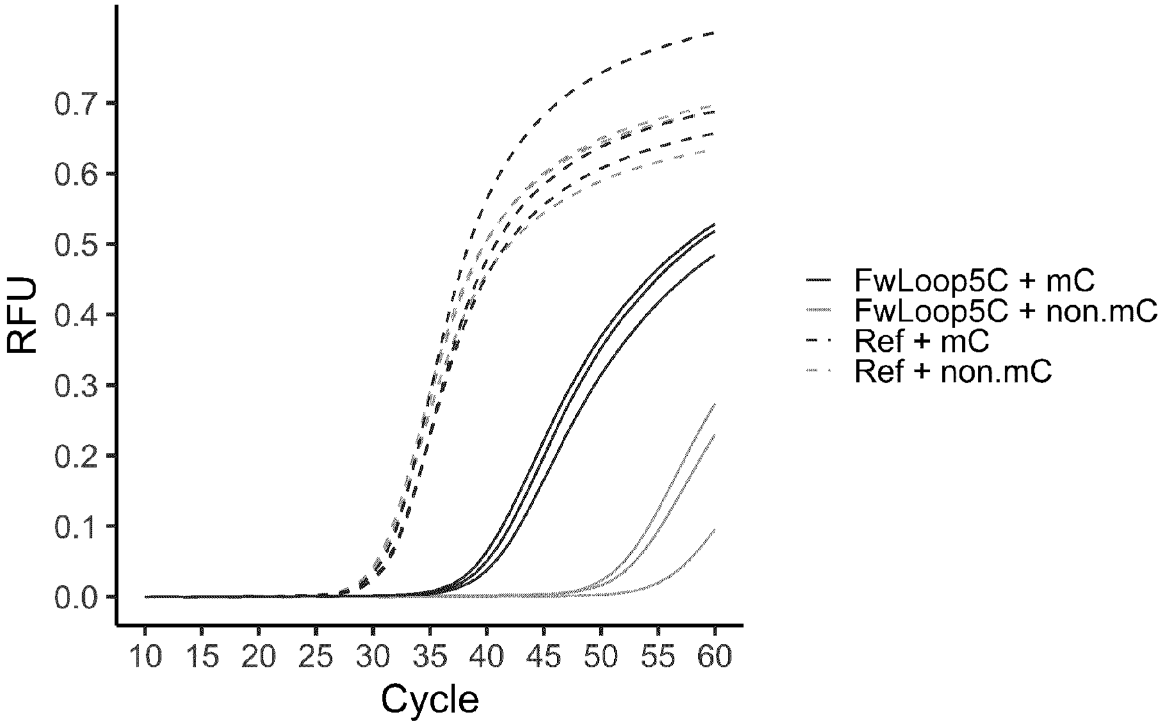

FIG. 11. PCR curves of reference and methyl-specific assay on methylated and non-methylated DNA. The RFU is plotted as a function of cycle. PCR Program F (see Table 15) was used. 700 nM MGMT_Fw2C_suE, 700 nM MGMT_Rev2C_suE and 1% ZUBR Green was used in the reference assay, and the methyl-specific assay had 500 nM MGMT_FwLoop5C instead of MGMT_Fw2C_suE.

Figure 12:
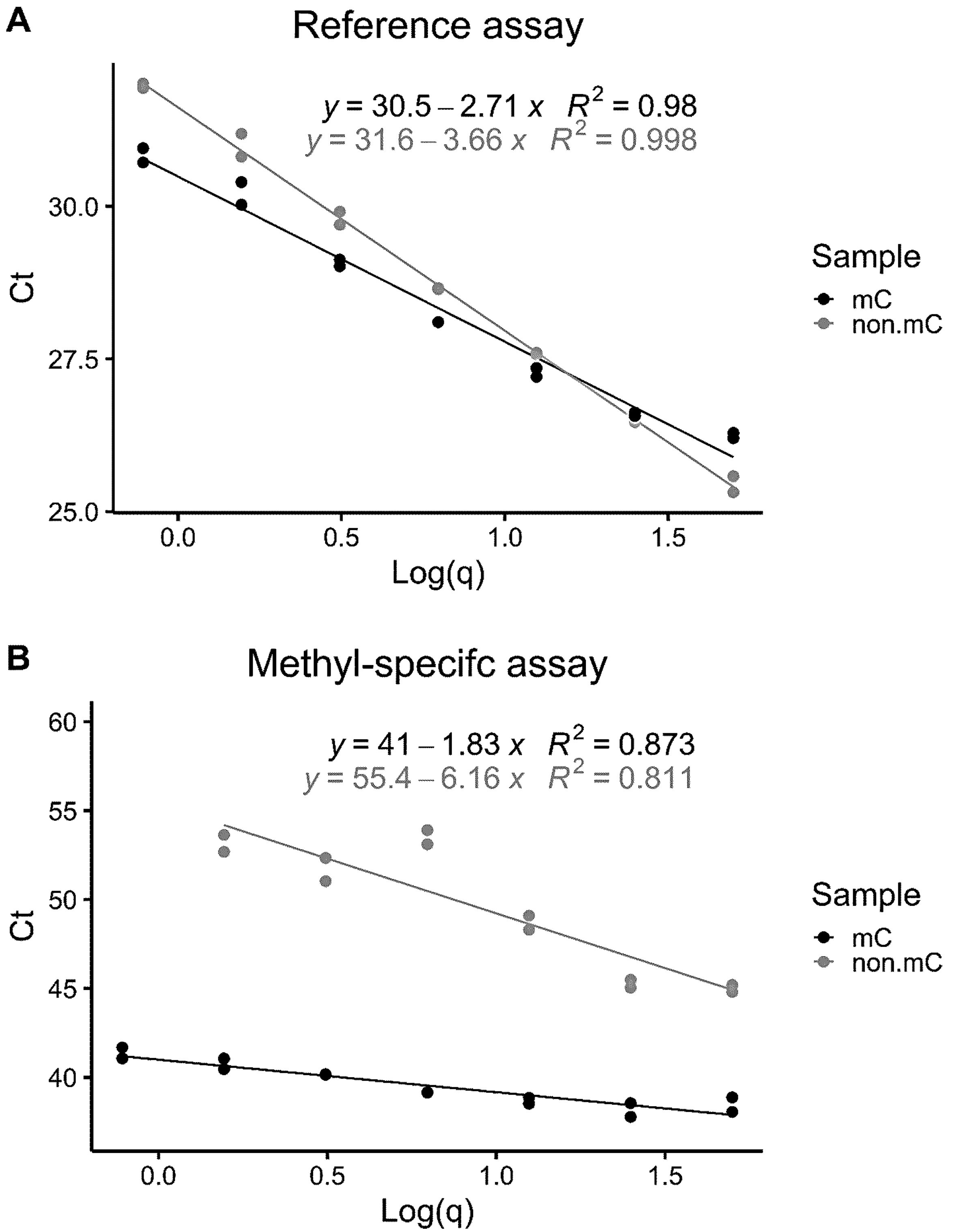

FIG. 12. Linearity results from reference and methyl-specific assay. The Ct is plotted as a function of the logarithm of the input quantity of template [log (q)]. A) Results from reference assay. B) Results from methyl-specific assay with MGMT_FwLoop5C. PCR Program F was used. 700 nM MGMT_Fw2C_suE, 700 nM MGMT_Rev2C_suE and 1% ZUBR Green was used in the reference assay, and the methyl-specific assay had 500 nM MGMT_FwLoop5C instead of MGMT_Fw2C_suE.

FIG. 13.

Sensitivity studies results on MyGo Pro Real-time PCR instrument (It-Is lifescience). The ΔCt is plotted as a function of % methylation. PCR Program F (see Table 15) was used. 700 nM MGMT_Fw2C_suE, 700 nM Rev2C and 1% ZUBR Green was used in the reference assay, and the methyl-specific assay had 500 nM MGMT_FwLoop5C instead of MGMT_Fw2C_suE.

Figure 14:
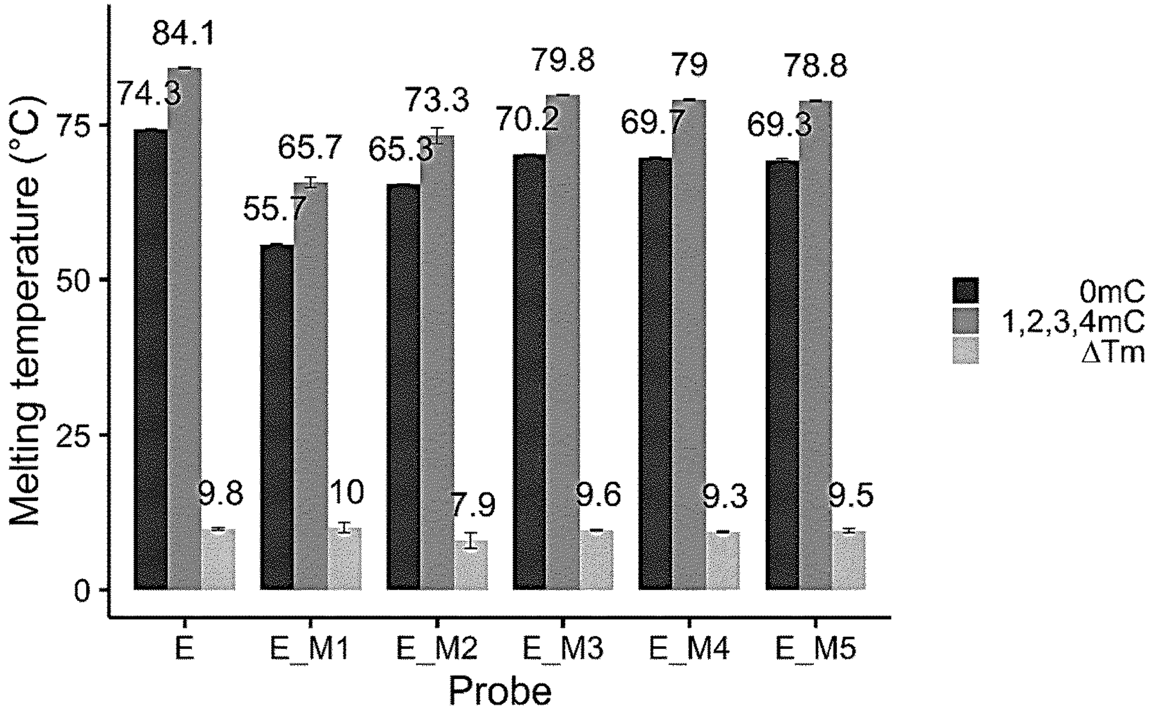

FIG. 14. Bar plot of $T_m$ and $\Delta T_m$ of different types of mutated probes (probes with mismatches). MGMT probes comprising hydrophobic nucleotides of type E with (E_M1, E_M2, E_M3, E_M4, E_M5) and without (E) mutations (mismatches) were mixed individually with a non-methylated (0mC) or a fully methylated (1,2,3,4mC) targets, respectively. The sequences of the MGMT probes as well as of the MGMT targets tested are provided in Table 20. The difference in melting temperature between the methylated and non-methylated target is illustrated. The mean values are shown above the bars.

Figure 15:
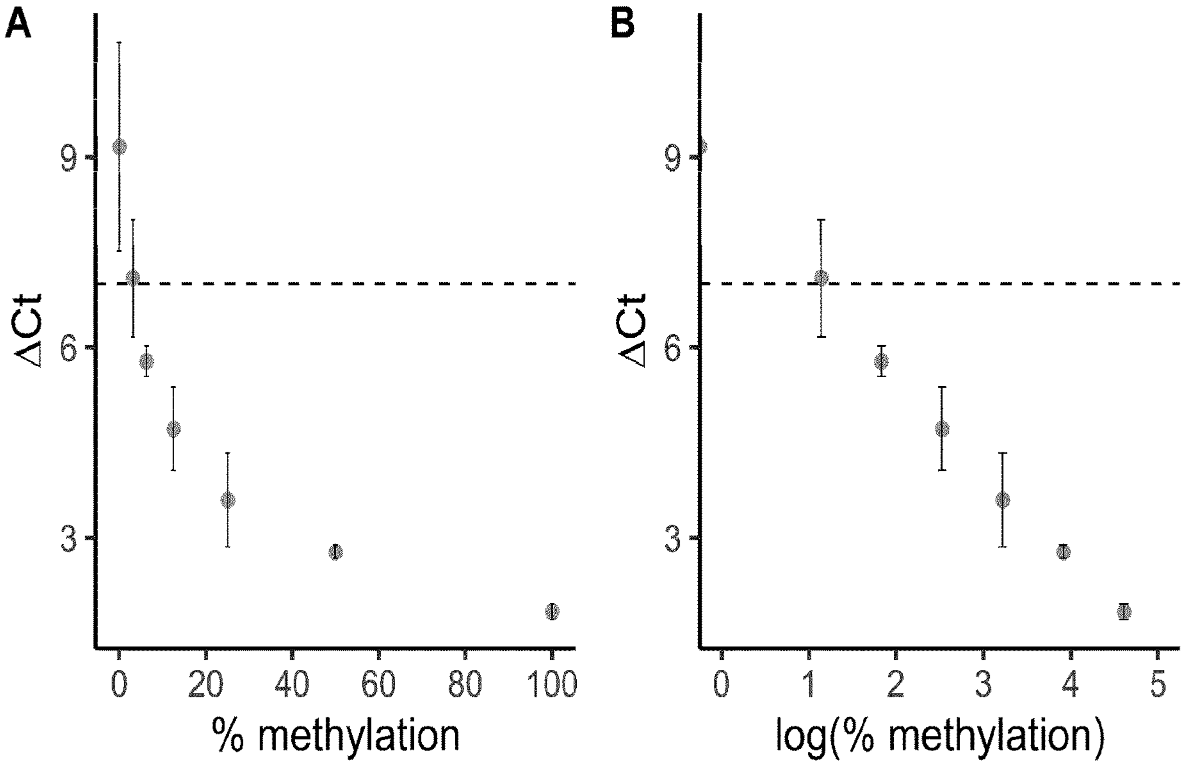

FIG. 15. Sensitivity study performed on a BaseTyper™ real-time PCR instrument using a BasePrimer with a mismatch in anchor sequence. A) The ΔCt is plotted as a function of % methylation. B) The ΔCt is plotted as a function of log (% methylation). PCR Program G (see Table 23) was used. 700 nM MGMT_Fw2C, 700 nM Rev2E and 500 nM MGMT_Probe2E were used in the reference assay, and the methyl-specific assay had 700 nM MGMT_FwLoop5D_M5 instead of MGMT_Fw2C. The template was artificial DNA from the MGMT promoter region methylated using CpG Methyltransferase (New England Biolabs Inc, Ipswich, MA, USA). Linearity is observed in B), indicating that the assay is quantitative.

Figure 16:
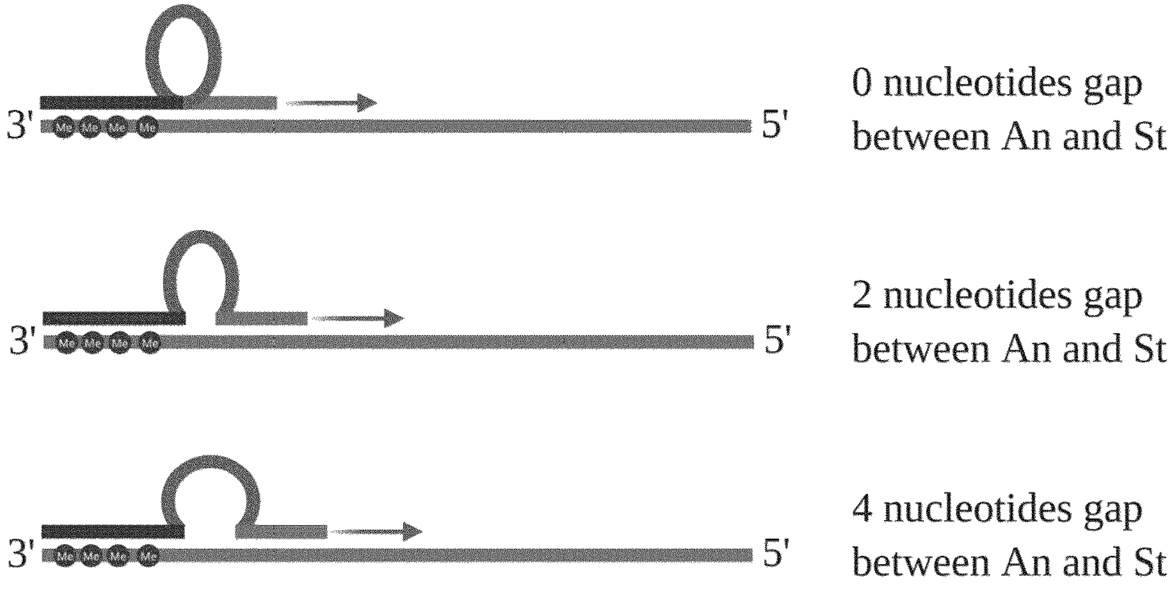

FIG. 16. BasePrimers with a gap of nucleotides between the 3'-end of the anchor sequence (An) and the 5'-end of the starter sequence (St) on the complementary target sequence. BasePrimers with gaps of 0, 2 and 4 nucleotides are illustrated (Created with BioRender.com).

Figure 17:
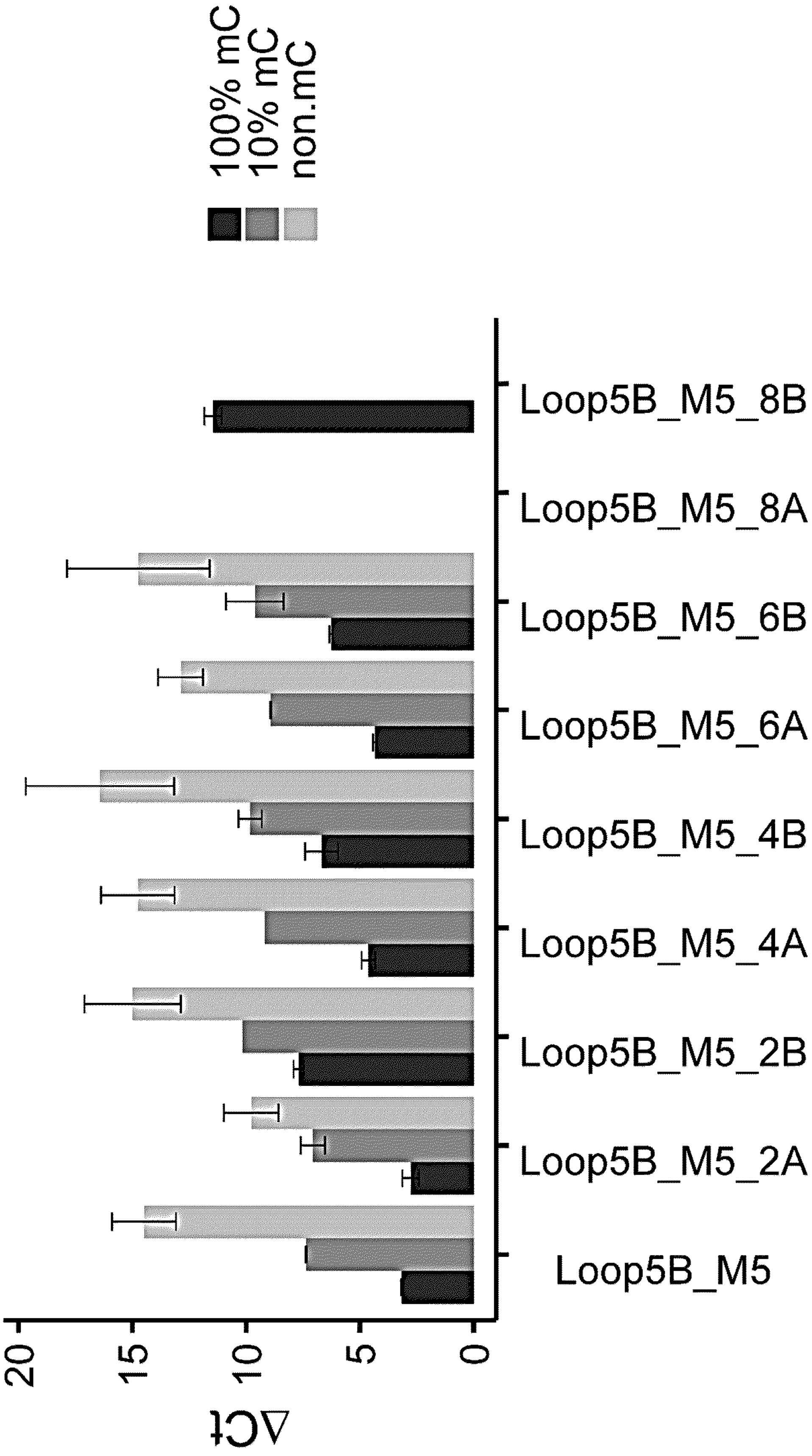

FIG. 17. Bar plot of ΔCt for BasePrimers with a mismatch in anchor sequence. The BasePrimers were designed with a gap of nucleotides between the 3'-end of the anchor sequence and the 5'-end of the starter sequence on the complementary target sequence. PCR Program H (see Table 25) was used. 700 nM MGMT_Fw2C, 700 nM MGMT_Rev2E, and 500 nM MGMT_Probe2E were used for the reference assay, and for the methyl-specific assay, 700 nM of the BasePrimers listed in Table 24 were used instead of MGMT_Fw2C. The ΔCt is plotted for 100% methylated (100% mC), 10% methylated (10% mC), and non-methylated DNA (non.mC). The template was artificial DNA from the MGMT promoter region methylated using CpG Methyltransferase (New England Biolabs Inc, Ipswich, MA, USA).

Figure 18A:
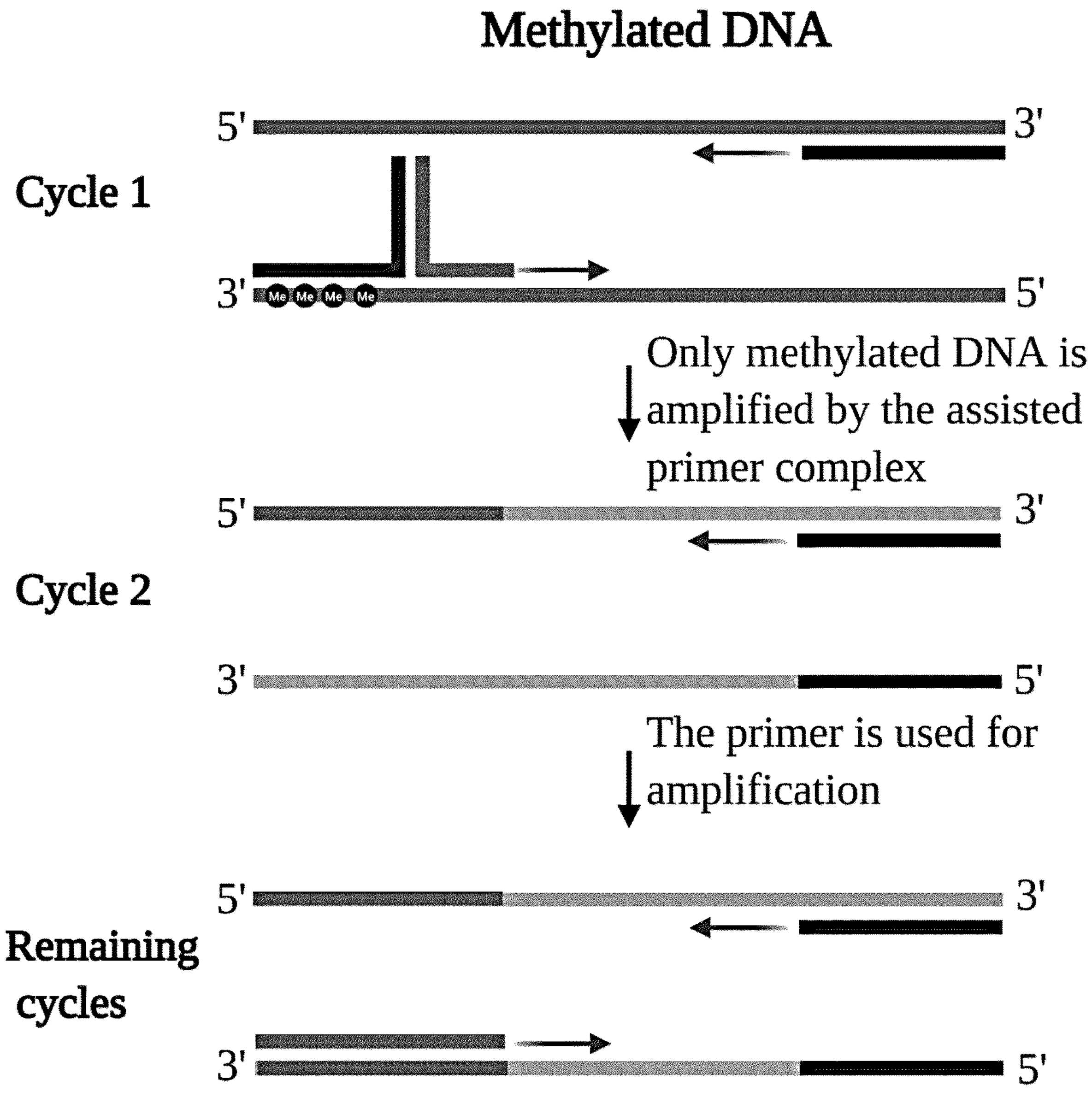
Figure 18B:
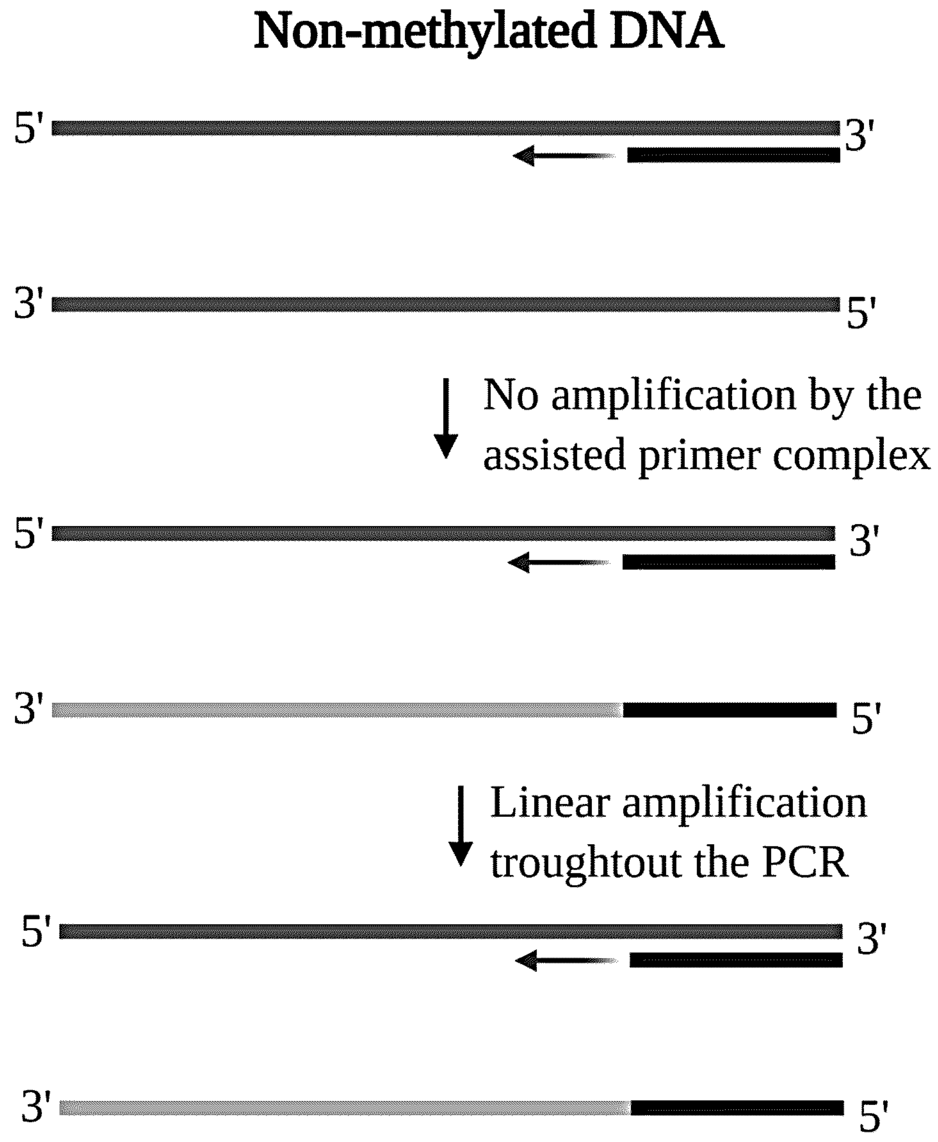

FIG. 18. Design approach of assisted primer complex. The assisted primer complex consists of two primers. One primer (dark grey) called the assist primer comprises an anchor sequence complementary to the target DNA and a stem sequence not complementary to the target sequence. The stem sequence is complementary to a sequence of the second primer. The second primer has a complementary sequence to the target DNA in the primer's 3'-end. Thereby, the two primers make a tertiary complex. A) At selected conditions, the complex will only be stable if the template DNA is methylated. The second primer of the assisted primer complex is used for the remaining PCR cycles. B) If the template DNA is not methylated, the assisted primer complex will not be stable at the selected conditions, and no amplification will occur (Created with BioRender.com).

Figure 19:
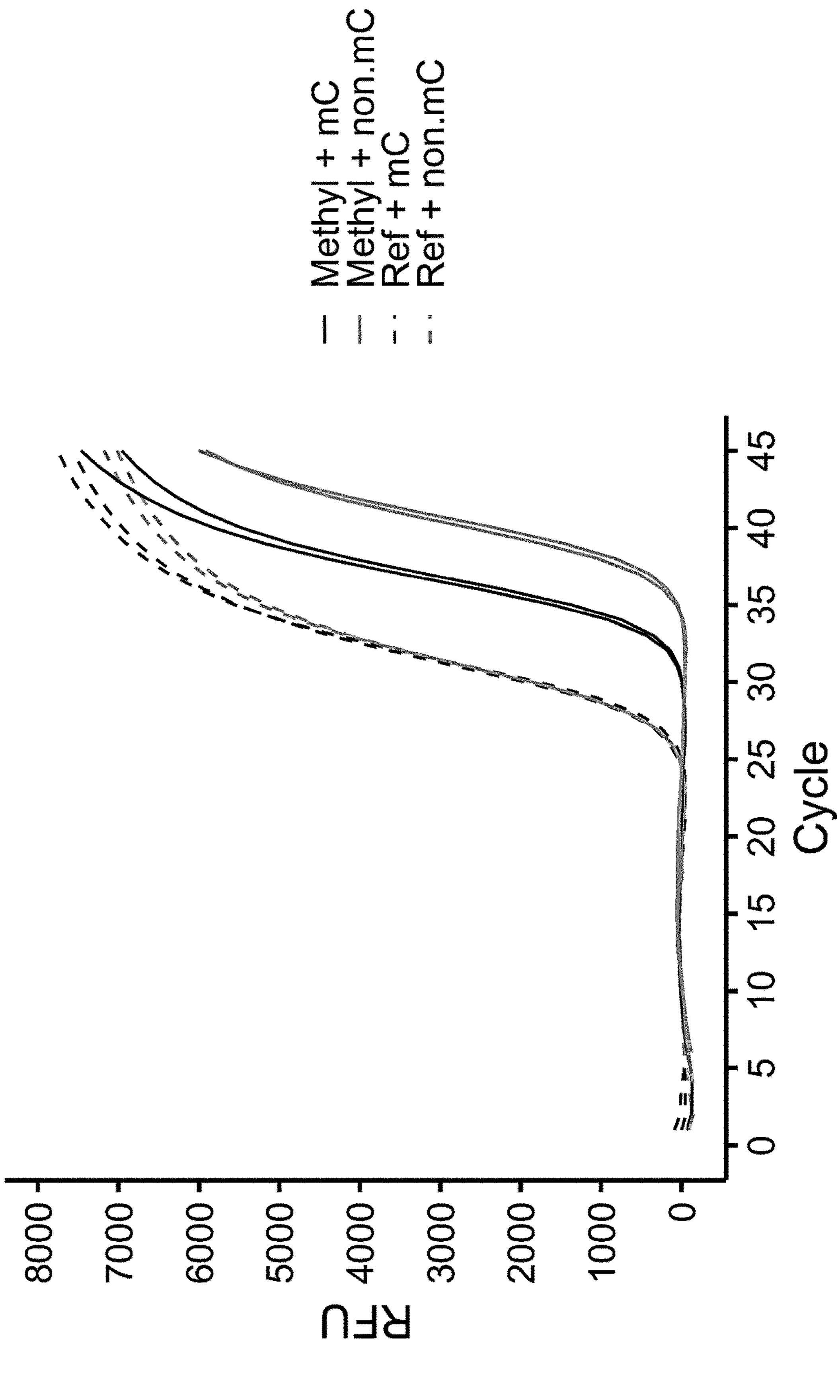

FIG. 19. PCR curves for assisted primer complex. The relative fluorescence units (RFU) are plotted as a function of cycle. PCR Program H (see Table 25) was used. 700 nM MGMT_Fw2C, 700 nM MGMT_Rev2E, and 500 nM MGMT_Probe2E were used for the reference assay, and for the methyl-specific assay, 700 nM of MGMT_Primer_1D and 50 nM of MGMT_Assist_1A_E were used instead of MGMT_Fw2C. The template was artificial DNA from the MGMT promoter region (non.mC) and the same template which was methylated using CpG Methyltransferase (New England Biolabs Inc, Ipswich, MA, USA) (mC).

DETAILED DESCRIPTION

Definitions

The term "anchor sequence" refers to a sequence comprised within an oligonucleotide, preferably within a BasePrimer. The anchor sequence comprises one or more hydrophobic nucleotides, which are positioned adjacent to the nucleotide complementary to the Nucleotide(s) Of Interest (NOI). Furthermore, the anchor sequence is capable of hybridising to a part of the target nucleic acid sequence of interest referred to as "target anchor sequence". The "anchor sequence" is abbreviated "An" herein.

The term "BasePrimer" as used herein refers to an oligonucleotide comprising or consisting of an anchor sequence (An), a loop sequence (Lp) and a starter sequence (St). BasePrimers are described in more detail herein below. Whereas the anchor sequence and the starter sequence are at least partly complementary to the target nucleic acid sequence, and thus are capable of hybridising thereto, the loop sequence is not complementary to the target nucleic acid sequence. Typically, neither the loop sequence nor the starter sequence comprises a hydrophobic nucleotide. In the event that the BasePrimer comprises a hydrophobic nucleotide in between the anchor sequence and the loop sequence, such a hydrophobic nucleotide is considered to be part of the anchor sequence. The terms "loop sequence" and "protruding sequence" are used interchangeably herein.

The term "complementary" as used herein refers to a consecutive sequence of nucleotides which are capable of base pairing with another consecutive sequence of nucleotides by Watson-Crick base pairs.

The term "hydrophobic nucleotide" as used herein refers to the hydrophobic nucleotides described in detail herein below in the section "hydrophobic nucleotide". In particular, a hydrophobic nucleotide according to the invention contains an intercalator connected to a nucleotide/nucleotide analogue/backbone monomer unit via a linker.

The term "melting temperature" as used herein denotes the temperature in degrees centigrade at which 50% hybridised versus unhybridised forms of nucleic acid sequences capable of forming a duplex are present. Melting temperature may also be referred to as ($T_m$). Melting of nucleic acids refers to thermal separation of the two strands of a double-stranded nucleic acid molecule. The melting temperature is preferably determined as described in Example 1 below. It is preferred that the melting temperature is determined in the same solution (e.g. buffer) used to conduct the methods of the invention.

The term "methylation of a nucleotide" or "methylated nucleotide" refers to that the nucleobase of said nucleotide is covalently modified with an additional methyl group compared to what is normally (in the nucleic acid without any epigenetic modifications) present in said nucleobase. Whereas different methylations are relevant in relation to the present invention, a preferred methylation is methylation of cytosine. Frequently, the methyl group is added to the 5th atom on the pyrimidine ring creating 5-methylcytosine (5-mC):

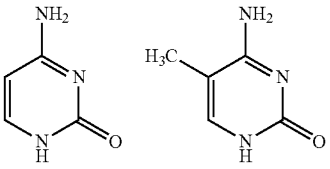

Cytosine 5-Methylcytosine

Methylation of cytosine is in particular prevalent when cytosine is located right before guanine in a CpG dinucleotide, which may also be referred to as an "CpG site". Certain regions of the genome contain a large number of CpG sites. Such regions may be referred to as "CpG islands".

The term "nucleotide" as used herein refers to nucleotides, for example naturally occurring ribonucleotides or deoxyribonucleotides or naturally occurring derivatives of ribonucleotides or deoxyribonucleotides. Nucleotides include deoxyribonucleotides comprising one of the four nucleobases adenine (A), thymine (T), guanine (G) or cytosine (C), and ribonucleotides comprising one of the four nucleobases adenine (A), uracil (U), guanine (G) or cytosine (C). For the sake of simplicity, a nucleotide comprising a particular nucleobase may herein simply be referred to by the name of said nucleobase. By way of example, a nucleotide comprising cytosine (C) may also be referred to as "cytosine" or "C".

The term "Nucleotide of Interest" as used herein refers to a nucleotide, wherein the methylation status of said nucleotide it is desirable to investigate. The nucleotide of interest may be any nucleotide, but preferably the nucleotide of interest is cytosine (C). The "nucleotide of interest" is abbreviated "NOI" herein.

The term "oligonucleotide" as used herein refers to oligomers of nucleotides and/or nucleotide analogous and/or hydrophobic nucleotides. Preferably, and oligonucleotide is an oligomer of nucleotides optionally comprising one or more hydrophobic nucleotides.

The term "Target nucleic acid sequence of interest" refers to a nucleic acid sequence comprising a "target anchor sequence", wherein said "target anchor sequence" comprises at least one NOI.

The term "Target anchor sequence" refers to the part of the target nucleic acid sequence of interest comprising the NOIs. The "anchor sequence" is capable of hybridising to the target anchor sequence.

The term "Epigenetic changes" refers to modifications that can happen naturally to the nucleobase of a nucleic acid, given that such modification changes the stacking efficiency of the nucleobase.

The term "epigenetic modification" as used herein refers to a covalent modification of a nucleobase, which typically is inherited to daughter cells. Said epigenetic modification is preferably a methylation, however it could also be alkylation, acetylation, hydroxylation, methoxylation or other modifications of the nucleobases.

The term "non-modified" as used herein refers to that a nucleic acid of interest has not undergone a step of modification or pre-treatment to convert unmethylated nucleotides to detectable moieties and/or to convert methylated nucleotides to detectable moieties. Examples of such modifications or pre-treatments include bisulfite conversion, restriction enzyme digestion or TET enzymatic conversion. Non-modified as defined herein thus only refers to the absence of nucleic acid treatments or modifications that act selectively on either methylated or unmethylated nucleic acids. Pre-treatment steps or modifications that are not able to selectively act on or discern between either methylated or unmethylated nucleic acids, such as dilution, DNA purification or enzymatic treatment that does not discern between methylated and unmethylated nucleic acids, are not covered by the term as used herein.

Methylation Status of Nucleotide of Interest in a Target Nucleic Acid Sequence The present invention relates to methods of determining the epigenetic (such as methylation) status of at least one NOI in a target nucleic acid sequence.

The methods are based on use of oligonucleotides comprising an anchor sequence, said anchor sequence comprising one or more hydrophobic nucleotides. The oligonucleotide may be any of the oligonucleotides described herein below in the section "Oligonucleotide comprising anchor sequence". The oligonucleotides comprising an anchor sequence have significantly different affinity for the nucleic acid sequence with said epigenetic modification (e.g. methylation), than for nucleic acid sequences without said epigenetic modifications. For example, the oligonucleotides comprising an anchor sequence have significantly higher affinity for methylated compared to unmethylated nucleic acids. This difference in affinity can be used to detect epigenetic modifications such as methylation in various manners as described below.

Thus, the methods of the invention in general comprises a step b) of incubating said oligonucleotide with the target nucleic acid of interest at a temperature which is higher than the melting temperature between said oligonucleotide and the target nucleic acid sequence of interest when said NOI has an epigenetic modification pattern different from the pattern that is investigated.

Preferably, said temperature is selected so that the temperature is higher than the melting temperature between said oligonucleotide and the target nucleic acid sequence of interest when said NOI is unmethylated, and said temperature is max. 2° C. higher, equal to or lower than the melting temperature between said oligonucleotide and the target nucleic acid sequence of interest when said NOI is methylated.

In some embodiments, said temperature is selected so that the temperature is at least 2° C. higher than the melting temperature between said oligonucleotide and the target nucleic acid sequence of interest when said NOI is unmethylated, and said temperature is max. 2° C. higher, equal to or lower than the melting temperature between said oligonucleotide and the target nucleic acid sequence of interest when said NOI is methylated.

As noted herein elsewhere, at the melting temperature approx. 50% hybridised versus unhybridised forms are present. Thus, at temperatures higher than the melting temperature some hybridisation will typically still occur. Thus, a temperature slightly higher than the melting temperature, e.g. up to 2° C. higher can be used.

The difference in affinity, and hence epigenetic status such as methylation may be detected using various different methods. Very simply, the melting temperature between the oligonucleotide comprising an anchor sequence and the target nucleic acid sequence may be determined, and the epigenetic status can be determined on this basis.

Preferably, the methods comprise an amplification step, wherein said amplification is designed in a manner so that amplification only takes place when the NOI is methylated or alternatively that amplification only takes place when the NOI is not methylated. This can be achieved by designing an assay comprising one or more steps using a temperature allowing annealing of the oligonucleotide comprising anchor sequence to the methylated target nucleic acid, but which does not allow annealing of said oligonucleotide to unmethylated target sequence.

Preferred methods are PCR based methods and in particular any of the PCR based methods described herein below in the section "PCR".

As explained herein above one advantage of the methods of the invention is that the methods do not require a pre-treatment of the target nucleic acid to convert unmethylated or methylated nucleotides to detectable moieties, such as bisulfite conversion, restriction enzyme digestion or TET enzymatic conversion.

Bisulfite converts unmethylated cytosine to uracil. 5-methylcytosine remains unchanged. This creates a difference in the base pair sequence depending on the methylation status, allowing detection of differences between methylated and non-methylated DNA, such as by PCR.

Methylation-sensitive restriction enzymes can also be used to determine the methylation status of a sample. Usually, a methylation sensitive restriction enzyme is together with a methylation insensitive isoschizomer. An example of such set of enzymes is HpaII and MspI both enzymes recognizing the sequence CCGG and cutting before the CG dinucleotide. HpaII does only cleave non-methylated CCGG and MspI cleaves both methylated and non-methylated CCGG sites. Thereby, it is possible to detect a difference in digestion of methylated and non-methylated DNA, which can be analyzed by PCR.

TET enzymatic conversion relies on two types of enzymes, APOBEC and TET2. TET2 converts 5-methylcytosine to 5-carboxycytosine. This conversion protects 5-methylcytosine from being converted by APOBEC, which then only deaminates unmethylated cytosine to uracil, allowing detection of differences between methylated and non-methylated DNA, such as by PCR.

In some embodiments, the target nucleic acid sequence of interest is non-modified. It is thus comprised within the invention, that the methods do not comprise a step of pre-treatment of nucleic acid of interest to convert unmethylated nucleotides to detectable moieties and/or to convert methylated nucleotides to detectable moieties. In some embodiments, the target nucleic acid sequence of interest has not been subjected to treatment comprising bisulfite conversion, restriction enzyme digestion or TET enzymatic conversion prior to performing the method as disclosed herein. In particular, it is preferred that the methods do not comprise a step of bisulfite conversion.

Target Nucleic Acid Sequence

The target nucleic acid sequence may be any nucleic acid sequence comprising at least one nucleotide (NOI) of which the epigenetic such as the methylation status is desirable to determine. The target nucleic acid sequence is typically a longer nucleic acid sequence comprising a shorter sequence of interest, which herein is denoted "target anchor sequence". The target anchor sequence comprises said at least one NOI.

Preferably, the nucleic acid is DNA, however the nucleic acid may also be other kinds of nucleic acids, such as RNA. In preferred embodiments, the nucleic acid is genomic DNA. The present methods can advantageously be used to determine epigenetic modifications, in particular methylation of cytosines, of naturally occurring sequences.

Preferably, the epigenetic modification is a methylation, however it could also be alkylation, acetylation, hydroxylation, methoxylation or other modifications of the nucleobases.

The target anchor sequence comprises one or more NOIs. The anchor sequence of the oligonucleotides of the invention is selected in a manner, so that the anchor sequence can hybridise with the target anchor sequence. Typically, the anchor sequence is at least 50% complementary to the target anchor sequence.

Frequently, several NOIs which may or may not be modified, such as methylated are located in close proximity within the target nucleic acid sequence. In such cases, it may be desirable to determine an overall modification (methylation) status of all of said nucleotides. This may be done by the methods of the invention as described below, by using an oligonucleotide with an anchor sequence comprising one hydrophobic nucleotide per NOI. It is also comprised within the invention that only the modification (methylation) status of one or a few of said NOIs is determined. Again, this may be done by employing an oligonucleotide with an anchor sequence comprising one hydrophobic nucleotide per NOI to be investigated.

In some embodiments, the target nucleic acid sequence may be a nucleic acid sequence comprising one or more NOIs of which the epigenetic modification status is associated with a clinical condition. For example, the methylation status of said NOI may be associated with the presence of a clinical condition, the advancement of a clinical condition, the risk of acquiring a clinical condition, or the susceptibility to a certain method of treatment as described in more detail below in the section "Clinical condition". That methylation status of an NOI is "associated with" a clinical condition does not imply that it is causative of said clinical condition, but rather that a given methylation status is more prevalent in relation to said clinical condition.

The NOI may be any nucleotide where the epigenetic modification status is desirable to detect. In preferred embodiments the NOI is cytosine (C), and even more preferably the NOI is a cytosine positioned in a CpG site. In the most preferred embodiment, the epigenetic modification of NOIs is a methylation of a CpG site.

The target nucleic acid may be comprised in any composition comprising said target nucleic acid sequence. Frequently, the target nucleic acid is comprised within a nucleic acid sample. Said sample may have been obtained from any source in which it is desirable to determine the epigenetic status (e.g. methylations status). For example, the sample may be obtained from a mammal, such as a human being. The sample may be at least partly purified, i.e. the sample may comprise at least partly purified nucleic acids. Thus, the target nucleic acid sequence of interest may be comprised in DNA purified from a sample.

As described herein elsewhere the target anchor sequence is at least partly complementary to the anchor sequence. Thus, if the target nucleic acid is a double stranded nucleic acid, such as DNA, the anchor sequence is usually at least partly identical to one strand of the DNA, and the target anchor sequence is positioned in the other strand of said DNA.

Oligonucleotide Comprising Anchor Sequence

The invention relates to methods for determining epigenetic such as the methylation status of at least one NOI, said methods employing use of an oligonucleotide comprising an anchor sequence (An), wherein the anchor sequence is a sequence at least 50% complementary to a section within the target nucleic acid sequence comprising the NOI herein denoted "target anchor sequence". The anchor sequence preferably comprises at least one hydrophobic nucleotide (H) positioned between the nucleotide complementary to said NOI and the nucleotide in the oligonucleotide immediately 5' thereof.

In embodiments of the invention where the NOI is C, the anchor sequence accordingly preferably comprises the sequence-H-G-, wherein said G is complementary to the C of interest.

It is preferred that the anchor sequence does not comprise two neighboring hydrophobic nucleotides. Accordingly, the anchor sequence may in particular comprise the sequence -N-H-G-, wherein N may be any nucleotide, and the sequence-N-G- is complementary to the cytosine of interest and its neighbouring nucleotide. In particular, N may be selected from the group consisting of C, G, A and T.

In embodiments where the NOI is a C located in a CpG site, it is preferred that the anchor sequence comprises the sequence -C-H-G-.

The anchor sequence may comprise more than one hydrophobic nucleotide. Thus, the anchor sequence may comprise at least 2, such as at least 3, for example at least 4, such as in the range of 1 to 10, for example in the range of 2 to 10, such as in the range of 3 to 10, for example in the range of 4 to 10 hydrophobic nucleotides (H).

The anchor sequence may in particular comprise one hydrophobic nucleotide per NOI. Said hydrophobic nucleotides are preferably all positioned between a nucleotide complementary to a NOI and the nucleotide in the oligonucleotide immediately 5' thereof. In addition, the anchor sequence may also comprise additional hydrophobic nucleotides.

In embodiments of the invention, wherein the target nucleic acid sequence comprises more than one NOI, which is C, the anchor sequence may thus comprise more than one -N-H-G- sequences, wherein each N individually may be any nucleotide. Preferably, said anchor sequence comprises one -N-H-G- sequence per NOI, which is C, wherein each -N-G- sequence is complementary to a cytosine of interest and its neighbouring nucleotide. Thus, the anchor sequence may comprise at least 2, such as at least 3, for example at least 4, such as in the range of 2 to 5, for example in the range of 3 to 5, such as in the range of 4 to 5-N-H-G-sequences, wherein each N individually is any nucleotide, and each sequence-N-G- is complementary to a cytosine of interest and its neighbouring nucleotide. In particular, N may be selected from the group consisting of C, G, A and T.

In embodiments of the invention, wherein the target nucleic acid sequence comprises more than one NOI, which is a C positioned in a CpG site, the anchor sequence may thus comprise one -C-H-G- sequence per NOI, which is a C positioned in a CpG site. Thus, the anchor sequence may comprise at least 2, such as at least 3, for example at least 4, such as in the range of 2 to 5, for example in the range of 3 to 5, such as in the range of 4 to 5-C-H-G- sequences.

In one embodiment the oligonucleotide comprises an anchor sequence consisting of the following general structure:

$$5'(N)_n—HG—(N)_m—HG—(N)_p\text{-}3',$$

wherein N is any nucleotide or nucleotide analogue; and
G is the nucleotide guanine; and
n is an integer ≥0; and
m is an integer ≥1; and
p is an integer ≥0; and
H is a hydrophobic nucleotide, e.g. any of the hydrophobic nucleotides described below.

In one embodiment the oligonucleotide comprises an anchor sequence consisting of the following general structure:

$$5'(N)_n—HG—(N)_m—HG—(N)_p—HG—(N)_q\text{-}3',$$

wherein
p is ≥1; and
q is an integer ≥0.

In one embodiment the oligonucleotide comprises an anchor sequence consisting of the following general structure:

$$5'(N)_n—YG—(N)_m—YG—(N)_p—YG—(N)_q—YG—(N)_u\text{-}3',$$

wherein
q is an integer ≥1; and
u is an integer ≥0.

Y denotes a C or a T according to the extended IUPAC code.

In relation to the oligonucleotides described above, n may for example be an integer in the range of 0 to 4, for example n may be 1, m may for example be an integer in the range of 1 to 8, for example in the range of 1 to 6, p may for example be an integer in the range of 1 to 50, such as in the range of 1 to 30, for example in the range of 1 to 10, for example in the range of 1 to 6, q may for example be is an integer in the range of 1 to 50, such as in the range of 1 to 30, for example in the range of 1 to 10, for example in the range of 1 to 6, and u may for example be an integer in the range of 1 to 50, such as in the range of 1 to 30, for example in the range of 1 to 10, for example in the range of 1 to 6.

In preferred embodiments of the invention the oligonucleotide is a BasePrimer as described below. In such embodiments the anchor sequence is linked to a loop sequence and a starter sequence, and in such embodiments the 3' part of the oligonucleotide is sufficiently long to contain both a loop sequence and a starter sequence.

As explained above, the NOI may be a cytosine positioned in a CpG site. In such cases it is preferred that the nucleotide located immediately 5' to at least one H is a cytosine (C). If all NOIs are cytosines positioned in CpG sites it is preferred that all nucleotides located immediately 5' to a H is a cytosine (C), when said H is adjacent to a G complementary to a NOI.

The oligonucleotide comprising the anchor sequence anneals to the methylated target nucleic acid sequence with higher affinity than to the unmethylated target nucleic acid sequence. Thus, the melting temperature between said oligonucleotide and the methylated target nucleic acid sequence of interest is often at least 5° C. higher, for example at least 6° C. higher, such as in the range of 6 to 15° C. higher, for example in the range of 6 to 12° C. higher than the melting temperature between said oligonucleotide and the unmethylated target nucleic acid sequence of interest.

In particular, the invention is based on the finding that the oligonucleotides described herein have a larger difference in affinity to methylated versus unmethylated target nucleic acid compared similar oligonucleotides not comprising hydrophobic nucleotides. This larger difference in affinity allows for successful detection of methylation by simple methods, such as PCR. The difference in melting temperature between the oligonucleotide of the invention and the methylated target nucleic acid sequence compared to an unmethylated target nucleic acid sequence of interest is preferably at least 1° C. higher than the difference in melting temperature between an oligonucleotide of identical sequence except lacking the hydrophobic nucleotides and the methylated target nucleic acid sequence compared to an unmethylated target nucleic acid sequence.

NOI methylation, such as cytosine methylation, i.e. the presence of methylated cytosine(s) in a nucleic acid, such as a target nucleic acid of interest, results in a difference in melting temperature when said nucleic acid is hybridized to an oligonucleotide. Said difference is dependent on the number of methylated NOIs and can be difficult to detect. The hydrophobic nucleotide of the oligonucleotide of the invention amplifies the difference in affinity for unmethylated vs. methylated NOIs compared to an oligonucleotide otherwise identical but not comprising a hydrophobic nucleotide. The oligonucleotide of the invention thus provides a larger difference in melting temperature when hybridized to a target sequence of interest depending on the number of methylated NOIs, such as methylated cytosines, compared to an identical oligonucleotide not comprising said hydrophobic nucleotide, thus facilitating detection of the presence of methylated NOIs.

In some embodiments, the difference between

A. the absolute difference between the melting temperatures of
   i. the oligonucleotide of the present invention comprising said hydrophobic nucleotide(s) when hybridized to said target nucleic acid sequence of interest, wherein said nucleic acid sequence of interest comprises at least one methylated NOI, such as at least one methylated cytosine; and
   ii. the oligonucleotide of the present invention comprising said hydrophobic nucleotide(s) when hybridized to said target nucleic acid sequence of interest, wherein said nucleic acid sequence of interest comprises no methylated NOIs, such as no methylated cytosines; and
B. the absolute difference between the melting temperatures of
   i. an oligonucleotide identical to the oligonucleotide of A., however which does not comprise said hydrophobic nucleotide(s), when hybridized to said target nucleic acid sequence of interest, wherein said nucleic acid sequence of interest comprises the same number of methylated NOIs as in A. i., such as the same number of methylated cytosines as in A. i.; and
   ii. an oligonucleotide identical to the oligonucleotide of A., however which does not comprise said hydrophobic nucleotide(s), when hybridized to said target nucleic acid sequence of interest, wherein said nucleic acid sequence of interest comprises no methylated NOIs, such as no methylated cytosines, of at least 0.50° C., such as at least 0.75° C., preferably at least 1.0° C. per NOI, such as per cytosine, that is methylated instead of unmethylated in said target nucleic acid sequence of interest, wherein the difference is A-B and, wherein the difference is a positive difference. In preferred embodiments, the melting temperature is measured in TM buffer comprising 0.02 M $Na_2HPO_4$, 0.02 M NaCl, and 2 mM EDTA.

In some embodiments, the absolute difference between the melting temperatures of i. the oligonucleotide of the present invention comprising said hydrophobic nucleotide when hybridized to said target nucleic acid sequence of interest, wherein said nucleic acid sequence of interest comprises at least one methylated NOI, such as at least one methylated cytosine; and
ii. the oligonucleotide of the present invention comprising said hydrophobic nucleotide when hybridized to said target nucleic acid sequence of interest, wherein said nucleic acid sequence of interest comprises no methylated NOIs, such as no methylated cytosines;

is at least 1.6° C., such as at least 1.8° C., such as at least 2.0° C., such as at least 2.2° C., preferably at least 2.4° C. per NOI, such as per cytosine, that is methylated instead of unmethylated in said target nucleic acid sequence of interest. In preferred embodiments, the melting temperature is measured in TM buffer comprising 0.02 M $Na_2HPO_4$, 0.02 M NaCl, and 2 mM EDTA.

For comparison, in some embodiments, the absolute difference between the melting temperatures of i. an oligonucleotide identical to the oligonucleotide described in the paragraph above, however which does not comprise said hydrophobic nucleotide, when hybridized to said target nucleic acid sequence of interest, wherein said nucleic acid sequence of interest comprises at least one methylated NOI, such as at least one methylated cytosine; and
ii. an oligonucleotide identical to the to the oligonucleotide described in the paragraph above, however which does not comprise said hydrophobic nucleotide, when hybridized to said target nucleic acid sequence of interest, wherein said nucleic acid sequence of interest comprises no methylated NOIs, such as no methylated cytosines; and is at the most 1.0° C., such as at the most 0.9° C., such as at the most 0.8° C. per NOI, such as per cytosine, that is methylated instead of unmethylated in said target nucleic acid sequence of interest. In preferred embodiments, the melting temperature is measured in TM buffer comprising 0.02 M $Na_2HPO_4$, 0.02 M NaCl, and 2 mM EDTA.

Preferably, the anchor sequence (An) consists of the in range of 8 to 30, for example in the range of 8 to 20, such as in the range of 10 to 20, for example in the range of 15 to 20 nucleotides, wherein one or more of said nucleotides are hydrophobic nucleotide(s).

As noted, the anchor sequence (An) is at least 50% complementary to the target anchor sequence, preferably the anchor sequence (An) is at least 85% complementary to the target anchor sequence. In some embodiments the anchor sequence may be 100% complementary to the target anchor sequence. However, in preferred embodiments, the anchor sequence is not 100% complementary to the target anchor sequence.

BasePrimer

The invention relates to methods for determining the epigenetic status such as the methylation status of at least one NOI, said methods employing use of an oligonucleotide comprising an anchor sequence (An). In preferred embodiments said oligonucleotide is a BasePrimer as described in this section.

A BasePrimer according to the present invention is an oligonucleotide having the structure $$5'\text{—An—Lp—St-}3', \quad \text{wherein}$$

An is an anchor sequence;
Lp is a loop sequence; and
St is a starter sequence.

The anchor sequence (An) is preferably a sequence at least 50% complementary to a section within the target nucleic acid sequence comprising the NOI herein denoted "target anchor sequence". The anchor sequence preferably comprises at least one hydrophobic nucleotide (H) positioned between the nucleotide complementary to said NOI and the nucleotide in the oligonucleotide immediately 5' thereof. The anchor sequence may in particular be any of the anchor sequences described herein above in the section "Oligonucleotide comprising anchor sequence".

The loop sequence (Lp) is a sequence, which does not hybridise to any significant extent to the target nucleic acid sequence. Thus, preferably Lp is not complementary to the nucleic acid sequence of interest. The loop sequence may consist of a single nucleic acid sequence capable of forming a protruding structure, or it may consist of two or more nucleic acid sequences capable of hybridising at least partly to one another to form a complex which is capable of forming a protruding structure. In some embodiments, the protruding structure is a loop structure. In some embodiments, the protruding structure is a stem structure.

In some embodiments, the oligonucleotide of the invention may thus consist of a first and a second nucleic acid sequences, wherein the first nucleic acid sequence comprises the anchor sequence (An) complementary to the target DNA and a first part of a loop sequence not complementary to the target nucleic sequence of interest, and the second nucleic acid sequence comprises a second part of the loop sequence, capable of hybridising at least partly to the first part of the loop sequence, said second nucleic acid sequence further comprising the starter sequence (St). Once hybridized, the first and the second nucleic acids are capable of forming the protruding structure, such as a stem structure.

In some embodiments, the oligonucleotide of the invention may consist of a first, a second and a third nucleic acid sequences, wherein the first nucleic acid sequence comprises the anchor sequence (An) complementary to the target DNA and a first part of a loop sequence not complementary to the target nucleic sequence of interest, the second nucleic acid sequence comprises a second part of the loop sequence, capable of hybridising at least partly to the first part of the loop sequence, said second nucleic acid sequence further comprising the starter sequence (St), and said third nucleic acid sequence is capable of hybridizing at a first region to a part of the 3' end of the first oligonucleotide, and at a second region to a part of the 5' end of the second oligonucleotide. Once hybridized, the first, the second and the third nucleic acids are capable of forming the protruding structure, such as a loop structure.

In some embodiments, the oligonucleotide of the invention is encoded as a single oligonucleotide. In some embodiments, the oligonucleotide of the invention is encoded as two or more separate oligonucleotides.

The starter sequence (St) is a sequence, which can hybridise to the target nucleic acid sequence, but which does so with low affinity. Thus, under the conditions used for the methods of the invention, starter sequence preferably does not anneal to the target nucleic acid sequence unless the anchor sequence also anneals. The starter sequence (St) may preferably be capable of being elongated, thus the starter sequence should be able to serve as a primer. Thus, the starter sequence is preferably at least 90% complementary to a section of the target nucleic acid sequence, which herein is denoted "target starter sequence".

The target starter sequence is a sequence of the target nucleic acid sequence, which is positioned 5' to the target anchor sequence. The target starter sequence may be positioned immediately 5' to the target anchor sequence, however, there may also be a space between said sequences. Thus, the target starter sequence may be separated from the target anchor sequence by in the range of 1 to 20 nucleotides, such as in the range of 2 to 10 nucleotides, for example in the range of 2 to 5 nucleotides.

As noted above the starter sequence is at least 90% complementary to the target starter sequence, but it may also be 100% complementary to target starter sequence.

The BasePrimer is particularly useful for PCR based methods, wherein the BasePrimer is one primer of a primer pair, which can be used for amplification of the target nucleic acid sequence. Based on the design of the anchor sequence, the anchor sequence will anneal with high affinity to the methylated target nucleic acid sequence, which allows for annealing of the starter sequence as well. After annealing the BasePrimer can be elongated using a polymerase, such as by any DNA polymerase conventionally used for PCR. The first reverse transcription will typically end, when the polymerase encounters the first hydrophobic nucleotide at the product will thus lack at least part of the anchor sequence. However, the next round of PCR will still be able to use the BasePrimer as primer, because the loop sequence and the starter sequence can anneal to the product of the first round of amplification.

Since the polymerase usually stops elongation at the position, where a template comprises a hydrophobic nucleotide, it may be preferred that the BasePrimer comprises a hydrophobic nucleotide between the anchor sequence and the loop sequence. Such as hydrophobic nucleotide is considered to be part of the anchor sequence.

Accordingly, it is also preferred that neither the starter sequence nor the loop sequence comprise a hydrophobic nucleotide. However, if the loop sequence consists of two or more nucleic acid sequences, the nucleic acid sequence(s) not covalently linked to the starter sequence may comprise one or more hydrophobic nucleotides.

The loop sequence and starter sequence serve as primer for the rounds after the first amplification from the target. Thus, the loop sequence and the starter sequence together (-Lp-St-) should be designed in a manner allowing them to function as a primer. Thus, it is preferred that an oligonucleotide consisting of Lp-St would have a melting temperature to its complementary sequence of at least 50° C., for example at least 55° C., such as at least 65° C. In general, it is preferred that the loop sequence and the starter sequence together consists of at least 15 nucleotides, for example at least 17 nucleotides, such as in the range of 15 to 45 nucleotide, for example in the range of 17 to 35 nucleotides, such as in the range of 17 to 25 nucleotides.

As noted above, the starter sequence should anneal to the target nucleic acid sequence with low affinity. Thus, it is preferred that the starter sequence is not too long. Preferably, the starter sequence consists of in the range of 5 to 15, such as in the range of 8 to 14, such as in the range of 10 to 12 nucleotides.

The BasePrimer may comprise additional moieties in addition to the anchor, loop and starter sequences. For example, the BasePrimer may be linked to a detectable label. However, in preferred embodiments the BasePrimer consists of the anchor, loop and starter sequences.

Other Oligonucleotides

Whereas preferred oligonucleotides according to the invention are described above, the invention in one embodiment also provides oligonucleotides, which have similar affinity to methylated and unmethylated target nucleic acid sequences, e.g. a difference in $T_m$ of at the most 3° C., such as at the most 2° C. When the NOI is a cytosine positioned in a CpG site, such oligonucleotides may comprise or consist of the following general structure:

$$5'(N)_n—CGH—(N)_m—CGH—(N)_p\text{-}3',$$

wherein N is any nucleotide or nucleotide analogue; and
C is the nucleotide cytosine; and
G is the nucleotide guanine; and
n is an integer ≥0; and
m is an integer ≥1; and
p is an integer ≥0; and
H is a hydrophobic nucleotide
wherein said hydrophobic nucleotide has the structure $$X—Y—Q$$

wherein
X, Q and Y may be as described herein in the section "Hydrophobic nucleotide".

The oligonucleotide may in particular have the following general structure:

$$5'(N)_n—CGH—(N)_m—CGH—(N)_p—CGH—(N)_q\text{-}3',$$

wherein
p is ≥1; and
q is an integer ≥0.

In one embodiment such oligonucleotides comprises or consists of the following general structure:

$$5'(N)_n—CGH—(N)_m—CGH—(N)_p—CGH—(N)_q—CGH—(N)_u\text{-}3',$$

wherein
q is an integer ≥1; and
u is an integer ≥0.

n, m, p, q and u may for example be as described herein above in the section "Oligonucleotide comprising anchor sequence".

Hydrophobic Nucleotide

The oligonucleotides to be used with the present invention comprises one or more hydrophobic nucleotides. A hydrophobic nucleotide according to the present invention has the following structure:

$$X—Y—Q$$

wherein
- X is a nucleotide or nucleotide analogue or a backbone monomer unit capable of being incorporated into the backbone of a nucleic acid,
- Q is an intercalator, which is not taking part in Watson-Crick hydrogen bonding; and
- Y is a linker moiety linking said nucleotide or nucleotide analogue or backbone monomer unit and said intercalator.

The intercalator Q may be any intercalator. The term intercalator according to the present invention covers any molecular moiety comprising at least one essentially flat conjugated system, which is capable of co-stacking with nucleobases of a nucleic acid. Preferably an intercalator according to the present invention essentially consists of at least one essentially flat conjugated system, which is capable of co-stacking with nucleobases of a nucleic acid.

An intercalator comprises at least one π (phi) electron system, which according to the present invention can interact with other molecules comprising a π electron system. These interactions can contribute in a positive or negative manner to the hydrophobic interactions of said intercalators. Hunter and Sanders (1990) J. Am Chem. Soc. 112:5525-5534, have proposed a range of different orientations and conditions where two IT electron systems can interact positively with each other.

The intercalator may be any of the intercalators described in international patent application WO 2017/045689 in the section "Intercalator" on p. 30, I. 26 to p. 40, I. 3. For example the intercalator may have any of the structures depicted on p. 32-39 of said international patent application WO 2017/045689, the content of which is hereby incorporated by reference.

In one embodiment at least one, such as all intercalators, Q, are selected from the group consisting of polyaromates and heteropolyaromates optionally substituted with one or more selected from the group consisting of hydroxyl, bromo, fluoro, chloro, iodo, mercapto, thio, cyano, alkylthio, heterocycle, aryl, heteroaryl, carboxyl, carboalkoyl, alkyl, alkenyl, alkynyl, nitro, amino, alkoxyl and amido. Said polyaromates or heteropolyaromates may consist of at least 3 rings, for example 4 rings.

The intercalators may for example be selected from the group consisting of benzene, pentalene, indene, naphthalene, azulene, as-indacene, s-indacene, biphenylene, acenaphthylene, Phenalene, heptalene, phenanthrane, fluoranthene, phenanthroline, phenazine, phenanthridine, anthraquinone, pyrene, anthracene, napthene, phenanthrene, flurene, picene, chrysene, naphtacene, acridones, benzanthracenes, stilbenes, oxalo-pyridocarbazoles, azidobenzenes, porphyrins and psoralens and derivatives thereof thereof.

In one embodiment, at least one, such as all intercalators, Q are comprising or consisting of pyrene or pyrido[3',2':4,5]thieno[3,2-d]pyrimidin-4 (1H)-one or 7,9-dimethyl-pyrido[3',2',4,5]thieno[3,2-d]pyrimidin-4 (3H)-one. In particular, at least one, such as all intercalators may be pyrene.

The backbone monomer unit of a nucleotide or a nucleotide analogue according to the present invention is the part of the nucleotide, which is involved in incorporation into the backbone of a nucleic acid or a nucleic acid analogue. The backbone monomer unit (X) is preferably covalently linked to a linker (Y), which is covalently linked to the intercalator. Any suitable backbone monomer unit may be employed for incorporating intercalator into the oligonucleotide analogues according to the present invention.

The backbone monomer unit may be any of the backbone monomer units described in international patent application WO 2017/045689 in the section "Backbone monomer unit" on p. 40, I. 5 to p. 56, I. 3. The backbone monomer unit may also be any of the backbone monomer units described in international patent application WO03/052132 in the section "Backbone monomer unit" on p. 24, I. 27-p. 43, I. 14.

In a particularly preferred embodiment of the present invention, the hydrophobic nucleotide comprises a backbone monomer unit that comprises a phosphoramidite and more preferably the backbone monomer unit comprises a trivalent phosphoramidite or a pentavalent.

Suitable trivalent phosphoramidites are trivalent or pentavalent phosphoramidites that may be incorporated into the backbone of a nucleic acid and/or a nucleic acid analogue. Usually, the amidite group per se may not be incorporated into the backbone of a nucleic acid, but rather the amidite group or part of the amidite group may serve as a leaving group and/or protecting group. However, it is preferred that the backbone monomer unit comprises a phosphoramidite group, because such a group may facilitate the incorporation of the backbone monomer unit into a nucleic acid backbone.

The linker of an intercalator nucleotide according to the present invention is a moiety connecting the intercalator and the backbone monomer of said hydrophobic nucleotide, preferably covalently linking said intercalator and the backbone monomer unit. The linker may comprise one or more atom(s) or bond(s) between atoms.

By the definitions of backbone and intercalator defined herein above, the linker is the shortest path linking the backbone and the intercalators. If the intercalator is linked directly to the backbone, the linker is a bond.

The linker usually consists of a chain of atoms or a branched chain of atoms. Chains can be saturated as well as unsaturated. The linker may also be a ring structure with or without conjugated bonds.

For example the linker may comprise a chain of atoms selected from the group consisting of C, O, S, N. P, Se, Si, Ge, Sn and Pb, preferably from the group consisting of C, O, S, N and P, even more preferably they are C, wherein one end of the chain is connected to the intercalator and the other end of the chain is connected to the backbone monomer unit.

The linker may for example be any of the linkers described in international patent application WO 2017/045689 in the section "Linker" on p. 56, I. 5 to p. 59, I. 10. The linker may also be any of the linkers described in WO03/052132 in the section "Linker" on p. 54, I. 15 to p. 58, I. 7.

PCR

The methods of the invention preferably comprises the steps of (b) incubating an oligonucleotide of the invention with a target nucleic acid of interest at a temperature which is higher than the melting temperature between said oligonucleotide and the target nucleic acid sequence of interest when said NOI does not comprise the epigenetic modification status investigated, e.g. when said NOI is unmethylated, and (c) detecting whether said oligonucleotide anneals to said target nucleic acid of interest.

Said steps may in preferred embodiments be performed as part of a polymerase chain reaction (PCR). Said PCR is preferably performed in a manner so that most, or even all steps of the PCR are conducted at a temperature, which is higher than the melting temperature between said oligonucleotide and the target nucleic acid sequence of interest when said does not comprise the epigenetic modification status of interest. Even more preferred when said PCR is performed in a manner so that most, or even all steps of the PCR are conducted at a temperature, which is higher than the melting temperature between said oligonucleotide and the target nucleic acid sequence of interest when said NOI is not methylated, but at a temperature low enough to allow for amplification between said oligonucleotide and the target nucleic acid sequence of interest when said NOI is methylated.

A PCR typically comprises multiple cycles of incubation at i. A melting temperature ii. An annealing and extension temperature The annealing and extension temperature may be the same or different temperatures.

Preferably, the PCR is performed in a manner so that the annealing and extension temperature in at least the first cycle, preferably in one or more cycles of said PCR, such as in most of the cycles of said PCR, for example in all cycles of said PCR is higher than the melting temperature between said oligonucleotide and the target nucleic acid sequence of interest when said NOI is unmethylated. Said temperature may in addition be chosen, so that it is at the most 2° C. higher or lower than the melting temperature between said oligonucleotide and the target nucleic acid sequence of interest when said NOI is methylated.

Said annealing temperature depends on the particular oligonucleotide, but it may for example be in the range of 55 to 80° C.

In some embodiments of the invention, the length and/or the temperature of the steps of the PCR are changed during the PCR. In particular, the first cycles, e.g. the first 1 to 5 cycles may be performed in a manner so that methylated DNA is amplified in a more specific manner. Thus, the PCR may comprise one or more epigenetic modification specific amplification cycles and one or more general amplification cycles, wherein the epigenetic modification specific amplification cycle(s) comprise the steps of a. Melting nucleic acids
b. Annealing (and extension) under epigenetic modification specific conditions and the general amplification cycles comprise the steps of a. Melting nucleic acids
b. Annealing (and extension) under general conditions The melting comprises incubation at a melting temperature, which is typically at least 90° C. Annealing and extension under epigenetic modification specific conditions is usually performed at higher temperature than annealing and extension under general conditions, e.g. at a temperature at least 1° C. higher, such as at least 2° C. higher than the temperature used for annealing and extension under general conditions. The method may comprise any suitable number of epigenetic modification specific amplification cycles, for example in the range of 1 to 100 epigenetic modification specific amplification cycles.

The step of incubating at the annealing (and extension) temperature may be performed for any suitable amount of time. For example, at least the first cycle of said PCR may comprise incubation at the annealing temperature for in the range 5 to 120 sec, such as in the range of 10 to 90 sec. The annealing may also for example be performed in the range of 30 to 90 sec, such as for in the range of 45 to 75 sec, for example for approximately 60 sec.

PCR in general involves use of a set of primers capable of amplifying the target nucleic acid sequence of interest. Preferably, one of said primers is the oligonucleotide according to the invention, more preferably a BasePrimer. If the forward primer is an oligonucleotide according to the invention, e.g. a BasePrimer, then the reverse primer is typically a conventional primer and vice versa.

The skilled person will be able to determine a useful concentration of the oligonucleotide of the invention to be used with the PCR. For example said concentration may be in the range of 300 to 700 nM, such as approximately 500 nM.

The PCR may be performed in any suitable manner known to the skilled person. In one embodiment the PCR is a real-time PCR. Real-time PCR typically involves use of a detectable label, such as a dye. In one embodiment, the PCR, e.g. the real-time PCR uses a probe comprising a detectable label for detection of product. Said probe may be any oligonucleotide capable of binding the PCR product, however, preferably the probe is an oligonucleotide capable of binding the PCR product with at least the same affinity and preferably with higher affinity than each of the primers. Thus, the probe may comprise an oligonucleotide at least 90% complementary to a product of said PCR reaction and a detectable label. In preferred embodiments, said probe comprises one or more hydrophobic nucleotides, because hydrophobic nucleotides increases the affinity of the probe.

When the PCR is a real-time PCR, the outcome of the PCR may be determined as Ct. Thus, the target nucleic acid of interest may be considered to be methylated if Ct is below a given threshold. Said threshold may be predetermined or be determined using a relevant control.

In addition to the primers and probes, the PCR will contain PCR reagents. The skilled person is well aware of selecting suitable PCR reagents. PCR reagents in general comprises at least nucleotides and a polymerase. Typically, the PCR reagents also comprise suitable salts and buffer.

The polymerase may be any polymerase useful for PCR, e.g. any DNA polymerase useful for PCR. In some embodiments the polymerase is a polymerase, which stops elongation at any hydrophobic nucleotide in the template. This is the case for most conventional DNA polymerases routinely used PCR.

Clinical Conditions

The methods of the invention may be used to detect methylation of a NOI, the methylation status of which is associated with a clinical condition.

Thus, the methods of the invention may be used for determining the risk of whether an individual suffers from a clinical condition, or the risk of an individual to contract a clinical condition, wherein the clinical condition is associated with the methylation status of an NOI, e.g. a cytosine in a nucleic acid of interest. Such methods usually comprise the steps of:

a. Providing a sample from said individual
b. Determining the methylation status of said NOI in said sample by performing the methods of the invention.

In some aspects is provided a method for determining the risk of whether an individual suffers from a clinical condition, or the risk of an individual to contract a clinical condition, wherein the clinical condition is associated with the methylation status of a NOI in a nucleic acid of interest, said method comprising a. Providing a sample obtained from said individual;
b. Determining the methylation status of said NOI in said sample by performing the method according to any one of the preceding claims, wherein said methylation status is indicative of the presence of or risk of contracting said clinical condition.

The methods of the invention may also be used for determining the likelihood of effect of a treatment of a clinical condition in an individual in need thereof, wherein the effect of said treatment of said clinical condition is associated with the methylation status of a cytosine in a nucleic acid of interest. Such methods usually comprise the steps of:

i. providing a sample from said individual
ii. Determining the methylation status of said NOI in said sample by performing the methods of the invention.

In some aspects of the present invention is provided a method for determining the likelihood of effect of a treatment of a clinical condition in an individual in need thereof, wherein the effect of said treatment of said clinical condition is associated with the methylation status of a NOI in a nucleic acid of interest, said method comprising a. Providing a sample obtained from said individual;
b. Determining the methylation status of said NOI in said sample by performing the methods as disclosed herein, wherein said methylation status is indicative of the effects of different treatment regimens on said clinical condition.

In some embodiments, the NOI is a cytosine.

Many clinical conditions have been shown to be associated with methylation of one or more NOIs, such as several types of cancer, e.g. breast, colon and liver cancer and diseases such as rheumatoid arthritis and multiple sclerosis. Thus, methylation status of one or more NOIs may be indicative of the presence of a clinical condition, the progression of a clinical condition, the seriousness of a clinical condition, the prognosis of a clinical condition, the risk of acquiring a clinical condition or the like. Also, the effects of different treatment regimens have been shown to be associated with the methylation status of one or more NOIs. Thus, the methods of the invention may be employed for detection of all of the aforementioned. The clinical condition may for example be cancer, e.g. glioblastoma.

In preferred embodiments, the methods as disclosed herein above do not involve a surgical step.

In some embodiments, the methods as disclosed herein are performed on a sample isolated from a patient. In some embodiments, said sample is a body fluid sample. Said body fluid sample may be a blood, urine, sputum, breast milk, cerebrospinal fluid, cerumen (earwax), endolymph, perilymph, gastric juice, mucus, peritoneal fluid, pleural fluid, saliva, sebum (skin oil), semen, sweat, tears, vaginal secretion, or vomit sample including components or fractions thereof. Said body fluid samples may be mixed or pooled. Thus, a body fluid sample may be a mixture of blood and urine samples or a mixture of blood and cerebrospinal fluid samples. Said sample may also be homogenized, such as by filtration, dilution and/or centrifugation. In some embodiments, the sample is skin, hair, cells, or tissue.

Items

The invention may further be defined by the following items:

1. A method of determining methylation status of at least one nucleotide of interest (NOI) in a target nucleic acid sequence of interest, wherein said target nucleic acid sequence comprises a target anchor sequence comprising said NOI, said method comprising the steps of
   a. Providing an oligonucleotide comprising an anchor sequence (An), wherein the anchor sequence is a sequence at least 50% complementary to said target anchor sequence, wherein the anchor sequence comprises at least one hydrophobic nucleotide (H) positioned between the nucleotide complementary to said NOI and the nucleotide in the oligonucleotide immediately 5' thereof;
   b. Incubating said oligonucleotide with said target nucleic acid of interest at a temperature which is higher than the melting temperature between said oligonucleotide and the target nucleic acid sequence of interest when said NOI is unmethylated,
   c. Detecting whether said oligonucleotide anneals to said target nucleic acid of interest, thereby determining the methylation status, wherein said hydrophobic nucleotide (H) has the structure $$X—Y—Q$$

wherein

X is a nucleotide or nucleotide analogue or a backbone monomer unit capable of being incorporated into the backbone of a nucleic acid or nucleic acid analogue, Q is an intercalator which is not taking part in Watson-Crick hydrogen bonding; and Y is a linker moiety linking said nucleotide or nucleotide analogue or backbone monomer unit and said intercalator.

2. The method according to item 1, wherein the target nucleic acid of interest is DNA.
3. The method according to any one of the preceding items, wherein the NOI is a cytosine.
4. The method according to any one of items 3 to 4, wherein said cytosine is located in a CpG site, and wherein the anchor sequence comprises the sequence -C-H-G-.
5. The method according to any one of the preceding items, wherein the anchor sequence comprises at least 2, such as at least 3, for example at least 4, such as in the range of 2 to 10, for example in the range of 2 to 5, for example in the range of 3 to 5, such as in the range of 4 to 5-N-H-G- sequences, wherein each N individually is selected from the group consisting of C, G, A and T, and each sequence-N-G- is complementary to a cytosine of interest and its neighbouring nucleotide.
6. The method according to any one of the preceding items, wherein steps b) and c) together comprises performing a PCR, wherein said temperature is used as the annealing temperature in one or more cycles of said PCR.
7. The method according to any one of the preceding items, wherein said oligonucleotide has the structure 5'-An-Lp-St-3', wherein An is the anchor sequence;

Lp is a loop sequence, which is not complementary to the nucleic acid sequence of interest St is a starter sequence, said sequence being at least 90% complementary to a target starter sequence, wherein the target starter sequence is a sequence of the target nucleic acid sequence positioned 5' to the target anchor sequence.
8. The method according to any one of the preceding items, wherein the anchor sequence (An) consists of in the range of 8 to 30, for example in the range of 8 to 20, such as in the range of 10 to 20, for example in the range of 15 to 20 nucleotides, wherein one or more of said nucleotides are hydrophobic nucleotide(s).
9. The method according to any one of the preceding claims, wherein the anchor sequence comprises the sequence -N-H-G-, wherein N is selected from the group consisting of C, G, A and T, and the sequence-N-G- is complementary to the cytosine of interest and its neighbouring nucleotide.
10. The method according to any one of items 8 to 9, wherein Lp and St together consists of at least 15 nucleotides, for example at least 17 nucleotides, such as in the range of 15 to 45 nucleotide, for example in the range of 17 to 35 nucleotides, such as in the range of 17 to 25 nucleotides.
11. The method according to any of the preceding items, wherein target nucleic acid sequence of interest is comprised in DNA purified from a sample.
12. A method for determining the risk of whether an individual suffers from a clinical condition, or the risk of an individual to contract a clinical condition, wherein the clinical condition is associated with the methylation status of a NOI in a nucleic acid of interest, said method comprising
    a. Providing a sample from said individual
    b. Determining the methylation status of said NOI in said sample by performing the method according to any one of the preceding items.
13. A method for determining the likelihood of effect of a treatment of a clinical condition in an individual in need thereof, wherein the effect of said treatment of said clinical condition is associated with the methylation status of a NOI in a nucleic acid of interest, said method comprising
    a. Providing a sample from said individual
    b. Determining the methylation status of said NOI in said sample by performing the method according to any one of items 1 to 10.
14. The method according to any one of items 12 to 13, wherein the clinical condition is cancer.

15. An oligonucleotide comprising or consisting of the following general structure:

$$5'(N)_n—HG—(N)_m—HG—(N)_q\text{-}3',$$

wherein N is any nucleotide or nucleotide analogue; and
G is the nucleotide guanine; and
n is an integer ≥0; and
m is an integer ≥1; and
p is an integer ≥0; and
H is a hydrophobic nucleotide
wherein said hydrophobic nucleotide has the structure $$X—Y—Q$$

wherein
X is a nucleotide or nucleotide analogue or a backbone monomer unit capable of being incorporated into the backbone of a nucleic acid or nucleic acid analogue,
Q is an intercalator which is not taking part in Watson-Crick hydrogen bonding; and
Y is a linker moiety linking said nucleotide or nucleotide analogue or backbone monomer unit and said intercalator.

16. The method or the oligonucleotide according to any one of the preceding claims, wherein at least one, such as all intercalators, Q, are selected from the group consisting of polyaromates and heteropolyaromates optionally substituted with one or more selected from the group consisting of hydroxyl, bromo, fluoro, chloro, iodo, mercapto, thio, cyano, alkylthio, heterocycle, aryl, heteroaryl, carboxyl, carboalkoyl, alkyl, alkenyl, alkynyl, nitro, amino, alkoxyl and amido.

EXAMPLES

The invention is further illustrated by the following examples which however should not be construed as being limiting for the invention.

Example 1

MGMT Promoter Region

The sequence of interest of the MGMT promoter region is comprised herein as SEQ ID NO: 1:

```
CTCTTGCTTTTCTCAGGTCCTCGGCTCCGCCCCGCTCTAGACCCCGCC
CCACGCCGCCATCCCCGTGCCCCTCGGCCCCGCCCCCGCGCCCCGGAT
ATGCTGGGACAGCCCGCGCCCCTAGAACGCTTTGCGTCCCGACGCCCG
CAGGTCCTCGCGGTGCGCACCGTTTGCGACTTGGTGAGTGTCTGGGTC
GCCTCGCTCCCGGAAGAGTGCGGAGCTCTCCCTCGGGACGGTGGCAGC
CTCGAGTGGTCCTGCAGGCGCCCTCA
```

The sequence is 129467120-129467385 *Homo sapiens* chromosome 10, GRCh38.p12. The four underlined CG in SEQ ID NO: 1 are the CpG sites that this assay is designed to analyse the methylation status of. Three out of the selected four CpG sites are commonly used in methylation detection in commercial kits e.g. in Qiagen's pyrosequencing kit (Qiagen. (2014). EpiTect® Fast Bisulfite Conversion Handbook For sample lysis and complete bisulfite Sample & Assay Technologies QIAGEN Sample and Assay Technologies. Sample & Assay Technologies).

General Set-Up of PCR Assay

The following design was used for the set-up of all PCR assays, except for Examples 12 and 13. The volumes are for a single PCR tube containing a total reaction volume of 25 µL:

1) 12.5 µL of a 2× master mix* (MM) containing DNA polymerase, dNTPs, $MgCl_2$ and buffer
2) 7.5 L of primer/probe (PP) mixture
3) 5 µL of purified genomic DNA For Examples 12 and 13 the following design was used for the set-up of PCR assays. The volumes are for a single PCR tube containing a total reaction volume of 12 µL:

1) 6 µL of a 2× master mix* (MM) containing DNA polymerase, dNTPs, $MgCl_2$ and buffer
2) 1 µL of primer/probe (PP) mixture
3) 5 µL of purified genomic DNA

*If not stated otherwise the master mix (MM) consists of 2× Ampliqueen (available from PentaBase ApS). The concentration of $MgCl_2$ is 2.25 mM in working solution of Ampliqueen.

All PCR are carried out on either MyGo Pro (It-Is Life Science ltd), BaseCycler, or Base Typer (PentaBase ApS) real-time PCR instruments. RFU is determined using standard settings on said PCR instruments.

$T_m$ and $\Delta T_m$

Figure 1:
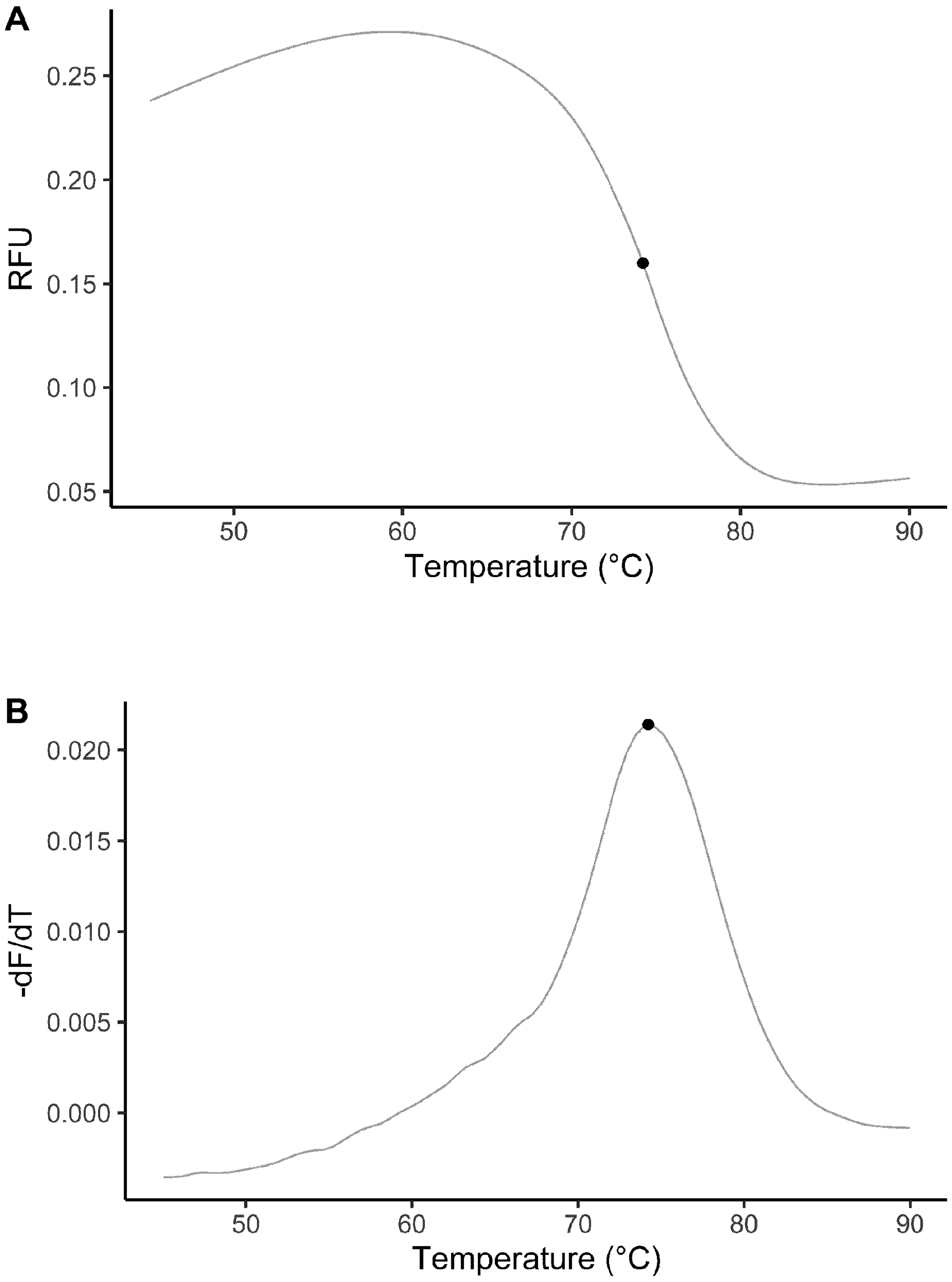
FIG. 1. Determination of the melting temperature ($T_m$). A duplex of a labelled oligonucleotide and its complementary target is heated causing a decrease in RFU when the strands dissociate from each other (see Example 1). Black dot marks the melting temperature. A) Melt curve of probe/target duplex. The melting temperature is the point where the slope is steepest B) The first negative derivative (−dF/dT) of the melt curve in A. The maximum of the curve is the melting temperature.
Figure 2:
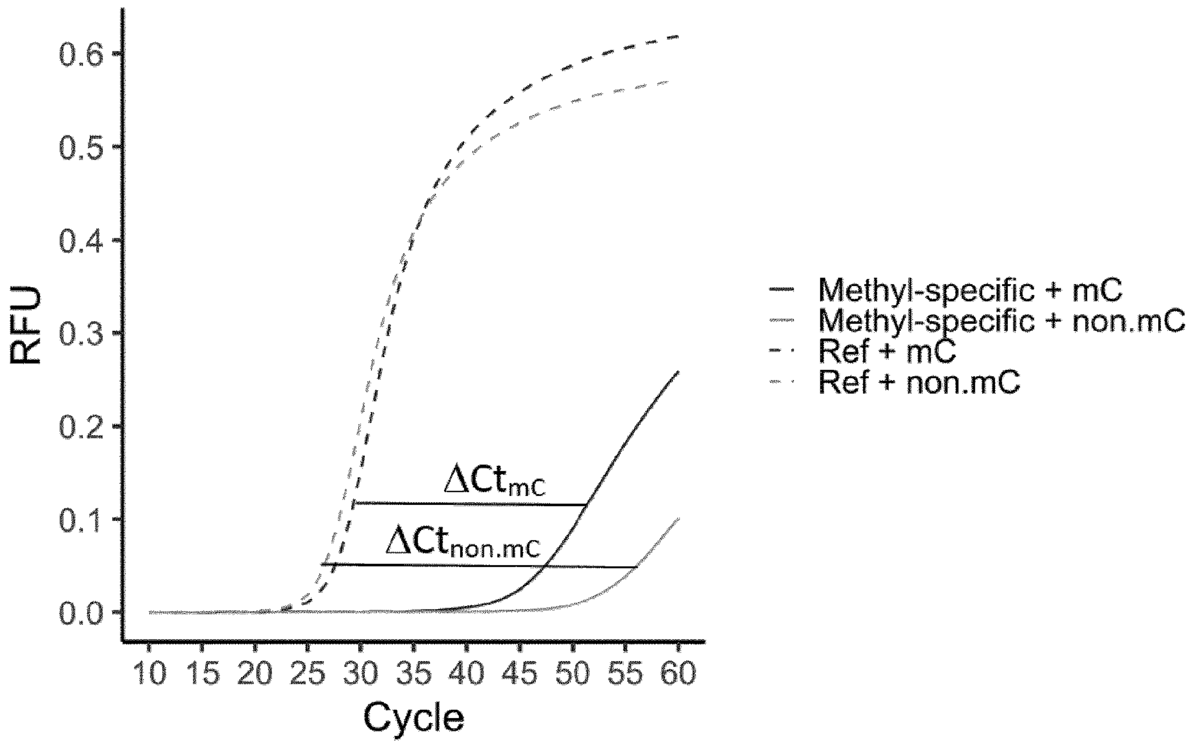
FIG. 2. Illustration of ΔCt for methylated DNA (mC) and non-methylated DNA (non.mC) respectively. ΔCt is calculated as the difference between the Ct value of the reference assay and the Ct value of the methyl-specific assay on either mC or non.mC DNA respectively. Note that the black lines are an illustration of the calculation, and not marks of the exact Ct values.

The melting temperature of an oligonucleotide is found experimentally by incubating the oligonucleotide together with its complementary target at increasing temperature. In general, the oligonucleotide is labelled with a fluorescent label in a manner so that the fluorescent signal is dependent on binding. For example, the oligonucleotide may be linked to a fluorescent moiety in one end and to a quencher at the other end. When the temperature is low, the probe is bound to its target creating a duplex thereby enabling a fluorescence signal, which is measured as RFU. As the temperature is elevated, the RFU decreases, and when it reaches the $T_m$ of the duplex, a sudden drop in RFU can be detected. This is illustrated in FIG. 1A. At the $T_m$ half of the nucleotides bound in the beginning of the melting process will be dissociated from the target. The first negative derivative of the melt curve can be plotted, and the peak (maximum) of this curve is the melting temperature of the probe (FIG. 1 B).

The difference in the $T_m$ is calculated as the difference between a probe bound to one target subtracted from the same probe bond to another target:

$$\Delta T_m = T_{m.target1} - T_{m.target2}$$

Calculation of ΔCt and ΔΔCt

Ct refers to the threshold cycle, i.e. the PCR cycle where a product is detected based on a predetermined criterion. In general, the Ct is determined based on a fluorescence threshold. If not stated otherwise, the default settings of the PCR machine MyGo Pro, BaseCycler or BaseTyper and their associated software are used. Threshold setting is done automatically by the software.

The ΔCt is calculated between the reference assay (i.e. assay using a reference primer) and the methylation sensitive assay (i.e. assay using a methylation specific BasePrimer comprising hydrophobic nucleotides):

$$\Delta Ct = |Ct_{ref} - Ct_{methyl}|$$

The ΔΔCt is calculated as the difference between the ΔCt of the assays when adding non-methylated DNA and the ΔCt of the assays when adding methylated DNA as template:

$$\Delta\Delta Ct = |\Delta Ct_{non.mC} - \Delta Ct_{mC}|$$

The $\Delta Ct_{non.mc}$ thus indicates the difference in Ct between the reference assay and a test assay when using a non-methylated DNA template. The $\Delta Ct_{non.mc}$ is also referred to as $\Delta_{non.mC}$ herein. The $\Delta Ct_{non.mc}$ indicates the specificity of the assay and is preferably as high as possible.

The $\Delta Ct_{mC}$ indicates the difference in Ct between a reference assay and a methylation specific assay using a methylated DNA template. The $\Delta Ct_{mC}$ is also referred to as ΔmC herein. The $\Delta Ct_{mC}$ indicates the sensitivity of the assay as is preferably as low as possible.

The ΔΔCt is the difference between $\Delta Ct_{non.mc}$ and $\Delta Ct_{mC}$, and this should preferably be as high as possible.

BasePrimer Description

Figure 3A:
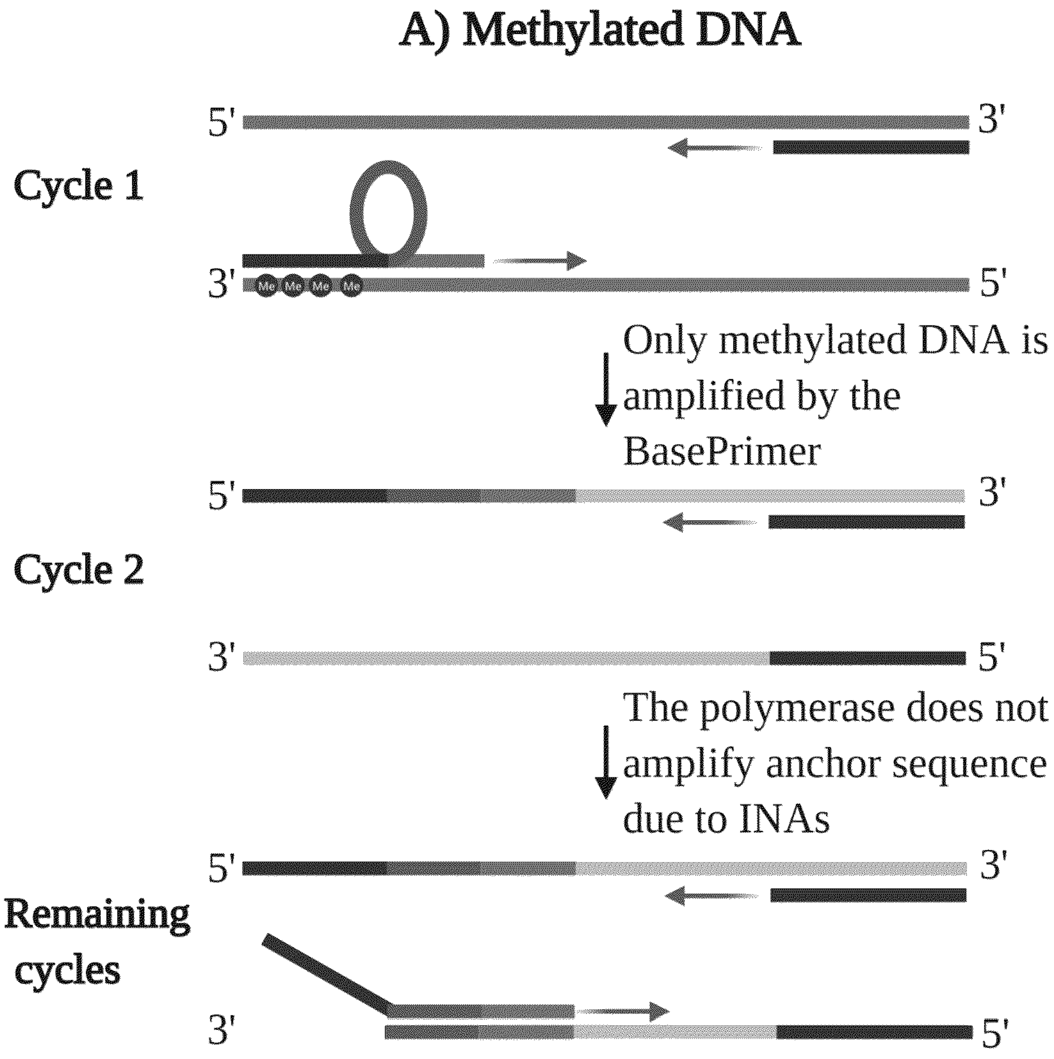
FIG. 3. Illustration of the BasePrimer approach. The BasePrimer consist of an anchor comprising hydrophobic nucleotide(s) targeting the area of potential epigenetic modifications (black), a loop (dark grey) and a starter sequence (lighter grey). A) If the template DNA is methylated the anchor sequence has a high affinity towards the template, and the anchor and the starter sequence of the BasePrimer will anneal to the template DNA and elongation can occur. B) The BasePrimer will not have as high affinity towards unmethylated template and should therefore not bind to an unmethylated template DNA at the chosen conditions. This will ensure that unmethylated templates is not amplified. Note that dark grey lines represent the template strand, light grey the amplicons, and dark circles methylation sites. If the BasePrimer has acted as a primer, the loop and anchor sequences are incorporated in a template that could work for the reverse primer. Elongation from the reverse primer using the template comprising the BasePrimer will normally stop at the anchor sequence because most DNA polymerases cannot read over the hydrophobic nucleotides. The loop and the starter sequences can serve as a regular primer after the methyl-specific amplification has occurred (Created with BioRender.com).
Figure 3B:
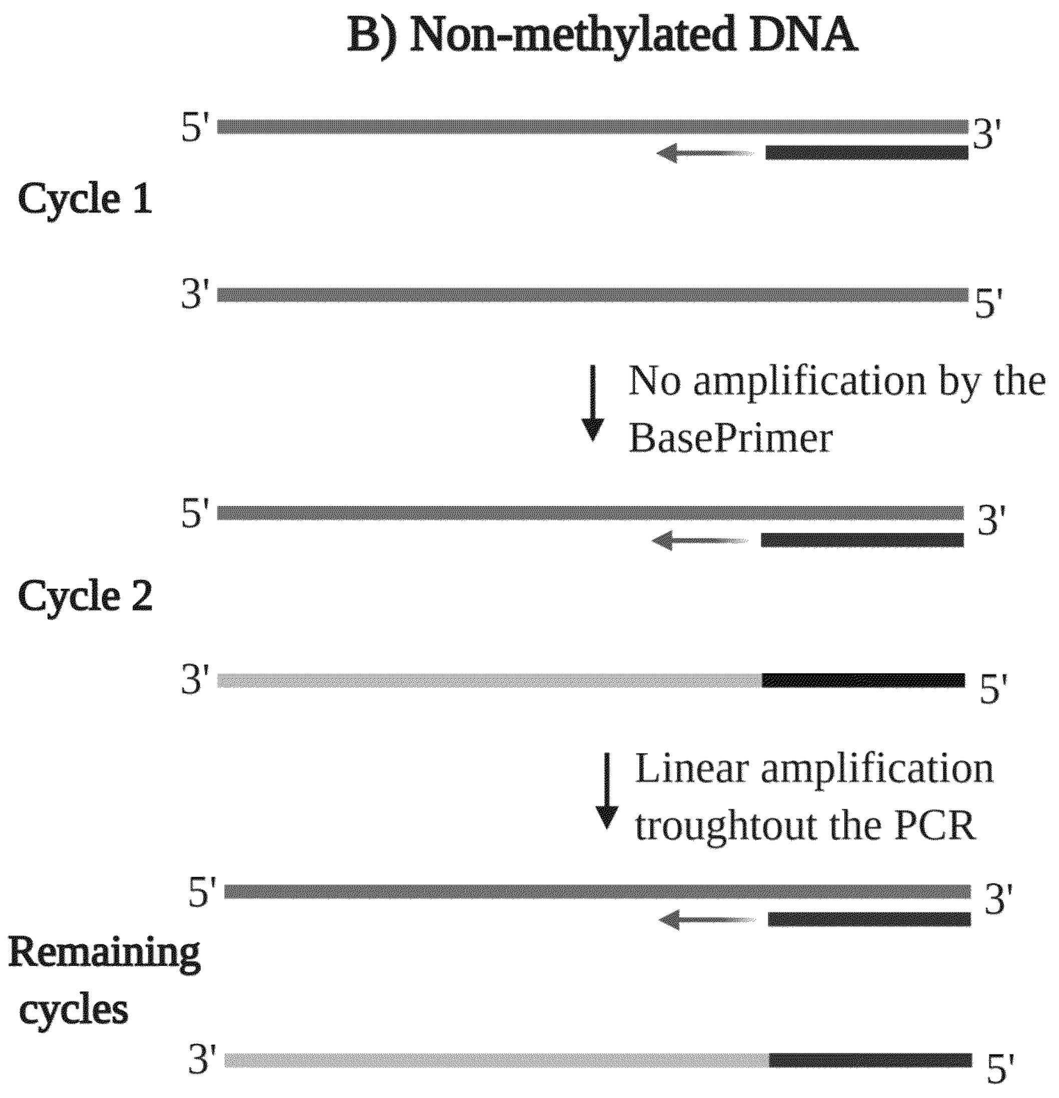
Figure 4:
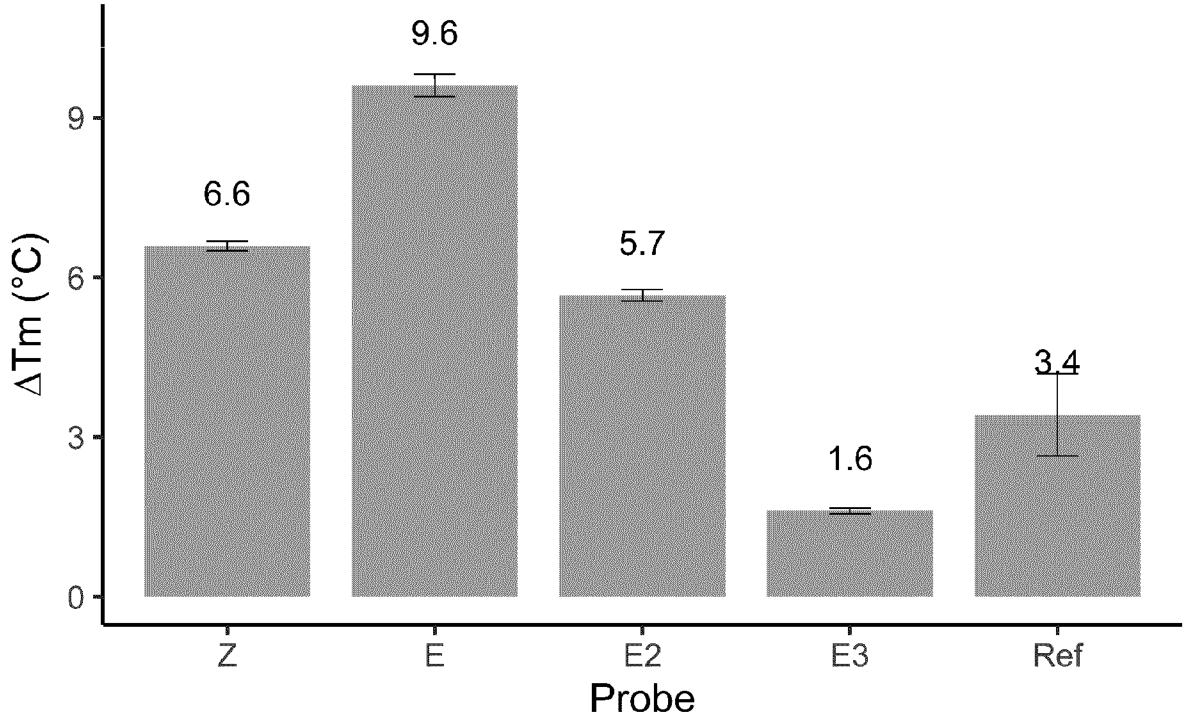
FIG. 4. Bar plot of the difference in melting temperature (ATm) of different types of probes comprising different designs and hydrophobic nucleotides when hybridizing to complementary methylated or unmethylated sequences respectively. The probes MGMT_Z, MGMT_E, MGMT_E2, MGMT_E3 and MGMT_Ref (see sequences in Table 1) were individually mixed with either a non-methylated (MGMT_0mC) or a fully methylated (MGMT_1,2,3,4mC) target, respectively (see sequences in Table 1). The difference in melting temperature between the fully methylated and non-methylated target is illustrated. Three replicates were made for each melt experiment. The average values are shown above the bars.

The BasePrimer approach is based on a selective amplification of methylated DNA using hydrophobic nucleotides. The discrimination can be realized by a single primer, herein named a BasePrimer. A BasePrimer consists of three parts: an anchor, a loop, and a starter sequence. The anchor sequence contains the hydrophobic nucleotides. The anchor sequence has higher thermal stability when bound to methylated DNA compared to unmethylated DNA. Thus, the anchor sequence is used to create stability for the starter sequence that is placed in the 3'-end of the primer. The starter sequence should have low thermal stability, and therefore not bind to the DNA template if it does not get support from the anchor sequence (FIG. 4B). The PCR will only start if the anchor sequence binds with high thermal stability, thus allowing the starter sequence to bind (FIG. 3A, "Cycle 1"). Note that the amplicons created during the PCR will not contain any methylated nucleotides as generally the polymerase adds dNTPs with non-methylated nucleotides in PCR reactions.

The anchor and the starter sequence are connected by a loop sequence. This sequence is beneficial because most polymerases cannot read over the hydrophobic nucleotides and therefore, the anchor sequence will be cut-off when the reverse primer binds and the complementary strand is made. The starter sequence is designed with a low thermal stability, so it cannot bind to the amplicons without an additional sequence. The loop sequence is therefore incorporated into the primer, thereby allowing the loop and starter sequence to work as a regular primer after the second cycle of methyl-specific amplification (FIG. 3A, "Remaining cycles").

Example 2

Affinity Towards 5-Methylcytosine

Oligonucleotides complementary to the region covering the four CpGs marked in SEQ ID NO: 1 above were synthesized. The probes were dual-labelled with a FAM fluorophore in the 5'-end and a black-hole quencher (BHQ) in the 3'-end. In the probes two different hydrophobic nucleotides were used of either type Z or E.

The hydrophobic nucleotide of type Z has the chemical name Phosphoramidite of 3-(1-O-(4,4'-dimethoxytriphenyl-metyl)-2-O-(2-cyanoethyl diisopropylamidophosphite)-1,2-butandiol)-4-N-(7,9-Dimethyl-3H-pyrido[3',2': 4,5]thieno [3,2-d]pyrimidin-4-one. In hydrophobic nucleotides of type Z, the intercalator Q has the structure:

XXVI

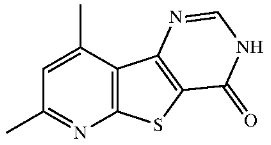

Pyrido[3′,2′:4,5]thieno [3,2-d]pyrimidin-4(1H)-one,7,9-dimethyl-

Herein hydrophobic nucleotides of type Z may simply be referred to as "Z".

The hydrophobic nucleotide of type E has the chemical name Phosphoramidite of(S)-1-(4,4'-dimethoxytriphenyl-metyloxy)-3-pyrenemethyloxy-2-propanol. In this hydrophobic nucleotides of type E, the intercalator Q has the structure:

XII

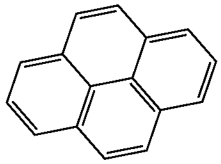

Pyrene

Herein hydrophobic nucleotides of type E may simply be referred to as "E".

Either Z or E were incorporated into the probe in a manner so they are positioned between the C and the G in the four CpGs of SEQ ID NO:1. This was done to test which of E and Z best discriminated between methylated DNA (referred to as "5-mC") and nonmethylated DNA (referred to as "non.mC").

Furthermore, E was tested in different positions. Probes comprising E positioned between the C and G in the CpGs are referred to as Probes of type E herein. Probes where E is positioned immediately before the CpGs upon annealing are referred to as probes of type E2 and probes where E is positioned immediately after the CpGs upon annealing are referred to as probes of type E3. As reference, a probe was made without E and Z. The sequences of the different probes are provided in table 1.

Two artificial targets were designed and synthesized: One without any methylated cytosines (mC) and one with mC at the four CpG sites. The sequences are found in table 1.

TABLE 1

Probes and target sequences used for analysis of dual-labelled probes containing E and Z at various positions affinity towards a complementary target comprising 5-methylcytosine (mC) or standard cytosine (C) nucleobases.

| SEQ ID: NO: | Name | Sequence |
|---|---|---|
| | | Probes |
| 2 | MGMT_Z | 5'-FAM-CZGTCCCZGACZGCCCZG-BHQ1-3' |
| 3 | MGMT_E | 5'-FAM-CEGTCCCEGACEGCCCEG-BHQ1-3' |
| 4 | MGMT_E2 | 5'-FAM-ECGTCCECGAECGCCECG-BHQ1-3' |
| 5 | MGMT_E3 | 5'-FAM-CGETCCCGEACGECCCGE-BHQ1-3' |
| 6 | MGMT_Ref | 5'-FAM-CGTCCCGACGCCCG-BHQ1-3' |
| | | Targets |
| 7 | MGMT_0mC | 5'-CGGGCGTCGGGACG-3' |
| 8 | MGMT_1,2,3,4mC | 5'-mCGGGmCGTmCGGGAmCG-3' |

Melting temperature was determined as described in Example 1.

It was observed that the probes containing hydrophobic nucleotides type E and Z had a higher $T_m$ when bound to the fully methylated target (MGMT_1,2,3,4mC) compared to the non-methylated target (MGMT_0mC). The difference in melting temperature for 1,2,3,4mC and 0mC was ~ 6.6° C. for probe MGMT_Z and ~ 9.6° C. for probe MGMT_E. In addition, it was observed that the reference probe (MGMT_Ref) also had a higher $T_m$ when hybridized to the methylated target with a difference between mC and non.mC target of 3.4° C., see FIG. 4 and table 2.

Figure 5:
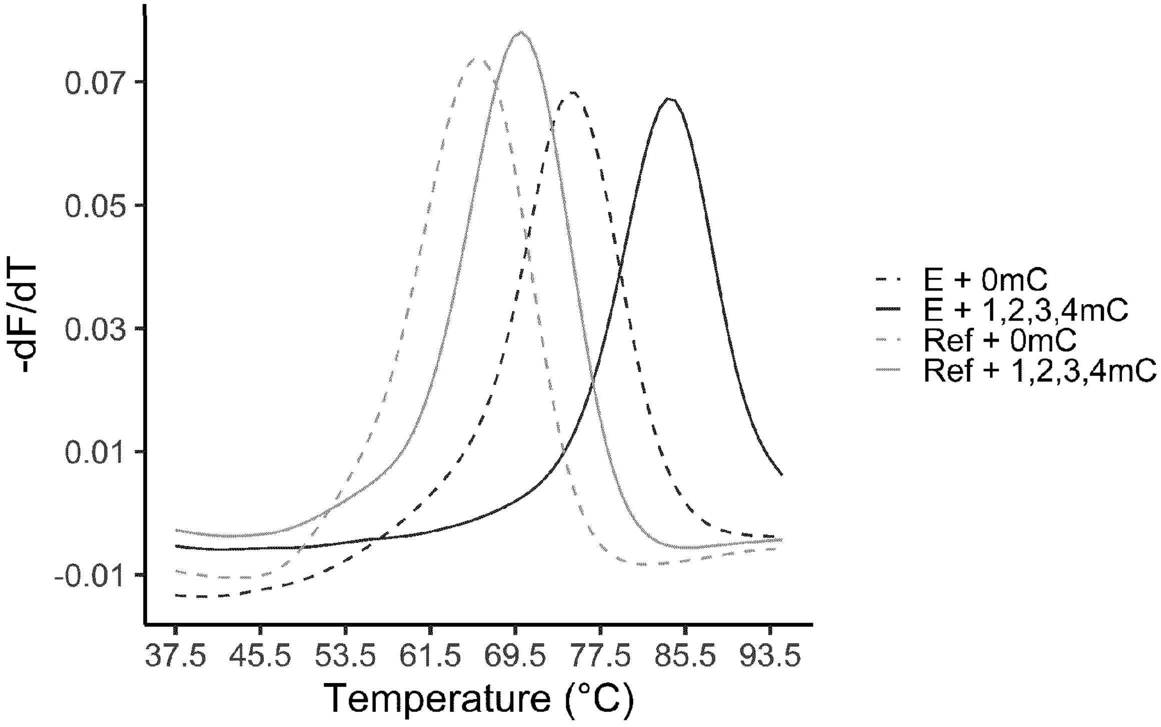
FIG. 5. Melting peaks (first negative derivate of melting curves) of the probe MGMT_E and the reference probe MGMT_Ref (see sequences in Table 1) hybridized to target MGMT_1,2,3,4mC and MGMT_0mC respectively. It is seen that MGMT_E has a higher melting temperature when hybridized to both methylated and non-methylated target, but at the same time also a better discrimination between these (larger $\Delta T_m$) compared to the reference probe.

The position of the hydrophobic nucleotide type E was investigated. The best discrimination occurred when E was placed in between the C and the G in the CpGs (probe MGMT_E). When the hydrophobic nucleotide was placed after the CpG (probe MGMT_E3), lower discrimination was observed than for the reference probe. The difference in the first negative derivative of the melt of MGMT_E and MGMT_Ref with the methylated (MGMT_1,2,3,4mC) and non-methylated targets (MGMT_0mC) are seen in FIG. 5.

TABLE 2

Melting temperature for MGMT_Z, E, E2, E3 and Ref melted with targets containing either 0 or 4 methylation sites.

| Probe | Rep | 0 mC [° C.] | 1, 2, 3, 4 mC [° C.] |
|---|---|---|---|
| MGMT_Z | 1 | 76.06 | 82.76 |
| | 2 | 76.28 | 82.80 |
| | 3 | 76.27 | 82.83 |
| | Avg | 76.21 | 82.80 |
| | SDV | 0.10 | 0.03 |
| MGMT_E | 1 | 74.30 | 84.11 |
| | 2 | 74.48 | 84.12 |
| | 3 | 74.43 | 83.82 |
| | Avg | 74.41 | 84.02 |
| | SDV | 0.07 | 0.14 |
| MGMT_E2 | 1 | 69.18 | 74.97 |
| | 2 | 68.90 | 74.51 |
| | 3 | 69.30 | 74.90 |
| | Avg | 69.13 | 74.79 |
| | SDV | 0.17 | 0.20 |

TABLE 2-continued

Melting temperature for MGMT_Z, E, E2, E3 and Ref melted with targets containing either 0 or 4 methylation sites.

| Probe | Rep | 0 mC [° C.] | 1, 2, 3, 4 mC [° C.] |
|---|---|---|---|
| MGMT_E3 | 1 | 65.03 | 66.61 |
| | 2 | 65.01 | 66.61 |
| | 3 | 65.06 | 66.73 |
| | Avg | 65.03 | 66.65 |
| | SDV | 0.02 | 0.06 |
| MGMT_Ref | 1 | 66.30 | 70.01 |
| | 2 | 67.39 | 69.94 |
| | 3 | 65.98 | 69.99 |
| | Avg | 66.56 | 69.98 |
| | SDV | 0.60 | 0.03 |

Avg. = average

SDV = standard deviation

Example 3

Affinity of the Z and E Modified Probes in Relation to Position and Numbers of 5-mCs The correlation between melting temperature of the Z and E modified probes with a complementary target and the positioning and numbers of 5-mC in said target oligo was investigated. Four different targets were designed each comprising one methylated CpG site.

Furthermore, one target was designed with two methylated CpG sites, and one with four methylated CpG sites. This was done to investigate the correlation between number of 5-mC and melting temperature of the probes. The sequences are found in Table 3.

TABLE 3

| Probes and target sequences used for analysis of affinity by changing the position of 5-mC. C = non methylated cytosine. mC = 5-methylcytosine | | |
|---|---|---|
| SEQ ID NO: | Name | Sequence |
| | | Probes |
| 3 | MGMT_E | 5'-FAM-CEGTCCCEGACEGCCCEG-BHQ1-3' |
| 6 | MGMT_Ref | 5'-FAM-CGTCCCGACGCCCG-BHQ1-3' |
| | | Targets |
| 7 | MGMT_0mC | 5'-CGGGCGTCGGGACG-3' |
| 8 | MGMT_1,2,3,4mC | 5'-mCGGGmCGTmCGGGAmCG-3' |
| 9 | MGMT_1mC | 5'-mCGGGCGTCGGGACG-3' |
| 10 | MGMT_2mC | 5'-CGGGmCGTCGGGACG-3' |
| 11 | MGMT_3mC | 5'-CGGGCGTmCGGGACG-3' |
| 12 | MGMT_4mC | 5'-CGGGCGTCGGGAmCG-3' |
| 13 | MGMT_2,3mC | 5'-CGGGmCGTmCGGGACG-3' |

No significant difference between the positions of methylation sites in the target on melting temperature was observed.

Figure 6:
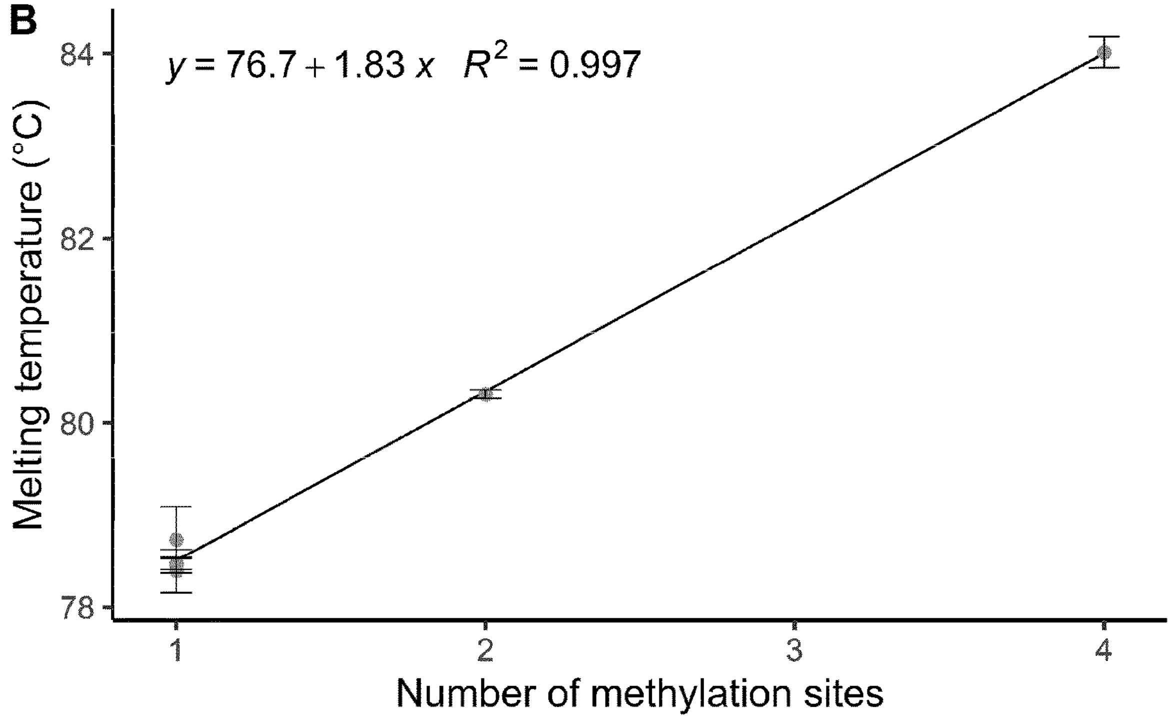
FIG. 6. The graph illustrates that there is a correlation between the number of methylated sites under a probe, and the affinity of the probe. Linear fits between the number of methylation sites and the melting temperature of probe MGMT_E is shown. Linear fit applied to melting temperature of probe MGMT_E hybridised to targets MGMT_1mC, MGMT_2mC, MGMT_3mC, MGMT_4mC, having 1 methylated cytosine each, MGMT_2,3mC, and MGMT_1,2,3,4mC having 2 and 4 methylated cytosines, respectively (see sequences in Table 3). Three replicates were made for each melt experiment.

The correlation between the number of methylation sites and melting temperature of the probe was investigated. The $R^2$ of the linear fit when the non-methylated target excluded gave a $R^2$ of 0.997. This indicates that there is a linear correlation when targets are methylated. The non-methylated target had a too low a melting temperature to fit in the linear model. The plot is shown in FIG. 6 and the raw data is presented in table 4.

TABLE 4

Melting temperature for MGMT_E melted with targets 0, 1, 2 and 4 methylation sites.

| Probe | Rep | 0 mC [° C.] | 1, 2, 3, 4 mC [° C.] | 1 mC [° C.] | 2 mC [° C.] | 3 mC [° C.] | 4 mC [° C.] | 2, 3 mC [° C.] |
|---|---|---|---|---|---|---|---|---|
| MGMT_E | 1 | 74.30 | 84.11 | 78.52 | 78.41 | 78.72 | 78.58 | 80.36 |
| | 2 | 74.48 | 84.12 | 78.46 | 78.54 | 79.10 | 78.13 | 80.30 |
| | 3 | 74.43 | 83.82 | 78.36 | 78.47 | 78.39 | 78.47 | 80.27 |
| | Avg | 74.41 | 84.02 | 78.45 | 78.48 | 78.74 | 78.39 | 80.31 |
| | SDV | 0.07 | 0.14 | 0.07 | 0.05 | 0.29 | 0.19 | 0.04 |

Example 4

Melt Studies in Ampliqueen Master Mix

Figure 7:
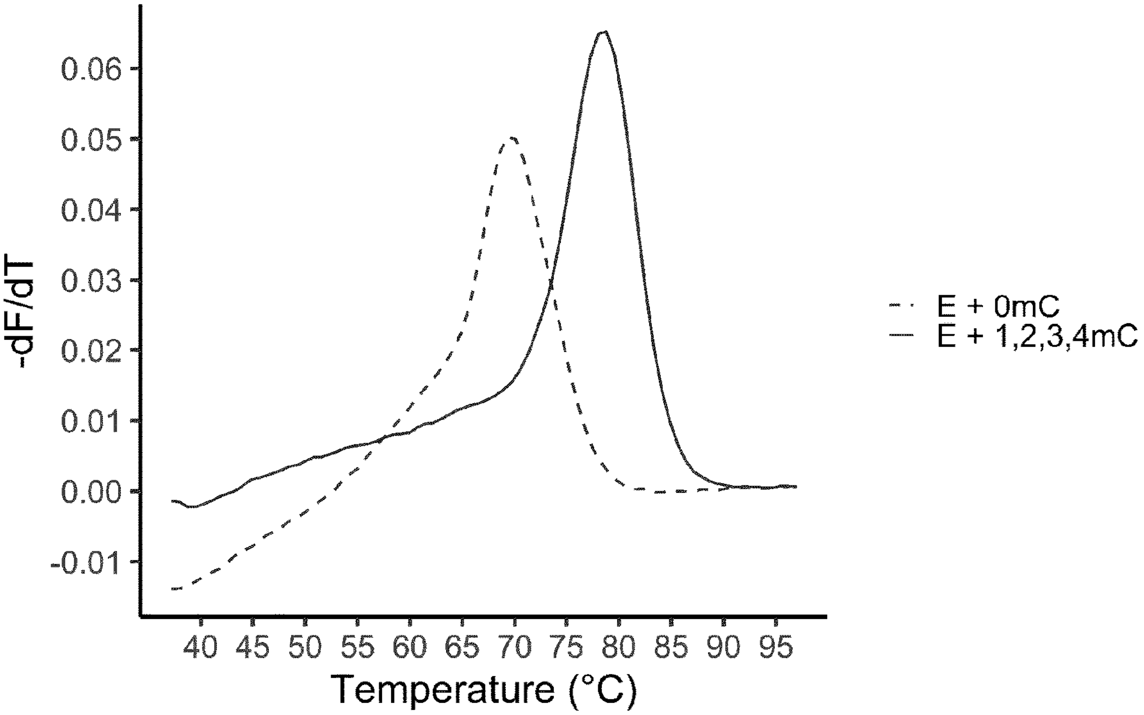
FIG. 7. Melting peaks of probe MGMT_E in AmpliQueen master mix (available from PentaBase). The first negative derivate of the melting curves of probe MGMT_E hybridized to each of target MGMT_1,2,3,4mC and MGMT_0mC. It is seen that the MGMT_E/MGMT_0mC duplex is first fully dissociated at 80° C. This suggests that at approximately 80° C. it is possible for probe MGMT_E to bind selectively to a methylated complementary sequence in said master mix.

It was shown that the melting temperature was decreased by approximately 5° C. by melting the duplexes in 1× Ampliqueen (PentaBase ApS) compared to TM buffer (see table 5). TM buffer comprises 0.02 M $Na_2HPO_4$, 0.02 M NaCl, and 2 mM EDTA. The melting temperature of the MGMT_E/1,2,3,4mC duplex was ~78.5° C. and for MGMT_E/0mC duplex it was ~69.7° C. It is first at 80° C. that the MGMT/0mC duplex is fully dissociated into two single strands. This is seen by the temperature after the melt peak, where-dF/dT is 0, see FIG. 7.

TABLE 5

$T_m$ of MGMT_E melted with targets containing 0 or 4 methylation sites in TM Buffer and Ampliqueen master mix.

| | | TM Buffer | | Ampliqueen | |
|---|---|---|---|---|---|
| Probe | Rep | 0 mC [° C.] | 1, 2, 3, 4 mC [° C.] | 0 mC [° C.] | 1, 2, 3, 4 mC [° C.] |
| MGMT_E | 1 | 76.06 | 82.76 | 69.61 | 78.49 |
| | 2 | 76.28 | 82.80 | 69.72 | 78.55 |
| | 3 | 76.27 | 82.83 | | |
| | Avg | 76.21 | 82.80 | 69.66 | 78.52 |
| | SDV | 0.10 | 0.03 | 0.06 | 0.03 |

Example 5

Design of BasePrimers

Four different designs of BasePrimers were made (table 6). The primers were designed to have two different loop sequences, and two different lengths of the 3'-end starter sequence. The melting temperature is calculated based on the $T_m$ of the loop sequence and the 3'-end starter sequence as these sequences will work as one primer after the loop sequence has been incorporated into the amplicons.

TABLE 6

BasePrimer designs. Bold = anchor sequence. Standard letters = loop sequence. Underlined = 3'-end starter sequence.

| SEQ ID NO: | Name | Sequence | Tm [° C.] |
|---|---|---|---|
| 14 | MGMT_Fw Loop3B | 5'-**CEGTCCCEGACEGCCCEG**AGGCTTCTG ACAGGTCCTCG-3' | 67.8 |
| 15 | MGMT_Fw Loop3C | 5'-**CEGTCCCEGACEGCCCEG**AGGCTTCTG ACAGGTCCTCGCG-3' | 72.6 |
| 16 | MGMT_Fw Loop4B | 5'-**CEGTCCCEGACEGCCCEG**AGGCTTCAC TGACAGGTCCTCG-3' | 69.8 |
| 17 | MGMT_Fw Loop4C | 5'-**CEGTCCCEGACEGCCCEG**AGGCTTCAC TGACAGGTCCTCGCG-3' | 74.1 |

TABLE 7

Primers and probes

| SEQ ID NO: | Name | Sequence | Tm [° C.] |
|---|---|---|---|
| 18 | MGMT_Fw2C | 5'-CGCCCCTAGAACGCTTTGCGTCCC-3' | 73.0 |
| 19 | MGMT_Rev2C | 5'-GGAGCGAGGCGACCCAGACACTCA-3' | 72.8 |
| 20 | MGMT_Probe2A | 5'-FAM-CAAGTCZGCAAACZGGTZG-BHQ1-3' | 74.7 |
| 21 | MGMT_Probe2B | 5'-FAM-CAAGTCGCZAAACZGGTZG-BHQ1-3' | 74.7 |
| 22 | MGMT_Probe2D | 5'-FAM-CAAGTCGCZAAACZGGTGCZG-BHQ1-3' | 79.2 |
| 23 | MGMT_Probe2E | 5'-FAM-CAAGTCGCZAAACZGGTGCZGCAC-BHQ1-3' | 81.7 |

Test of BasePrimers

PCRs were set up using the BasePrimers of Table 6 as forward primers and reverse primer MGMT_Rev2C (Table 4). Reference assays used primer MGMT_Fw2C as forward primer and MGMT_Rev2C as reverse primer (Table 7).

The methyl-specific assay was performed by mixing 700 nM of each BasePrimer of Table 7 with 700 nM MGMT_Rev2C and 500 nM MGMT_Probe2E (Table 7). The reference assay was made by mixing 700 nM MGMT_Fw2C with 700 nM MGMT_Rev2C and 500 nM MGMT_Probe2E. The PCR program is provided in table 8, whereas the optimization protocol for optimizing the PCR program is provided in table 9.

Only MGMT_FwLoop3C and FwLoop4C were used in the program optimization, and only FwLoop4C was tested at 79° C. In this experiment master mix containing 1% ZUBR Green was used for signal generation. 1 ng/μL non-methylated DNA from healthy donor and 1 ng/μL methylated DNA (purified from cell-line IDH U87 WT) was used for the experiments.

TABLE 8

PCR Program D.

| PCR Program D | | Temperature [° C.] | Time [sec] | No. of cycles |
|---|---|---|---|---|
| Hold | | 95 | 120 | 1 |
| 2-step Amplification | Step 1 | 95 | 30 | 60 |
| | Step 2 | 75 | 45* | |

*= acquiring stage (the stage where the fluorescence is acquired)

TABLE 9

Optimization of PCR Program D

| Step 2 - Temperature [° C.] | Step 2 - Time [sec] |
|---|---|
| 75 | 20 |
| | 45 |
| 77 | 20 |
| | 30 |
| 79 | 20 |
| | 30 |

All BasePrimers were found to be useful for amplification of DNA. MGMT_FwLoop3B and FwLoop4B were found to have high Ct value of the methyl-specific assay compared to the reference assay, which means that the BasePrimer amplified methylated DNA at low efficiency. MGMT_FwLoop3C and FwLoop4C had low ΔCt on the methylated DNA, which means that the BasePrimers amplified the methylated DNA nearly as efficiently as the reference assay. However, the FwLoop3C and FwLoop4C did not discriminate well between methylated and non-methylated DNA (ΔΔCt<0.5). The two BasePrimers were tested at shorter annealing time and higher temperature, and the discrimination improved, see FIG. 8.

Figure 8:
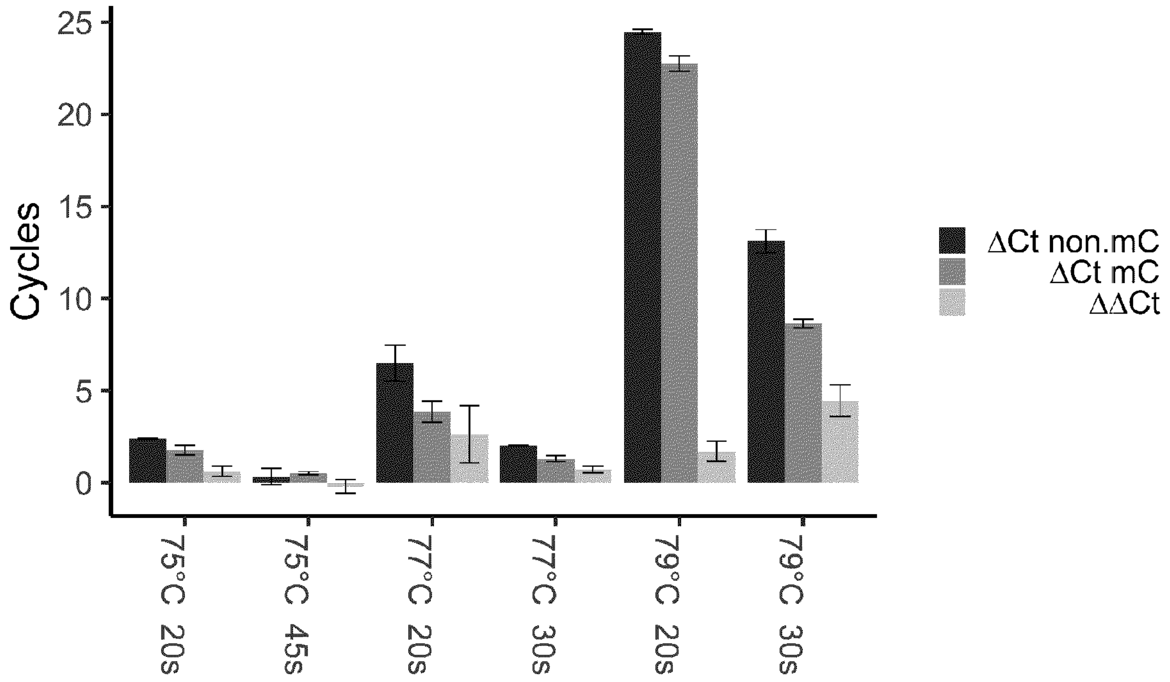
FIG. 8. Bar plot of difference in PCR cycles to signal (ΔCts) between BasePrimers and reference primers under different annealing times and temperatures. ΔCt between methyl-specific and reference assay and the ΔΔCt difference between methylated and non-methylated DNA are used to illustrate the optimal annealing conditions. The annealing temperatures and times are indicated in the figure. The reference assay used 700 nM of MGMT_Fw2C and MGMT_Rev2C and 500 nM MGMT_Probe2E as described in the section "Design of BasePrimers" in the Examples below. The methyl-specific assay used MGMT_FwLoop4C primer instead of MGMT_Fw2C. For the experiments at 79° C. 1% ZUBR Green was used instead of MGMT_Probe2E.

For both annealing temperature of 77° C. and of 79° C., it was observed that the ΔCt of both methylated and non-methylated DNA decreased when the anneal time was increased from 20 sec to 30 sec (FIG. 8). This indicates that the BasePrimer needs more time to anneal to the methylated template with high efficiency. The highest ΔΔCt was at 79° C. for 30 sec and was 4.46±0.86.

Example 6

Methyl-Specific Pre-Amplification

MGMT_FwLoop4C was tested on a PCR program with methyl-specific pre-amplification (table 10). The methyl-specific assay was made by mixing 700 nM of MGMT_FwLoop4C with 700 nM MGMT_Rev2C. The reference assay was made by mixing 700 nM MGMT_Fw2C with 700 nM Rev2C. Master mix containing 1% ZUBR Green was used in both the reference and methyl-specific assay. The results were compared to the regular 2-step amplification with 79° C. for 20 sec as annealing settings. The same experimental set-up was used as in the example above.

TABLE 10

PCR Program E.

| PCR Program E | | Temperature [° C.] | Time [sec] | No. of cycles |
|---|---|---|---|---|
| Hold | | 95 | 120 | 1 |
| Pre-amplification | Step 1 | 95 | 30 | 5 |
| | Step 2 | 80 | 60 | |
| 2-step | Step 1 | 95 | 30 | 55 |
| Amplification | Step 2 | 79 | 20* | |

*= acquiring stage (the stage where the fluorescence is acquired)

ΔCt and ΔΔCt were determined as described in Example 1 above.

Figure 9:
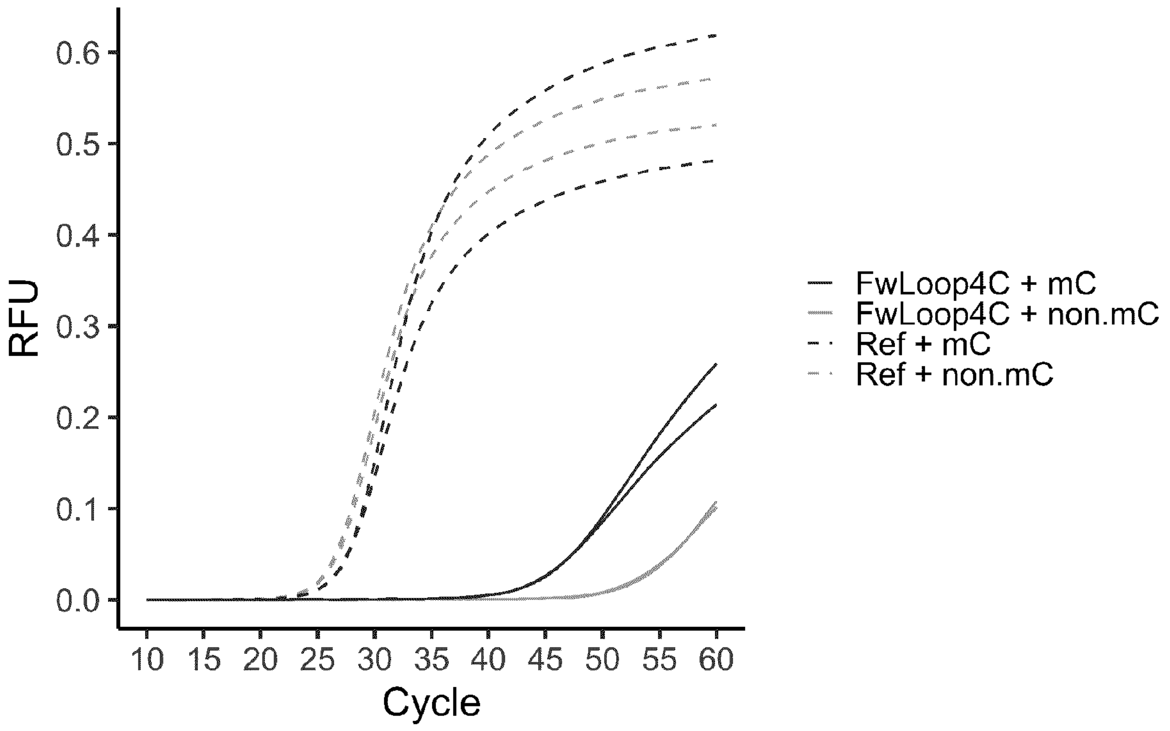
FIG. 9. PCR curves of reference and methyl-specific assay on methylated and non-methylated DNA. The relative fluorescence units (RFU) of the probe is plotted as a function of cycle. PCR Program E (see Table 10) was used. The samples tested was methylated DNA isolated from IDH U87 WT (mC) and DNA from healthy donors as control (non.mC). 700 nM MGMT_Fw2C, 700 nM MGMT_Rev2C and 1% ZUBR Green was used in the reference assay (Ref), and the methyl-specific assay had 700 nM MGMT_FwLoop4C instead of MGMT_Fw2C.

The methyl-specific pre-amplification cycling gave lower Ct values for the methylated DNA and higher Ct for non-methylated DNA on the methyl-specific assay and thereby improved the discrimination of methylation to a ΔΔCt value of 9.93, see table 11. The PCR curves for the methyl-specific pre-amplification PCR are seen in FIG. 9. However, the Ct values of the methylated DNA on the methyl-specific assay was still high with the pre-amplification, and it was assumed that the loop and starter sequence did not amplify well in the 2-step non-methyl-specific amplification.

TABLE 11

Results table methyl-specific pre-amplification vs non-methylation specific pre-amplification

| Template | Conc [ng/μL] | Ref Ct | Loop4C Ct | ΔCt |
|---|---|---|---|---|
| No methyl-specific ampli | | | | |
| Non-methylated | 1 | 30.96 ± 0.01 | 55.44 ± 0.10 | 24.48 |
| Methylated | 1 | 31.89 ± 0.01 | 53.65 ± 0.31 | 22.76 |
| ΔΔCt | | | | 2.76 |
| Methyl-specific ampli | | | | |
| Non-methylated | 1 | 30.51 ± 0.05 | 58.70 ± 0.18 | 28.20 |
| Methylated | 1 | 31.49 ± 0.19 | 49.76 ± 0.67 | 18.27 |
| ΔΔCt | | | | 9.93 |

Example 7

Design of Higher $T_m$ BasePrimer

A BasePrimer was designed with a loop sequence with higher affinity for complementary sequence and 3'-end starter sequence to work at higher temperature in the 2-step amplification. The design is seen in Table 12. The affinity of the MGMT_Fw2C and MGMT_Rev2C was increased by adding a hydrophobic nucleotide in the 5' end of these primers instead of using regular primers.

TABLE 12

BasePrimer design. Bold = anchor sequence. Standard letters = loop sequence. Underlined = 3'-end starter sequence.

| SEQ ID NO: | Name | Sequence | Tm [° C.] |
|---|---|---|---|
| 24 | MGMT_Fw Loop5C | 5'-**CEGTCCCEGACEGCCCEG**AGCGCTTCACTG AGACAGGTCCTCGCG-3' | 78.1 |
| 25 | MGMT_Fw 2C_suE | 5'-ECGCCCCTAGAACGCTTTGCGTCCC-3' | 75.7 |
| 26 | MGMT_Rev 2C_suE | 5'-EGGAGCGAGGCGACCCAGACACTCA-3' | 79.5 |

The new BasePrimer was first analyzed without the pre-amplification to find out optimal annealing time and temperature in the 2-step amplification. The assays were mixed as described in "Methyl-specific pre-amplification", but using MGMT_FwLoop5C as forward primer instead. PCR program D was modified according to table 13. The SW1088 cell line was used for this experiment and the next experiments as well.

TABLE 13

| Optimization of PCR Program D | |
|---|---|
| Step 2 - Temperature [° C.] | Step 2 - Time [sec] |
| 81 | 30 |
| | 45 |
| | 60 |
| 79 | 30 |
| 80 | |
| 81 | |

ΔCt and ΔΔCt were determined as described in Example 1 above.

Figure 10:
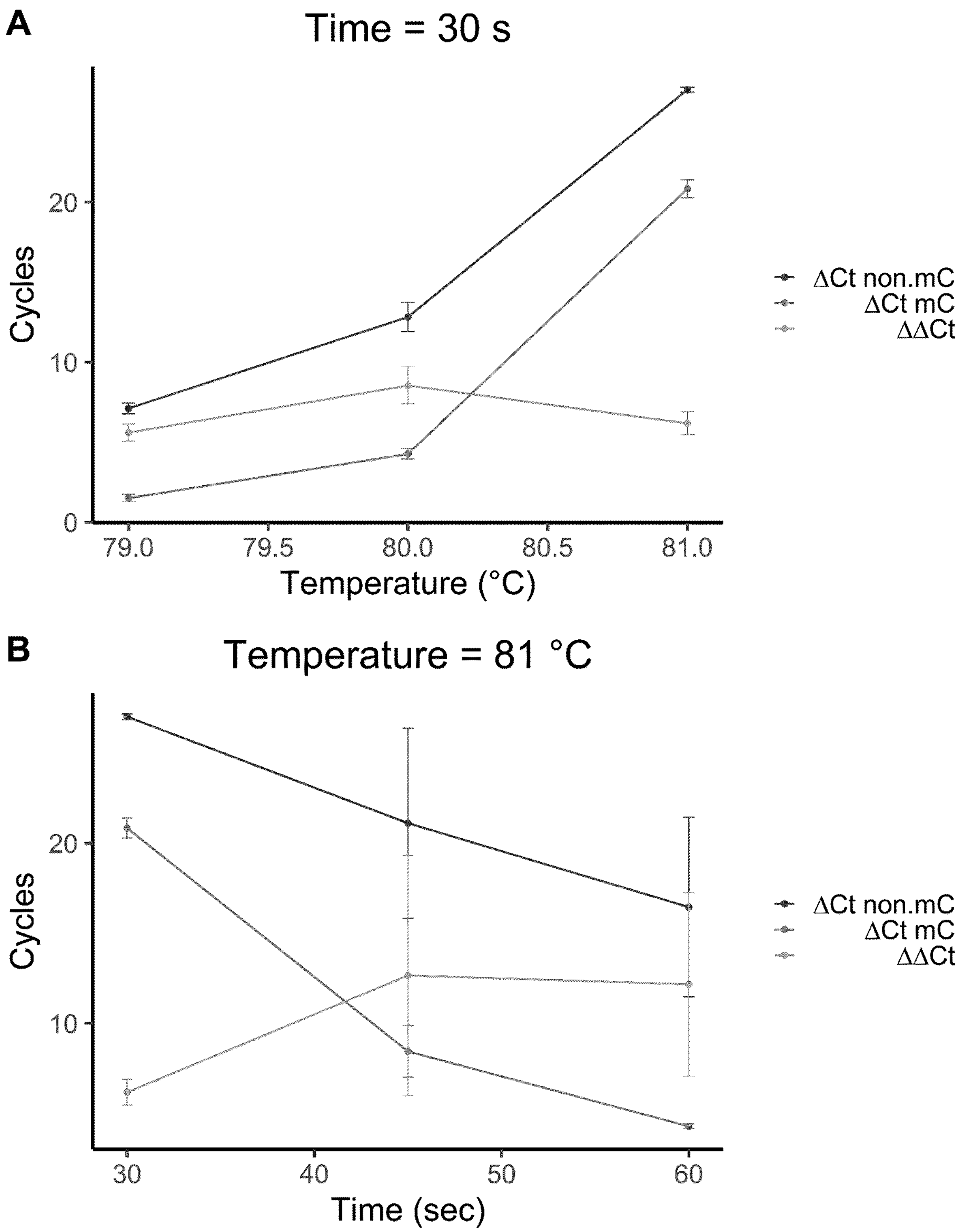
FIG. 10. Dot plots of MGMT_FwLoop5C at different anneal times and temperatures (see Table 12 for sequence). ΔCt between methyl-specific and reference assay and the ΔΔCt difference between methylated and non-methylated DNA are used to illustrate the effect of changes in annealing time and temperature A) The annealing time was fixed to 30 s and the temperature was varied. B) The annealing temperature was fixed to 81° C., and the annealing time was varied. The reference assay had 700 nM of MGMT_Fw2C_suE and MGMT_Rev2C_suE and 1%

The results obtained for ΔCt and ΔΔCt at different annealing times and temperatures for the BasePrimer MGMT_FwLoop5C are shown in FIG. 10. It was found that higher annealing temperature (time fixed to 30 sec) lead to worse methyl-specific amplification of both methylation and non-methylated DNA. The best discrimination between methylated and non-methylated DNA was observed at 80° C.

Example 8

Titration of MGMT FwLoop5C

The BasePrimer was tested with a methyl-specific pre-amplification using PCR Program E, but with 81° C. in the second step of the pre-amplification, and the second step in the 2-step amplification was tested at both 79 and 80° C.

| PCR Program E | | Temperature [° C.] | Time [sec] | No. of cycles |
|---|---|---|---|---|
| Hold | | 95 | 120 | 1 |
| Methyl-specific pre-amplification | | 95 | 30 | 5 |
| | | 80 | 60 | |
| 2-step Amplification | Step 1 | 95 | 30 | 55 |
| | Step 2 | 79 | 20* | |

Using PCR Program E but with 81° C. in the second step of the pre-amplification, and 80° C. in the second step in the 2-step amplification, MGMT_FwLoop5C was titrated at concentrations of 500, 700 and 900 nM. Except for the variating concentrations, the assays were made as described in the section "Design of higher $T_m$ BasePrimer".

The MGMT_FwLoop5C was analyzed using methyl-specific pre-amplification. 500 nM FwLoop5C was the optimal concentration for the BasePrimer. Here the ΔΔCt was 12.6, and the ΔCt of methylated DNA was 9.8. Higher concentrations lead to worse methyl-specific amplification, see results in table 14.

TABLE 14

Results table titration of MGMT_FwLoop5C.

| Template | Conc [ng/μL] | Ref Ct | Loop4C Ct | ΔCt |
|---|---|---|---|---|
| | 500 nM FwLoop5C | | | |
| Non-methylated | 1 | 27.20 ± 0.15 | 49.62 ± 1.22 | 22.41 |
| Methylated | 1 | 26.98 ± 0.23 | 36.76 ± 1.36 | 9.78 |
| ΔΔCt | | | | 12.63 |
| | 700 nM FwLoop5C | | | |
| Non-methylated | 1 | 27.20 ± 0.15 | 50.76 ± 0.07 | 23.55 |
| Methylated | 1 | 26.98 ± 0.23 | 40.48 ± 1.67 | 13.50 |
| ΔΔCt | | | | 10.05 |
| | 900 nM FwLoop5C | | | |
| Non-methylated | 1 | 27.20 ± 0.15 | >55.00 ± 0.00* | >27.80 |
| Methylated | 1 | 26.98 ± 0.23 | 45.15 ± 0.78 | 18.17 |
| ΔΔCt | | | | >9.62 |

*No signal detected

Example 9

Test of 1-Hold Methyl-Specific Amplification

MGMT_FwLoop5C was used to investigate a 1-step methyl-specific hold instead of methyl-specific pre-amplification. The assays were made as described in the section "Design of higher $T_m$ BasePrimer" with 500 nM FwLoop5C instead of 700 nM. PCR Program F was used (Table 15). The methyl-hold time was tested at 80° C. for 60 and 120 seconds.

TABLE 15

PCR Program F.

| PCR Program F | | Temperature [° C.] | Time [sec] | No. of cycles |
|---|---|---|---|---|
| Hold | | 95 | 120 | 1 |
| Methyl-hold | | 80 | 60 | 1 |
| 2-step Amplification | Step 1 | 95 | 30 | 60 |
| | Step 2 | 80 | 20* | |

*= acquiring stage (the stage where the fluorescence is acquired).

The 5 cycles methyl-specific amplification was changed to a methyl-hold to increase specificity of the BasePrimer. It was found that 80° C. for 60 seconds (see FIG. 11) was better than the 5-cycles methyl-specific amplification shown in table 14. The ΔΔCt was increased from 12.6 to 14.8. The raw data is presented in table 16.

TABLE 16

Result table of 5-cycles methyl-specific amplification vs 1-methyl hold

| Template | Conc [ng/μL] | Ref Ct | Loop4C Ct | ΔCt |
|---|---|---|---|---|
| 5-cycles methyl-specific amplification | | | | |
| Non-methylated | 1 | 27.20 ± 0.15 | 49.62 ± 1.22 | 22.41 |
| Methylated | 1 | 26.98 ± 0.23 | 36.76 ± 1.36 | 9.78 |
| ΔΔCt | | | | 12.63 |

TABLE 16-continued

| Result table of 5-cycles methyl-specific amplification vs 1-methyl hold | | | | |
|---|---|---|---|---|
| Template | Conc [ng/μL] | Ref Ct | Loop4C Ct | ΔCt |
| 1-methyl hold 80° C. 60 s | | | | |
| Non-methylated | 1 | 29.72 ± 0.14 | 52.89 ± 1.71 | 23.16 |
| Methylated | 1 | 30.48 ± 0.12 | 38.89 ± 0.52 | 8.41 |
| ΔΔCt | | | | 14.75 |
| 1-methyl hold 80° C. 120 s | | | | |
| Non-methylated | 1 | 29.65 ± 0.18 | 49.03 ± 3.36 | 19.38 |
| Methylated | 1 | 30.62 ± 0.08 | 38.83 ± 0.20 | 8.20 |
| ΔΔCt | | | | 11.18 |

Example 10

Validation of Method

The method was further validated using linearity and sensitivity studies and by evaluation of patient samples. All validation samples were tested in duplicates on PCR program F. The methyl-specific assay was made by mixing 500 nM of MGMT_FwLoop5C with 700 nM MGMT_Rev2C_suE. The reference assay was made by mixing 700 nM MGMT_Fw2C_suE with 700 nM Rev2C_suE. Master mix containing 1% ZUBR Green was used in both the reference and methyl-specific assay.

Linearity of Reference and Methyl-Specific Assay

Linearity studies were carried out on methylated template (DNA purified from SW1088 cells) and non-methylated template (purified DNA from blood, healthy patient). The templates were diluted to concentrations of 50, 25, 12.5, 6.25, 3.13, 1.56, 0.78 ng/μL, and added to both the reference and methyl-specific assay. Standard curves were fitted to the following equation (Kubista et al., 2006):

$$Ct = k \cdot \log(q) + CT \quad (1)$$

Where k is the slope, q is initial number of DNA molecules in the sample.

The PCR efficiency was calculated by the following equation (Kubista et al., 2006):

$$E = 10^{-\frac{1}{k}} - 1$$

The linearity was better for the reference assay compared to the methyl-specific assay. The linearity was better for non-methylated template ($R^2$=0.998) compared to methylated template ($R^2$=0.98) on the reference assay. The opposite was seen for the methyl-specific assay, here the linearity was best for the methylated template ($R^2$=0.873) compared to the non-methylated template ($R^2$=0.811), see FIG. 12.

The PCR efficiency was greater than 100% for the non-methylated template, and below 100% for the methylated template. This accounted for both the reference and methyl-specific assay (FwLoop5C). The results are found in table 17.

TABLE 17

| PCR efficiency reference and FwLoop5C assay on methylated and non-methylated DNA. | | | |
|---|---|---|---|
| Assay | Sample | Slope, k | Efficiency (%) |
| Ref | non.mC | −3.66 | 87.6 |
| Ref | mC | −2.71 | 133.9 |
| FwLoop5C | non.mC | −6.61 | 45.3 |
| FwLoop5C | mC | −1.83 | 251.9 |

Sensitivity of Methyl-Specific Assay

The sensitivity of the methyl-specific assay was analyzed by mixing 2 ng/μL of purified DNA from SW1088 with 2 ng/μL of purified DNA from blood from a healthy patient. Following concentrations were made: 100%, 50%, 25%, 10%, 5%, 1% and 0% methylation. The sensitivity was carried out on a MyGo Pro instrument.

Figure 13:
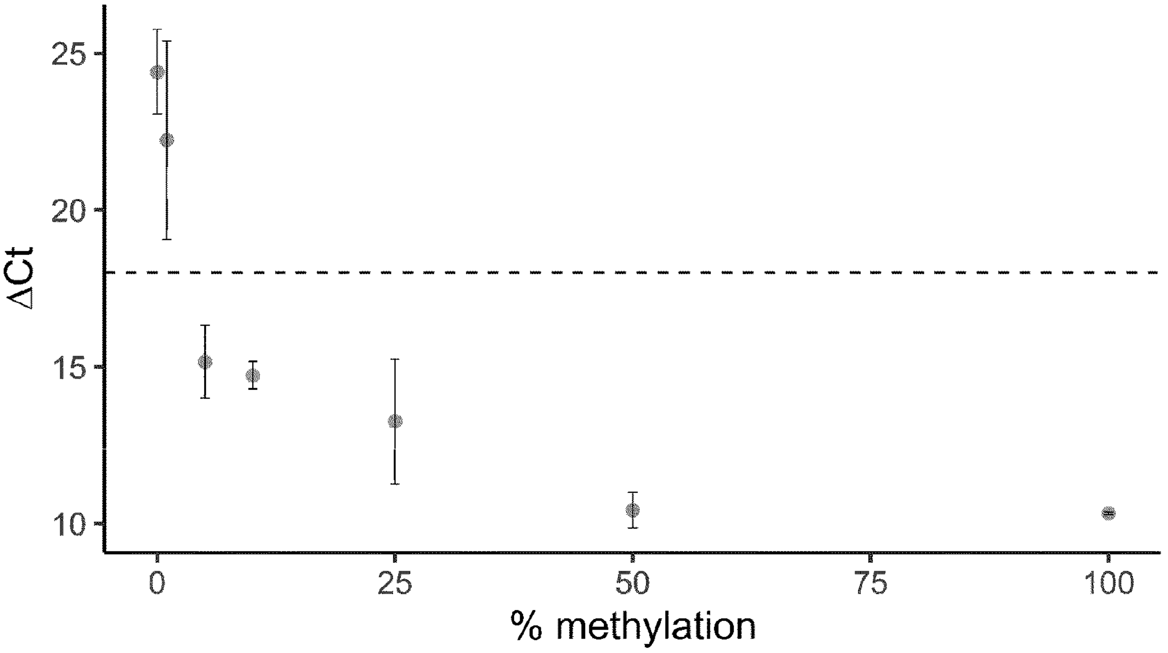

The sensitivity was 5%, and a clear differentiation between methylated and non-methylated DNA could be set at ΔCt=18. There was not observed linearity between % methylation and ΔCt (see FIG. 13).

From the results, suggestions could be made to roughly classify the patients as highly methylated, low methylated and unmethylated based on the ΔCt, see table 18.

TABLE 18

| Suggestion for classification of patient based on ΔCt. | | |
|---|---|---|
| Methylation | ΔCt | Estimated % methylation |
| U | >18 | 0% |
| M-Low | 12-18 | <50% |
| M-High | <12 | >50% |

Example 11

Melt Studies of Mutation (Mismatch) Probes

An extension of the melt studies was made by using MGMT_E probe and deliberately adding some mismatching nucleotides in the sequence. Two probes were made with two mutations (leading to two mismatches), and three probes were made with one mutation (leading to one mismatch). The sequences are found in table 20. The experimental set-up was the same as in the section "Affinity towards 5-methylcytosine"

TABLE 20

Probes with mutations (mismatches) tested with targets with and without methylated cytosine. C = non methylated cytosine. Underlined single letters = mutation (mismatch). Underlined mCs = 5-methylcytosine.

| SEQ ID NO: | Name | Sequence |
|---|---|---|
| | | Probes |
| 3 | MGMT_E | 5'-FAM-CEGTCCCEGACEGCCCEG-BHQ1-3' |
| 27 | MGMT_E_M1 | 5'-FAM-CEGACCCEGTCEGCCCEG-BHQ1-3' |
| 28 | MGMT_E_M2 | 5'-FAM-CEGTCACEGACEGCACEG-BHQ1-3' |
| 29 | MGMT_E_M3 | 5'-FAM-CEGTCACEGACEGCCCEG-BHQ1-3' |
| 30 | MGMT_E_M4 | 5'-FAM-CEGTCCCEGACEGCACEG-BHQ1-3' |
| 31 | MGMT_E_M5 | 5'-FAM-CEGACCCEGACEGCCCEG-BHQ1-3' |
| | | Targets |
| 7 | MGMT_0mC | 5'-CGGGCGTCGGGACG-3' |
| 8 | MGMT_1,2,3,4mC | 5'-mCGGGmCGTmCGGGAmCG-3' |

It was found that the probes with mismatches to the target sequence reduced the melting temperature of the duplexes without affecting the specificity ($\Delta T_m$) towards methylated DNA over non-methylated DNA, except for MGMT_E_M2 where a slight decrease in $\Delta T_m$ was observed. The results are shown in FIG. 14 and the raw data is presented in table 21. This experiment shows that it is possible to reduce the affinity of for example a methylation specific primer spanning several high affinity CpG sites, without reducing the specificity.

TABLE 21

Tm of MGMT_E mutation (mismatch) probes melted with targets containing 0 and 4 methylation sites.

| Probe | Rep | 0 mC [° C.] | 1, 2, 3, 4 mC [° C.] |
|---|---|---|---|
| MGMT_E | 1 | 74.34 | 84.10 |
| | 2 | 74.39 | 84.02 |
| | 3 | 74.32 | 84.31 |
| | Avg | 74.35 | 84.14 |
| | SDV | 0.03 | 0.12 |
| MGMT_E_M1 | 1 | 55.56 | 65.96 |
| | 2 | 55.67 | 64.74 |
| | 3 | 55.82 | 66.35 |
| | Avg | 55.68 | 65.68 |
| | SDV | 0.11 | 0.69 |
| MGMT_E_M2 | 1 | 65.40 | 72.47 |
| | 2 | 65.25 | 72.59 |
| | 3 | 65.37 | 74.78 |
| | Avg | 65.34 | 73.28 |
| | SDV | 0.07 | 1.06 |
| MGMT_E_M3 | 1 | 70.33 | 79.82 |
| | 2 | 70.17 | 79.84 |
| | 3 | 70.12 | 79.76 |
| | Avg | 70.21 | 79.80 |
| | SDV | 0.09 | 0.03 |
| MGMT_E_M4 | 1 | 69.77 | 78.88 |
| | 2 | 69.61 | 79.02 |
| | 3 | 69.75 | 79.13 |
| | Avg | 69.71 | 79.01 |
| | SDV | 0.07 | 0.10 |
| MGMT_E_M5 | 1 | 69.64 | 78.72 |
| | 2 | 69.19 | 78.98 |
| | 3 | 69.15 | 78.79 |
| | Avg | 69.33 | 78.83 |
| | SDV | 0.22 | 0.11 |

Example 12

Sensitivity of BasePrimer with a Single Mismatch in Anchor Sequence

A BasePrimer with a single mismatch in the anchor sequence was evaluated using a sensitivity study made on synthetic DNA from the MGMT promoter region. The synthetic DNA was methylated using CpG Methyltransferase (New England Biolabs Inc, Ipswich, MA, USA) following the manufactures protocol. Dilutions in a concentration of 500 copies/µL of fully methylated DNA and unmethylated DNA were mixed to achieve 100%, 50%, 25%, 12.5%, 6.3%, 3.1%, and 0% methylated template. 700 nM MGMT_Fw2C, 700 nM MGMT_Rev2E, and 500 nM MGMT_Probe2E were used for the reference assay, and for the methyl-specific assay, 700 nM MGMT_FwLoop5D_M5 was used instead of MGMT_Fw2C (see table 22 for sequences). The study was carried out on a BaseTyper™ real-time PCR instrument (PentaBase, Odense, Denmark) using PCR Program G (see table 23).

TABLE 22

BasePrimer design. Bold = anchor sequence. Standard letters = loop sequence. Underlined = 3'-end starter sequence. Bold & underlined = mismatch.

| SEQ ID NO: | Name | Sequence | Tm [° C.] |
|---|---|---|---|
| 32 | MGMT_ FwLoop5D_M5 | 5'- **CEGACCCEGACEGCCCEG**AGCGCTTC ACTGAGACAGGTCCTCGC-3' | 78.1 |
| 33 | MGMT_Rev2E | 5'-GAGCGAGGCGACCCAGACACTCA-3' | 71.5 |

TABLE 23

| PCR Program G. | | | | |
|---|---|---|---|---|
| PCR Program G | | Temperature [° C.] | Time [sec] | No. of cycles |
| Hold | | 98 | 120 | 1 |
| 2-step Amplification | Step 1 | 98 | 10 | 60 |
| | Step 2 | 76 | 60* | |

*= acquiring stage (the stage where the fluorescence is acquired).

The lowest detected sample contained 6.3% methylated DNA, and a linear correlation was observed between ΔCt and log (% methylation) (see FIG. 15). Based on the linear correlation, it is possible to quantify the degree of methylation based on the ΔCt-value.

Investigation of Number of Base Pairs Between Anchor and Starter Sequence

For the previous mentioned BasePrimers, the starter sequences were complementary to the target sequence in the immediate 3'-end of the anchor sequence. New BasePrimers with a single mismatch in the anchor sequence were designed with a gap of nucleotides between the 3'-end of the anchor sequence and the 5'-end of the starter sequence on the complementary target sequence (see FIG. 16). The BasePrimers were designed with a gap of 0, 2, 4, 6 and 8 nucleotides with two lengths of starter sequences (A and B), see table 24.

TABLE 24

BasePrimer designs. Bold = anchor sequence. Standard letters = loop sequence. Underlined = 3'-end starter sequence. Bold & underlined = mismatch.

| SEQ ID NO: | Name | Sequence | Tm [° C.] |
|---|---|---|---|
| 34 | MGMT_FwLoop5B_M5 | 5'- **CEGACCCEGACEGCCCEG**AGCGCTT CACTGAGACAGGTCCTCG-3' | 74.6 |
| 35 | MGMT_FwLoop5B_M5_2A | 5'- **CEGACCCEGACEGCCCEG**AGCGCTT CACTGAGAGGTCCTCGC-3' | 74.9 |
| 36 | MGMT_FwLoop5B_M5_2B | 5'- **CEGACCCEGACEGCCCEG**AGCGCTT CACTGAGAGGTCCTCG-3' | 73.3 |
| 37 | MGMT_FwLoop5B_M5_4A | 5'- **CEGACCCEGACEGCCCEG**AGCGCTT CACTGAGATCCTCGCGG-3' | 75.6 |
| 38 | MGMT_FwLoop5B_M5_4B | 5'- **CEGACCCEGACEGCCCEG**AGCGCTT CACTGAGATCCTCGCG-3' | 74.9 |
| 39 | MGMT_FwLoop5B_M5_6A | 5'- **CEGACCCEGACEGCCCEG**AGCGCTT CACTGAGACTCGCGGT-3' | 74.8 |
| 40 | MGMT_FwLoop5B_M5_6B | 5'- **CEGACCCEGACEGCCCEG**AGCGCTT CACTGAGACTCGCGG-3' | 74.5 |
| 41 | MGMT_FwLoop5B_M5_8A | 5'- **CEGACCCEGACEGCCCEG**AGCGCTT CACTGAGACGCGGT-3' | 73.0 |
| 42 | MGMT_FwLoop5B_M5_8B | 5'- **CEGACCCEGACEGCCCEG**AGCGCTT CACTGAGACGCGGTG-3' | 74.1 |

700 nM MGMT_Fw2C, 700 nM MGMT_Rev2E, and 500 nM MGMT_Probe2E were used for the reference assay, and for the methyl-specific assay, 700 nM of the BasePrimers listed in table 24 were used instead of MGMT_Fw2C. 500 copies/μL of non-methylated, 100% methylated, and 10% methylated synthetic DNA were used as template. The PCR was carried out using PCR Program H (see table 25) on a Base Typer.

TABLE 25

PCR Program H.

| PCR Program H | | Temperature [° C.] | Time [sec] | No. of cycles |
|---|---|---|---|---|
| Hold | | 98 | 120 | 1 |
| 2-step Amplification | Step 1 | 98 | 10 | 60 |
| | Step 2 | 75 | 30* | |

*= acquiring stage (the stage where the fluorescence is acquired).

It was found that all designs could discriminate between 100% mC, 10% mC and non.mC DNA except for MGMT_FwLoop5B_M5_8A and MGMT_FwLoop5B_M5_8B (see FIG. 17).

Example 13

Assisted Primer Complex

Another methyl-discriminating primer design was tested. The methyl-discriminating primer complex consists of an assist primer comprising an anchor sequence and a stem sequence. The other part of the complex is a regular primer, partly complementary to the assist primer's stem sequence and partly complementary to the target sequence. The discrimination of methylated DNA over non-methylated DNA occurs by the same principle as the BasePrimers. However, after the PCR has initiated on methylated DNA, the regular primer is used for the remaining cycles. The principle is illustrated in FIG. 18.

The assisted primer complex was tested on the sequences shown in table 26. 700 nM MGMT_Fw2C, 700 nM MGMT_Rev2E, and 500 nM MGMT_Probe2E were used for the reference assay, and for the methyl-specific assay, 700 nM of MGMT_Primer_1D and 50 nM of MGMT_Assist_1A_E were used instead of MGMT_Fw2C. 500 copies/μL of non-methylated and 100% methylated synthetic DNA were used as template. The PCR was carried out using PCR Program H (see Table 25) on a BaseTyper.

TABLE 26

Assisted primer design. Bold = anchor sequence. Standard letters = stem sequence. Underlined = 3'-end starter sequence. Bold & underlined = mismatch

| SEQ ID NO: | Name | Sequence | Tm [° C.] |
|---|---|---|---|
| 32 | MGMT_Assist_1A_E | 5'-**CEGACCCEGACEGCCCEG**AAGCTEG TACCACTEGAGAEGTCC-3' | N/A |
| 33 | MGMT_Primer_1D | 5'-GGACTCTCAGTGGTACAGCTTCAGGT CCTCGC-3' | 75.8 |

The PCR curves are shown in FIG. 19. The ΔCt was 5.6 for 100% methylated DNA and 9.5 for non-methylated DNA giving a ΔΔCt of 3.9.

The invention claimed is:

1. A method of determining methylation status, of at least one nucleotide of interest (NOI) in a non-modified target nucleic acid sequence of interest, wherein said target nucleic acid sequence comprises a target anchor sequence comprising said NOI, said method comprising the steps of a) providing an oligonucleotide comprising an anchor sequence (An), wherein the anchor sequence is a sequence at least 50% complementary to said target anchor sequence, wherein the anchor sequence comprises at least one hydrophobic nucleotide (H) positioned between the nucleotide complementary to said NOI and the nucleotide immediately 5' thereof;

b) incubating said oligonucleotide with said target nucleic acid sequence of interest at a temperature which is higher than the melting temperature between said oligonucleotide and the target nucleic acid sequence of interest when said NOI is unmethylated, c) detecting whether said oligonucleotide anneals to said target nucleic acid sequence of interest, thereby determining the methylation status, wherein i) said hydrophobic nucleotide (H) has the structure $$X—Y—Q,$$

wherein

X is a nucleotide or nucleotide analogue or a backbone monomer unit capable of being incorporated into the backbone of a nucleic acid or nucleic acid analogue;

Q is an intercalator which is not taking part in Watson-Crick hydrogen bonding; and Y is a linker moiety linking said nucleotide or nucleotide analogue or backbone monomer unit and said intercalator; and ii) said oligonucleotide has the structure 5'-An-Lp-St-3', wherein An is the anchor sequence;

Lp is a loop sequence, which is not complementary to the target nucleic acid sequence of interest, wherein the loop sequence consists of a single nucleic acid sequence capable of forming a protruding structure, or consists of two or more nucleic acid sequences capable of hybridising at least partly to one another to form a complex which is capable of forming a protruding structure;

St is a starter sequence, capable of hybridizing to a target starter sequence, wherein the target starter sequence is a sequence of the target nucleic acid sequence positioned 5' to the target anchor sequence.

2. The method according to claim 1, wherein the target nucleic acid sequence of interest is DNA or RNA.

3. The method according to claim 1, wherein the non-modified nucleic acid sequence of interest has not been subjected to treatment comprising bisulfite conversion, restriction enzyme digestion or TET enzymatic conversion prior to performing the method.

4. The method according to claim 1, wherein the NOI is a cytosine.

5. The method according to claim 1, wherein the difference between

A) the absolute difference between the melting temperatures of i) the oligonucleotide comprising said hydrophobic nucleotide(s) when hybridized to said target nucleic acid sequence of interest, wherein said nucleic acid sequence of interest comprises at least one methylated NOI; and ii) the oligonucleotide comprising said hydrophobic nucleotide(s) when hybridized to said target nucleic acid sequence of interest, wherein said nucleic acid sequence of interest comprises no methylated NOIs; and B) the absolute difference between the melting temperatures of i) an oligonucleotide identical to the oligonucleotide of A), but lacking said hydrophobic nucleotide(s), when hybridized to said target nucleic acid sequence of interest, wherein said nucleic acid sequence of interest comprises the same number of methylated NOIs as in A)(i); and ii) an oligonucleotide identical to the oligonucleotide of A), but lacking said hydrophobic nucleotide(s), when hybridized to said target nucleic acid sequence of interest, wherein said nucleic acid sequence of interest comprises no methylated NOIs, is at least 0.50° C., wherein the difference is A-B and wherein the difference is a positive difference, and wherein the melting temperature is measured in TM buffer comprising 0.02 M $Na_2HPO_4$, 0.02 M NaCl, and 2 mM EDTA.

6. The method according to claim 1, wherein the anchor sequence comprises at least one -N-H-G- sequence, wherein each-G-is complementary to a cytosine of interest and each -N- is individually selected from the group consisting of C, G, A and T and is complementary to the neighbouring nucleotide of said cytosine of interest.

7. The method according to claim 1, wherein steps b) and c) together comprise performing a PCR, wherein said temperature is used as the annealing temperature in one or more cycles of said PCR.

8. The method according to claim 1, wherein said oligonucleotide consists of a first and a second nucleic acid sequences, wherein the first nucleic acid sequence comprises the anchor sequence (An) complementary to the target DNA and a first part of a loop sequence not complementary to the target nucleic acid sequence of interest, and the second nucleic acid sequence comprises a second part of the loop sequence, capable of hybridising at least partly to the first part of the loop sequence, said second nucleic acid sequence further comprising the starter sequence (St), and wherein the first and the second nucleic acids once hybridized are capable of forming the protruding structure.

9. The method according to claim 1, wherein the target anchor sequence and the target starter sequence are positioned within 10 nucleotides from each other.

10. The method according to claim 1, wherein Lp and St are selected such that an oligonucleotide consisting of Lp-St has a melting temperature with its complementary sequence of at least 50° C.

11. The method according to claim 1, wherein the difference in melting temperature between said oligonucleotide and the methylated target nucleic acid sequence of interest is at least 5° C. higher than the difference in melting temperature between said oligonucleotide and the unmethylated target nucleic acid sequence of interest.

12. The method according to claim 1, wherein the difference in melting temperature between said oligonucleotide and the methylated target nucleic acid sequence compared to an unmethylated target nucleic acid sequence of interest is at least 1° C. higher than the difference in melting temperature between an oligonucleotide of identical sequence lacking the hydrophobic nucleotides and the methylated target nucleic acid sequence compared to an unmethylated target nucleic acid sequence.

13. The method according to claim 7, wherein said PCR comprises one or more methyl-specific amplification cycles and one or more general amplification cycles, wherein the methyl specific amplification cycle(s) comprise the steps of d) melting nucleic acids e) annealing and extension under methyl specific conditions and the general amplification cycles comprise the steps of f) melting nucleic acids g) annealing and extension under general conditions wherein the melting comprises incubation at a temperature of at least 90° C., and wherein the annealing and extension under methyl specific conditions is performed at a higher temperature than annealing and extension under general conditions.

14. The method according to claim 7, wherein said PCR is performed using said oligonucleotide as forward primer, wherein said PCR further comprises use of a reverse primer at least 90% identical to a sequence downstream of said target nucleic acid sequence of interest.

15. The method according to claim 1, wherein target nucleic acid sequence of interest is comprised in DNA purified from a sample obtained from an individual suffering from or at risk of having a clinical condition associated with methylation in the nucleic acid of interest.

16. A method for determining the risk of whether an individual suffers from a clinical condition, or the risk of an individual to contract a clinical condition, or determining the likelihood of effect of a treatment of a clinical condition in an individual, wherein the clinical condition is associated with the methylation status of a NOI in a nucleic acid of interest, said method comprising:

a) providing a sample obtained from said individual; and b) determining the methylation status of said NOI in said sample by performing the method according to claim 1, wherein said methylation status is indicative of the presence of or risk of contracting said clinical condition or of the effects of different treatment regimens on said clinical condition.

17. The method according to claim 1, said oligonucleotide comprising or consisting of the following general structure:

$$5'(N)_n\text{—HG—}(N)_m\text{—HG—}(N)_p\text{—HG—}(N)_q\text{-}3',$$

wherein N is any nucleotide or nucleotide analogue; and
G is the nucleotide guanine; and
n is an integer≥0; and
m is an integer≥1; and
p is an integer≥1; and
q is an integer≥0; and
H is a hydrophobic nucleotide; or $$5'(N)_n\text{—CGH—}(N)_m\text{—CGH—}(N)_p\text{-}3',$$

wherein N is any nucleotide or nucleotide analogue; and
C is the nucleotide cytosine; and
G is the nucleotide guanine; and
n is an integer≥0; and
m is an integer≥1; and
p is an integer≥0; and
H is a hydrophobic nucleotide wherein said hydrophobic nucleotide has the structure

X—Y—Q wherein

X is a nucleotide or nucleotide analogue or a backbone monomer unit capable of being incorporated into the backbone of a nucleic acid or nucleic acid analogue, Q is an intercalator which is not taking part in Watson-Crick hydrogen bonding; and Y is a linker moiety linking said nucleotide or nucleotide analogue or backbone monomer unit and said intercalator.

18. The method according to claim 17, wherein the oligonucleotide comprises or consists of the following general structure:

$$5'(N)_n—HG—(N)_m—HG—(N)_p—HG—(N)_q—HG—(N)_u\text{-}3',$$

or $$5'(N)_n—CGH—(N)_m—CGH—(N)_p—CGH—(N)_q—CGH—(N)_u\text{-}3',$$

wherein q is an integer≥1; and u is an integer≥0.

19. The method according to claim 17, wherein the nucleotide located immediately 5' to at least one H is a cytosine (C).

* * * * *

SEQUENCE LISTING

<160> NUMBER OF SEQ ID NOS: 42

<210> SEQ ID NO 1
<211> LENGTH: 266
<212> TYPE: DNA
<213> ORGANISM: Homo sapiens

<400> SEQUENCE: 1
ctcttgcttt tctcaggtcc tcggctccgc cccgctctag accccgcccc acgccgccat 60
ccccgtgccc ctcggccccg cccccgcgcc ccggatatgc tgggacagcc cgcgccccta 120
gaacgctttg cgtcccgacg cccgcaggtc ctcgcggtgc gcaccgtttg cgacttggtg 180
agtgtctggg tcgcctcgct cccggaagag tgcggagctc tccctcggga cggtggcagc 240
ctcgagtggt cctgcaggcg ccctca 266

<210> SEQ ID NO 2
<211> LENGTH: 18
<212> TYPE: DNA
<213> ORGANISM: Artificial sequence
<220> FEATURE:

-continued

<223> OTHER INFORMATION: MGMT_Z Probe
<220> FEATURE:
<221> NAME/KEY: misc_feature
<222> LOCATION: (2)..(2)
<223> OTHER INFORMATION: Hydrophobic nucleotide of type Z
(Phosphoramidite of 3-(1-O-(4,4'-dimethoxytriphenylmetyl)-2-O-(2-
cyanoethyl diisopropylamidophosphite)-1,2-butandiol)-4-N-(7,9-
Dimethyl-3H-pyrido[3',2':4,5]thieno[3,2-d]pyrimidin-4-on
<220> FEATURE:
<221> NAME/KEY: misc_feature
<222> LOCATION: (8)..(8)
<223> OTHER INFORMATION: Hydrophobic nucleotide of type Z
(Phosphoramidite of 3-(1-O-(4,4'-dimethoxytriphenylmetyl)-2-O-(2-
cyanoethyl diisopropylamidophosphite)-1,2-butandiol)-4-N-(7,9-
Dimethyl-3H-pyrido[3',2':4,5]thieno[3,2-d]pyrimidin-4-on
<220> FEATURE:
<221> NAME/KEY: misc_feature
<222> LOCATION: (12)..(12)
<223> OTHER INFORMATION: Hydrophobic nucleotide of type Z
(Phosphoramidite of 3-(1-O-(4,4'-dimethoxytriphenylmetyl)-2-O-(2-
cyanoethyl diisopropylamidophosphite)-1,2-butandiol)-4-N-(7,9-
Dimethyl-3H-pyrido[3',2':4,5]thieno[3,2-d]pyrimidin-4-on
<220> FEATURE:
<221> NAME/KEY: misc_feature
<222> LOCATION: (17)..(17)
<223> OTHER INFORMATION: Hydrophobic nucleotide of type Z
(Phosphoramidite of 3-(1-O-(4,4'-dimethoxytriphenylmetyl)-2-O-(2-
cyanoethyl diisopropylamidophosphite)-1,2-butandiol)-4-N-(7,9-
Dimethyl-3H-pyrido[3',2':4,5]thieno[3,2-d]pyrimidin-4-on

<400> SEQUENCE: 2
cngtcccnga cngcccng 18

<210> SEQ ID NO 3
<211> LENGTH: 18
<212> TYPE: DNA
<213> ORGANISM: Artificial sequence
<220> FEATURE:
<223> OTHER INFORMATION: MGMT_E Probe
<220> FEATURE:
<221> NAME/KEY: misc_feature
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<400> SEQUENCE: 3
cngtcccnga cngcccng 18

<210> SEQ ID NO 4
<211> LENGTH: 18
<212> TYPE: DNA
<213> ORGANISM: Artificial sequence
<220> FEATURE:
<223> OTHER INFORMATION: MGMT_E2 Probe
<220> FEATURE:
<221> NAME/KEY: misc_feature

```
<222> LOCATION: (1)..(1)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)
<220> FEATURE:
<221> NAME/KEY: misc_feature
<222> LOCATION: (7)..(7)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)
<220> FEATURE:
<221> NAME/KEY: misc_feature
<222> LOCATION: (11)..(11)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)
<220> FEATURE:
<221> NAME/KEY: misc_feature
<222> LOCATION: (16)..(16)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)

<400> SEQUENCE: 4

ncgtccncga ncgccncg                                                   18


<210> SEQ ID NO 5
<211> LENGTH: 18
<212> TYPE: DNA
<213> ORGANISM: Artificial sequence
<220> FEATURE:
<223> OTHER INFORMATION: MGMT_E3 Probe
<220> FEATURE:
<221> NAME/KEY: misc_feature
<222> LOCATION: (3)..(3)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)
<220> FEATURE:
<221> NAME/KEY: misc_feature
<222> LOCATION: (9)..(9)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)
<220> FEATURE:
<221> NAME/KEY: misc_feature
<222> LOCATION: (13)..(13)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)
<220> FEATURE:
<221> NAME/KEY: misc_feature
<222> LOCATION: (18)..(18)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)

<400> SEQUENCE: 5

cgntcccgna cgncccgn                                                   18


<210> SEQ ID NO 6
<211> LENGTH: 14
<212> TYPE: DNA
<213> ORGANISM: Artificial sequence
<220> FEATURE:
<223> OTHER INFORMATION: MGMT_Ref Probe
<220> FEATURE:
<221> NAME/KEY: misc_feature
<222> LOCATION: (1)..(14)
<223> OTHER INFORMATION: Probe

<400> SEQUENCE: 6

cgtcccgacg cccg                                                       14
```

<210> SEQ ID NO 7
<211> LENGTH: 14
<212> TYPE: DNA
<213> ORGANISM: Artificial sequence
<220> FEATURE:
<223> OTHER INFORMATION: MGMT_0mC Target
<220> FEATURE:
<221> NAME/KEY: misc_feature
<222> LOCATION: (1)..(14)
<223> OTHER INFORMATION: Target

<400> SEQUENCE: 7
cgggcgtcgg gacg 14

<210> SEQ ID NO 8
<211> LENGTH: 14
<212> TYPE: DNA
<213> ORGANISM: Artificial sequence
<220> FEATURE:
<223> OTHER INFORMATION: MGMT_1,2,3,4mC Target
<220> FEATURE:
<221> NAME/KEY: misc_feature
<222> LOCATION: (1)..(1)
<223> OTHER INFORMATION: Methylated nucleotide
<220> FEATURE:
<221> NAME/KEY: misc_feature
<222> LOCATION: (5)..(5)
<223> OTHER INFORMATION: Methylated nucleotide
<220> FEATURE:
<221> NAME/KEY: misc_feature
<222> LOCATION: (8)..(8)
<223> OTHER INFORMATION: Methylated nucleotide
<220> FEATURE:
<221> NAME/KEY: misc_feature
<222> LOCATION: (13)..(13)
<223> OTHER INFORMATION: Methylated nucleotide

<400> SEQUENCE: 8
cgggcgtcgg gacg 14

<210> SEQ ID NO 9
<211> LENGTH: 14
<212> TYPE: DNA
<213> ORGANISM: Artificial sequence
<220> FEATURE:
<223> OTHER INFORMATION: MGMT_1mC Target
<220> FEATURE:
<221> NAME/KEY: misc_feature
<222> LOCATION: (1)..(1)
<223> OTHER INFORMATION: Methylated nucleotide

<400> SEQUENCE: 9
cgggcgtcgg gacg 14

<210> SEQ ID NO 10
<211> LENGTH: 14
<212> TYPE: DNA
<213> ORGANISM: Artificial sequence
<220> FEATURE:
<223> OTHER INFORMATION: MGMT_2mC Target
<220> FEATURE:
<221> NAME/KEY: misc_feature
<222> LOCATION: (5)..(5)
<223> OTHER INFORMATION: Methylated nucleotide

<400> SEQUENCE: 10
cgggcgtcgg gacg 14

<210> SEQ ID NO 11
<211> LENGTH: 14

<212> TYPE: DNA
<213> ORGANISM: Artificial sequence
<220> FEATURE:
<223> OTHER INFORMATION: MGMT_3mC Target
<220> FEATURE:
<221> NAME/KEY: misc_feature
<222> LOCATION: (8)..(8)
<223> OTHER INFORMATION: Methylated nucleotide

<400> SEQUENCE: 11
cgggcgtcgg gacg 14

<210> SEQ ID NO 12
<211> LENGTH: 14
<212> TYPE: DNA
<213> ORGANISM: Artificial sequence
<220> FEATURE:
<223> OTHER INFORMATION: MGMT_4mC Target
<220> FEATURE:
<221> NAME/KEY: misc_feature
<222> LOCATION: (13)..(13)
<223> OTHER INFORMATION: Methylated nucleotide

<400> SEQUENCE: 12
cgggcgtcgg gacg 14

<210> SEQ ID NO 13
<211> LENGTH: 14
<212> TYPE: DNA
<213> ORGANISM: Artificial sequence
<220> FEATURE:
<223> OTHER INFORMATION: MGMT_2,3mC Target
<220> FEATURE:
<221> NAME/KEY: misc_feature
<222> LOCATION: (5)..(5)
<223> OTHER INFORMATION: Methylated nucleotide
<220> FEATURE:
<221> NAME/KEY: misc_feature
<222> LOCATION: (8)..(8)
<223> OTHER INFORMATION: Methylated nucleotide

<400> SEQUENCE: 13
cgggcgtcgg gacg 14

<210> SEQ ID NO 14
<211> LENGTH: 38
<212> TYPE: DNA
<213> ORGANISM: Artificial sequence
<220> FEATURE:
<223> OTHER INFORMATION: MGMT_FwLoop3B BasePrimer
<220> FEATURE:
<221> NAME/KEY: misc_feature
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-pyrenemethyloxy-2-propanol)

<400> SEQUENCE: 14
cngtcccnga cngcccngag gcttctgaca ggtcctcg 38

<210> SEQ ID NO 15
<211> LENGTH: 40
<212> TYPE: DNA
<213> ORGANISM: Artificial sequence
<220> FEATURE:
<223> OTHER INFORMATION: MGMT_FwLoop3C BasePrimer
<220> FEATURE:
<221> NAME/KEY: misc_feature
<222> LOCATION: (2)..(2)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)

<400> SEQUENCE: 15
cngtcccnga cngcccngag gcttctgaca ggtcctcgcg 40

<210> SEQ ID NO 16
<211> LENGTH: 40
<212> TYPE: DNA
<213> ORGANISM: Artificial sequence
<220> FEATURE:
<223> OTHER INFORMATION: MGMT_FwLoop4B BasePrimer
<220> FEATURE:
<221> NAME/KEY: misc_feature
<222> LOCATION: (2)..(2)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)

<400> SEQUENCE: 16
cngtcccnga cngcccngag gcttcactga caggtcctcg 40

<210> SEQ ID NO 17
<211> LENGTH: 42
<212> TYPE: DNA
<213> ORGANISM: Artificial sequence
<220> FEATURE:
<223> OTHER INFORMATION: MGMT_FwLoop4C BasePrimer
<220> FEATURE:
<221> NAME/KEY: misc_feature
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<400> SEQUENCE: 17
cngtcccnga cngcccngag gcttcactga caggtcctcg cg 42

<210> SEQ ID NO 18
<211> LENGTH: 24
<212> TYPE: DNA
<213> ORGANISM: Artificial sequence
<220> FEATURE:
<223> OTHER INFORMATION: MGMT_Fw2C Primer
<220> FEATURE:
<221> NAME/KEY: misc_feature
<222> LOCATION: (1)..(24)
<223> OTHER INFORMATION: Primer

<400> SEQUENCE: 18
cgcccctaga acgctttgcg tccc 24

<210> SEQ ID NO 19
<211> LENGTH: 24
<212> TYPE: DNA
<213> ORGANISM: Artificial sequence
<220> FEATURE:
<223> OTHER INFORMATION: MGMT_Rev2C Primer
<220> FEATURE:
<221> NAME/KEY: misc_feature
<222> LOCATION: (1)..(24)
<223> OTHER INFORMATION: Primer

<400> SEQUENCE: 19
ggagcgaggc gacccagaca ctca 24

<210> SEQ ID NO 20
<211> LENGTH: 19
<212> TYPE: DNA
<213> ORGANISM: Artificial sequence
<220> FEATURE:
<223> OTHER INFORMATION: MGMT_Probe2A
<220> FEATURE:
<221> NAME/KEY: misc_feature
<222> LOCATION: (7)..(7)
<223> OTHER INFORMATION: Hydrophobic nucleotide of type Z
(Phosphoramidite of 3-(1-O-(4,4'-dimethoxytriphenylmetyl)-2-O-(2-

-continued cyanoethyl diisopropylamidophosphite)-1,2-butandiol)-4-N-(7,9-
Dimethyl-3H-pyrido[3',2':4,5]thieno[3,2-d]pyrimidin-4-on
<220> FEATURE:
<221> NAME/KEY: misc_feature
<222> LOCATION: (14)..(14)
<223> OTHER INFORMATION: Hydrophobic nucleotide of type Z
(Phosphoramidite of 3-(1-O-(4,4'-dimethoxytriphenylmetyl)-2-O-(2-
cyanoethyl diisopropylamidophosphite)-1,2-butandiol)-4-N-(7,9-
Dimethyl-3H-pyrido[3',2':4,5]thieno[3,2-d]pyrimidin-4-on
<220> FEATURE:
<221> NAME/KEY: misc_feature
<222> LOCATION: (18)..(18)
<223> OTHER INFORMATION: Hydrophobic nucleotide of type Z
(Phosphoramidite of 3-(1-O-(4,4'-dimethoxytriphenylmetyl)-2-O-(2-
cyanoethyl diisopropylamidophosphite)-1,2-butandiol)-4-N-(7,9-
Dimethyl-3H-pyrido[3',2':4,5]thieno[3,2-d]pyrimidin-4-on

<400> SEQUENCE: 20
caagtcngca aacnggtng 19

<210> SEQ ID NO 21
<211> LENGTH: 19
<212> TYPE: DNA
<213> ORGANISM: Artificial sequence
<220> FEATURE:
<223> OTHER INFORMATION: MGMT_Probe2B
<220> FEATURE:
<221> NAME/KEY: misc_feature
<222> LOCATION: (9)..(9)
<223> OTHER INFORMATION: Hydrophobic nucleotide of type Z
(Phosphoramidite of 3-(1-O-(4,4'-dimethoxytriphenylmetyl)-2-O-(2-
cyanoethyl diisopropylamidophosphite)-1,2-butandiol)-4-N-(7,9-
Dimethyl-3H-pyrido[3',2':4,5]thieno[3,2-d]pyrimidin-4-on
<220> FEATURE:
<221> NAME/KEY: misc_feature
<222> LOCATION: (14)..(14)
<223> OTHER INFORMATION: Hydrophobic nucleotide of type Z
(Phosphoramidite of 3-(1-O-(4,4'-dimethoxytriphenylmetyl)-2-O-(2-
cyanoethyl diisopropylamidophosphite)-1,2-butandiol)-4-N-(7,9-
Dimethyl-3H-pyrido[3',2':4,5]thieno[3,2-d]pyrimidin-4-on
<220> FEATURE:
<221> NAME/KEY: misc_feature
<222> LOCATION: (18)..(18)
<223> OTHER INFORMATION: Hydrophobic nucleotide of type Z
(Phosphoramidite of 3-(1-O-(4,4'-dimethoxytriphenylmetyl)-2-O-(2-
cyanoethyl diisopropylamidophosphite)-1,2-butandiol)-4-N-(7,9-
Dimethyl-3H-pyrido[3',2':4,5]thieno[3,2-d]pyrimidin-4-on

<400> SEQUENCE: 21
caagtcgcna aacnggtng 19

<210> SEQ ID NO 22
<211> LENGTH: 21
<212> TYPE: DNA
<213> ORGANISM: Artificial sequence
<220> FEATURE:
<223> OTHER INFORMATION: MGMT_Probe2D
<220> FEATURE:
<221> NAME/KEY: misc_feature
<222> LOCATION: (9)..(9)
<223> OTHER INFORMATION: Hydrophobic nucleotide of type Z
(Phosphoramidite of 3-(1-O-(4,4'-dimethoxytriphenylmetyl)-2-O-(2-
cyanoethyl diisopropylamidophosphite)-1,2-butandiol)-4-N-(7,9-
Dimethyl-3H-pyrido[3',2':4,5]thieno[3,2-d]pyrimidin-4-on
<220> FEATURE:
<221> NAME/KEY: misc_feature
<222> LOCATION: (14)..(14)
<223> OTHER INFORMATION: Hydrophobic nucleotide of type Z
(Phosphoramidite of 3-(1-O-(4,4'-dimethoxytriphenylmetyl)-2-O-(2-
cyanoethyl diisopropylamidophosphite)-1,2-butandiol)-4-N-(7,9-
Dimethyl-3H-pyrido[3',2':4,5]thieno[3,2-d]pyrimidin-4-on
<220> FEATURE:
<221> NAME/KEY: misc_feature
<222> LOCATION: (20)..(20)
<223> OTHER INFORMATION: Hydrophobic nucleotide of type Z (Phosphoramidite of 3-(1-O-(4,4'-dimethoxytriphenylmetyl)-2-O-(2-cyanoethyl diisopropylamidophosphite)-1,2-butandiol)-4-N-(7,9-Dimethyl-3H-pyrido[3',2':4,5]thieno[3,2-d]pyrimidin-4-on

<400> SEQUENCE: 22
caagtcgcna aacnggtgcn g 21

<210> SEQ ID NO 23
<211> LENGTH: 24
<212> TYPE: DNA
<213> ORGANISM: Artificial sequence
<220> FEATURE:
<223> OTHER INFORMATION: MGMT_Probe2E
<220> FEATURE:
<221> NAME/KEY: misc_feature
<222> LOCATION: (9)..(9)
<223> OTHER INFORMATION: Hydrophobic nucleotide of type Z (Phosphoramidite of 3-(1-O-(4,4'-dimethoxytriphenylmetyl)-2-O-(2-cyanoethyl diisopropylamidophosphite)-1,2-butandiol)-4-N-(7,9-Dimethyl-3H-pyrido[3',2':4,5]thieno[3,2-d]pyrimidin-4-on
<220> FEATURE:
<221> NAME/KEY: misc_feature
<222> LOCATION: (14)..(14)
<223> OTHER INFORMATION: Hydrophobic nucleotide of type Z (Phosphoramidite of 3-(1-O-(4,4'-dimethoxytriphenylmetyl)-2-O-(2-cyanoethyl diisopropylamidophosphite)-1,2-butandiol)-4-N-(7,9-Dimethyl-3H-pyrido[3',2':4,5]thieno[3,2-d]pyrimidin-4-on
<220> FEATURE:
<221> NAME/KEY: misc_feature
<222> LOCATION: (20)..(20)
<223> OTHER INFORMATION: Hydrophobic nucleotide of type Z (Phosphoramidite of 3-(1-O-(4,4'-dimethoxytriphenylmetyl)-2-O-(2-cyanoethyl diisopropylamidophosphite)-1,2-butandiol)-4-N-(7,9-Dimethyl-3H-pyrido[3',2':4,5]thieno[3,2-d]pyrimidin-4-on

<400> SEQUENCE: 23
caagtcgcna aacnggtgcn gcac 24

<210> SEQ ID NO 24
<211> LENGTH: 45
<212> TYPE: DNA
<213> ORGANISM: Artificial sequence
<220> FEATURE:
<223> OTHER INFORMATION: MGMT_FwLoop5C BasePrimer
<220> FEATURE:
<221> NAME/KEY: misc_feature
<222> LOCATION: (2)..(2)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)

<400> SEQUENCE: 24
cngtcccnga cngcccngag cgcttcactg agacaggtcc tcgcg 45

<210> SEQ ID NO 25

<211> LENGTH: 25
<212> TYPE: DNA
<213> ORGANISM: Artificial sequence
<220> FEATURE:
<223> OTHER INFORMATION: MGMT_Fw2C_suE Primer
<220> FEATURE:
<221> NAME/KEY: misc_feature
<222> LOCATION: (1)..(1)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)

<400> SEQUENCE: 25
ncgcccctag aacgctttgc gtccc 25

<210> SEQ ID NO 26
<211> LENGTH: 25
<212> TYPE: DNA
<213> ORGANISM: Artificial sequence
<220> FEATURE:
<223> OTHER INFORMATION: MGMT_Rev2C_suE Primer
<220> FEATURE:
<221> NAME/KEY: misc_feature
<222> LOCATION: (1)..(1)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)

<400> SEQUENCE: 26
nggagcgagg cgacccagac actca 25

<210> SEQ ID NO 27
<211> LENGTH: 18
<212> TYPE: DNA
<213> ORGANISM: Artificial sequence
<220> FEATURE:
<223> OTHER INFORMATION: MGMT_E_M1
<220> FEATURE:
<221> NAME/KEY: misc_feature
<222> LOCATION: (2)..(2)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)

<400> SEQUENCE: 27
cngacccngt cngcccng 18

<210> SEQ ID NO 28
<211> LENGTH: 18
<212> TYPE: DNA
<213> ORGANISM: Artificial sequence
<220> FEATURE:
<223> OTHER INFORMATION: MGMT_E_M2
<220> FEATURE:
<221> NAME/KEY: misc_feature -continued
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<400> SEQUENCE: 28
cngtcacnga cngcacng 18

<210> SEQ ID NO 29
<211> LENGTH: 18
<212> TYPE: DNA
<213> ORGANISM: Artificial sequence
<220> FEATURE:
<223> OTHER INFORMATION: MGMT_E_M3
<220> FEATURE:
<221> NAME/KEY: misc_feature
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<400> SEQUENCE: 29
cngtcacnga cngcccng 18

<210> SEQ ID NO 30
<211> LENGTH: 18
<212> TYPE: DNA
<213> ORGANISM: Artificial sequence
<220> FEATURE:
<223> OTHER INFORMATION: MGMT_E_M4
<220> FEATURE:
<221> NAME/KEY: misc_feature
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)

<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<400> SEQUENCE: 30
cngtcccnga cngcacng 18

<210> SEQ ID NO 31
<211> LENGTH: 18
<212> TYPE: DNA
<213> ORGANISM: Artificial sequence
<220> FEATURE:
<223> OTHER INFORMATION: MGMT_E_M5
<220> FEATURE:
<221> NAME/KEY: misc_feature
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<400> SEQUENCE: 31
cngacccnga cngcccng 18

<210> SEQ ID NO 32
<211> LENGTH: 44
<212> TYPE: DNA
<213> ORGANISM: Artificial
<220> FEATURE:
<223> OTHER INFORMATION: MGMT_FwLoop5D_M5
<220> FEATURE:
<221> NAME/KEY: misc_feature
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)

<400> SEQUENCE: 32
cngacccnga cngcccngag cgcttcactg agacaggtcc tcgc 44

<210> SEQ ID NO 33
<211> LENGTH: 23
<212> TYPE: DNA
<213> ORGANISM: Artificial
<220> FEATURE:
<223> OTHER INFORMATION: MGMT_Rev2E

<400> SEQUENCE: 33
gagcgaggcg acccagacac tca 23

<210> SEQ ID NO 34
<211> LENGTH: 43
<212> TYPE: DNA
<213> ORGANISM: Artificial
<220> FEATURE:
<223> OTHER INFORMATION: MGMT_FwLoop5B_M5
<220> FEATURE:
<221> NAME/KEY: misc_feature
<222> LOCATION: (2)..(2)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)

<400> SEQUENCE: 34
cngacccnga cngcccngag cgcttcactg agacaggtcc tcg 43

<210> SEQ ID NO 35
<211> LENGTH: 42
<212> TYPE: DNA
<213> ORGANISM: Artificial
<220> FEATURE:
<223> OTHER INFORMATION: MGMT_FwLoop5B_M5_2A
<220> FEATURE:
<221> NAME/KEY: misc_feature
<222> LOCATION: (2)..(2)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E (Phosphoramidite of (S)-1-(4,4'-dimethoxytriphenylmetyloxy)-3-

-continued pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<400> SEQUENCE: 35
cngacccnga cngcccngag cgcttcactg agaggtcctc gc 42

<210> SEQ ID NO 36
<211> LENGTH: 41
<212> TYPE: DNA
<213> ORGANISM: Artificial
<220> FEATURE:
<223> OTHER INFORMATION: MGMT_FwLoop5B_M5_2B
<220> FEATURE:
<221> NAME/KEY: misc_feature
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<400> SEQUENCE: 36
cngacccnga cngcccngag cgcttcactg agaggtcctc g 41

<210> SEQ ID NO 37
<211> LENGTH: 42
<212> TYPE: DNA
<213> ORGANISM: Artificial
<220> FEATURE:
<223> OTHER INFORMATION: MGMT_FwLoop5B_M5_4A
<220> FEATURE:
<221> NAME/KEY: misc_feature
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<400> SEQUENCE: 37
cngacccnga cngcccngag cgcttcactg agatcctcgc gg 42

<210> SEQ ID NO 38
<211> LENGTH: 41
<212> TYPE: DNA
<213> ORGANISM: Artificial
<220> FEATURE:
<223> OTHER INFORMATION: MGMT_FwLoop5B_M5_4B
<220> FEATURE:
<221> NAME/KEY: misc_feature
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<400> SEQUENCE: 38
cngacccnga cngcccngag cgcttcactg agatcctcgc g 41

<210> SEQ ID NO 39
<211> LENGTH: 41
<212> TYPE: DNA
<213> ORGANISM: Artificial
<220> FEATURE:
<223> OTHER INFORMATION: MGMT_FwLoop5B_M5_6A
<220> FEATURE:
<221> NAME/KEY: misc_feature
<222> LOCATION: (2)..(2)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
(Phosphoramidite of (S)-1-(4,4'-dimethoxytriphenylmetyloxy)-3-
pyrenemethyloxy-2-propanol)

<400> SEQUENCE: 39
cngacccnga cngcccngag cgcttcactg agactcgcgg t 41

<210> SEQ ID NO 40
<211> LENGTH: 40
<212> TYPE: DNA
<213> ORGANISM: Artificial
<220> FEATURE:
<223> OTHER INFORMATION: MGMT_FwLoop5B_M5_6B
<220> FEATURE:
<221> NAME/KEY: misc_feature
<222> LOCATION: (2)..(2)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)

<400> SEQUENCE: 40
cngacccnga cngcccngag cgcttcactg agactcgcgg 40

<210> SEQ ID NO 41
<211> LENGTH: 39
<212> TYPE: DNA
<213> ORGANISM: Artificial
<220> FEATURE:
<223> OTHER INFORMATION: MGMT_FwLoop5B_M5_8A
<220> FEATURE:
<221> NAME/KEY: misc_feature
<222> LOCATION: (2)..(2)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E (Phosphoramidite of (S)-1-(4,4'-dimethoxytriphenylmetyloxy)-3-pyrenemethyloxy-2-propanol)

<400> SEQUENCE: 41
cngacccnga cngcccngag cgcttcactg agacgcggt 39

<210> SEQ ID NO 42
<211> LENGTH: 40

-continued

```
<212> TYPE: DNA
<213> ORGANISM: Artificial
<220> FEATURE:
<223> OTHER INFORMATION: MGMT_FwLoop5B_M5_8B
<220> FEATURE:
<221> NAME/KEY: misc_feature
<222> LOCATION: (2)..(2)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)
<220> FEATURE:
<221> NAME/KEY: misc_feature
<222> LOCATION: (8)..(8)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)
<220> FEATURE:
<221> NAME/KEY: misc_feature
<222> LOCATION: (12)..(12)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)
<220> FEATURE:
<221> NAME/KEY: misc_feature
<222> LOCATION: (17)..(17)
<223> OTHER INFORMATION: Hydrophobic nucleotide of type E
      (Phosphoramidite of (S)-1-(4,4'-dimethoxytriphenylmetyloxy)-3-
      pyrenemethyloxy-2-propanol)

<400> SEQUENCE: 42

cngacccnga cngcccngag cgcttcactg agacgcggtg                         40
```